United States Patent
Wang et al.

(10) Patent No.: US 11,840,568 B2
(45) Date of Patent: Dec. 12, 2023

(54) LYMPHOCYTE ACTIVATION GENE-3 (LAG-3) BINDING ANTIBODY AND USE THEREOF

(71) Applicant: MAB-VENTURE BIOPHARM CO., LTD., Shanghai (CN)

(72) Inventors: Shaoxiong Wang, Shanghai (CN); John L. Xu, Shanghai (CN); Jing Zhao, Shanghai (CN); Ming Wang, Shanghai (CN); Juehua Xu, Shanghai (CN); Fei Song, Shanghai (CN)

(73) Assignee: MAB-VENTURE BIOPHARM CO., LTD., Shanghai (CN)

( * ) Notice: Subject to any disclaimer, the term of this patent is extended or adjusted under 35 U.S.C. 154(b) by 536 days.

(21) Appl. No.: 17/044,524

(22) PCT Filed: Apr. 1, 2019

(86) PCT No.: PCT/CN2019/080847
§ 371 (c)(1),
(2) Date: Oct. 1, 2020

(87) PCT Pub. No.: WO2019/192432
PCT Pub. Date: Oct. 10, 2019

(65) Prior Publication Data
US 2021/0147536 A1 May 20, 2021

(30) Foreign Application Priority Data
Apr. 2, 2018 (WO) ................ PCT/CN2018/081636

(51) Int. Cl.
*C07K 16/28* (2006.01)
*A61K 39/00* (2006.01)

(52) U.S. Cl.
CPC .... *C07K 16/2803* (2013.01); *A61K 2039/505* (2013.01); *C07K 2317/31* (2013.01); *C07K 2317/33* (2013.01); *C07K 2317/56* (2013.01); *C07K 2317/565* (2013.01); *C07K 2317/622* (2013.01); *C07K 2317/92* (2013.01)

(58) Field of Classification Search
CPC ............ C07K 16/2803; C07K 2317/31; C07K 2317/33; C07K 2317/56; C07K 2317/565; C07K 2317/622; C07K 2317/92; A61K 2039/505
See application file for complete search history.

(56) References Cited

U.S. PATENT DOCUMENTS

| | | | |
|---|---|---|---|
| 2011/0070238 | A1 | 3/2011 | Triebel et al. |
| 2017/0290914 | A1 | 10/2017 | Liang et al. |

FOREIGN PATENT DOCUMENTS

| | | | | |
|---|---|---|---|---|
| EP | 1987839 | A1 | 11/2008 | |
| JP | 2010526052 | A | 7/2010 | |
| JP | 201716489 | A | 6/2017 | |
| WO | 2014/140180 | A1 | 9/2014 | |
| WO | WO-2016033547 | A1 * | 3/2016 | ............. A61P 31/04 |
| WO | WO-2016161390 | A1 * | 10/2016 | ............. A61K 39/00 |

OTHER PUBLICATIONS

N. Poirier, et al; "Antibody-mediated depletion of lymphocyte-activation gene-3 (LAG-3+)-activated T lymphocytes prevents delayed-type hypersensitivity in non-human primates", Clinical & Experimental Immunology: 164(2): pp. 265-274; May 2011.
Japanese Office Action dated Sep. 7, 2021; Appln. No. 2020-554837.
International Search Report Application No. PCT/CN2019/080847; dated Aug. 26, 2019.

* cited by examiner

*Primary Examiner* — Adam Weidner
*Assistant Examiner* — Laura Ann Essex

(57) ABSTRACT

The present invention relates to an antibody binding to lymphocyte activation gene-3 (LAG-3) and use thereof.

19 Claims, 11 Drawing Sheets
Specification includes a Sequence Listing.

The amino acid sequence of the heavy chain variable region of clone 11452, the underlined parts being the sequences of CDR regions EVQLLESGAEVKKPGASVKVSCKASGYTFT<u>SYGIS</u>WVRQAPGQGLEWMG<u>WISAYNGN</u>

<u>TNYAQKLQG</u>RVTMTTDTSTSTAYMELRSLRSDDTAVYYCAR<u>DGWWELLRPDDAFDI</u>W

GQGTTVTVSS (SEQ ID NO: 41)

The amino acid sequence of the light chain variable region of clone 11452, the underlined parts being the sequences of CDR regions QLVLTQSPSVSVSPGQTASITC<u>SGDKLGDKYAY</u>WYQQKPGQAPVLVIY<u>YDSDRPS</u>GIPE RFSGSNSGNTATLTISRVEAGDEADYYC<u>QVWDSSSDQVV</u>FGGGTQLTVLG (SEQ ID NO: 43)

The amino acid sequence of the heavy chain variable region of clone 13380 (MV705-3-VH-DE+DD)

EVQLLESGAEVKKPGASVKVSCKASGYTFTSYGISWVRQAPGQGLEWMGWISAYNGN

TNYAQKLQGRVTMTTDTSTSTAYMELRSLRSDETAVYYCARDGWWELLRPDDAFDIW

GQGTTVTVSS (SEQ ID NO: 75)

The amino acid sequence of the light chain variable region of clone 13380 (MV705-3-VH-DE+DD)

QLVLTQSPSVSVSPGQTASITCSGDKLGDKYAYWYQQKPGQAPVLVIYYDSDRPSGIPE

RFSGSNSGNTATLTISRVEAGDEADYYCQVWDSSSDQVVFGGGTQLTVLG (SEQ ID NO: 43)

The amino acid sequence of the heavy chain variable region of clone 13381 (MV705-3-VH-ED+DD)

EVQLLESGAEVKKPGASVKVSCKASGYTFTSYGISWVRQAPGQGLEWMGWISAYNGN

TNYAQKLQGRVTMTTDTSTSTAYMELRSLRSEDTAVYYCARDGWWELLRPDDAFDIW

GQGTTVTVSS (SEQ ID NO: 77)

The amino acid sequence of the light chain variable region of clone 13381 (MV705-3-VH-ED+DD)

QLVLTQSPSVSVSPGQTASITCSGDKLGDKYAYWYQQKPGQAPVLVIYYDSDRPSGIPE

RFSGSNSGNTATLTISRVEAGDEADYYCQVWDSSSDQVVFGGGTQLTVLG (SEQ ID NO: 43)

Figure 11

LYMPHOCYTE ACTIVATION GENE-3 (LAG-3) BINDING ANTIBODY AND USE THEREOF

CROSS-REFERENCE TO RELATED APPLICATIONS

This application claims priority to PCT application No. PCT/CN20191080847, filed on Apr. 1, 2019, which claims priority to PCT application No. PCT/CN2018/081636, Apr. 2, 2018, hereby incorporated herein by reference in its entirety.

TECHNICAL FIELD

The present invention relates to the field of antibodies, and also relates to the use of the antibody and a method for preparing thereof. Specifically, the present invention relates to an antibody binding to lymphocyte activation gene-3 (LAG-3) and its use in the treatment of a disease.

BACKGROUND ART

Lymphocyte activation gene-3, i.e. LAG-3, also known as CD223, is a membrane protein as a member of the immunoglobulin superfamily. It has a molecular weight of 70 kDa and is located on human chromosome 12 (20p13.3). This membrane protein comprises four extracellular immunoglobulin superfamily (IgSF) domains: one V region and three C2 regions. Compared with the CD4 molecule, they are similarly located on the chromosome, and both LAG-3 molecule and the CD4 molecule comprise some common amino acids (<20%). Therefore, some scientists believe that they may have been evolved from the same gene[1]. The DNA encoding LAG-3 has 8 exons. The extracellular region of this molecule consists of four domains: D1, D2, D3 and D4. There is a 30-amino acids extra-loop with specificity in D1 domain. In addition, D1 belongs to the V-type immunoglobulin superfamily, while D2, D3 and D4 belong to the C2-type immunoglobulin superfamily. In the D1 and D3 domains, and in the D2 and D4 domains, there are many identical amino acid sequences. The four domains may be replicated from two genes of the IgSF region. The cytoplasmic region consists of three parts: (1) serine phosphorylation site 5454, which may be similar to the protein kinase C site of CD4; (2) a conserved KIEELE motif, which is different from that of any other known proteins; and (3) a repeated EP sequence[2].

Most of LAG-3 is expressed on cell membrane by forming a dimer in the D1 region. A mature LAG-3 may be broken on the cell membrane into a soluble portion p54 (consisting of D1, D2 and D3) with a relative molecular mass of 54,000 and a transmembrane-cytoplasmic portion p16 with a relative molecular mass of 16,000[3]. The breakage of an intact LAG-3 molecule is the proteolytic reaction of a linker peptide with 20 amino acids, which occurs between the D4 region and the transmembrane region. The breakage of a LAG-3 molecule into soluble molecules on the cytomembrane is regulated by the transmembrane matrix metalloproteinases AMAD10 and AMAD17, and the TCR signalling pathway plays an important role in these two regulatory modes[4].

LAG-3 molecule is mainly expressed on the surface of activated natural killer (NK) cells and T lymphocytes. It binds to HLA-II with high affinity, and is involved in the activation of lymphocytes[5, 2]. The LAG-3 negatively regulates the proliferation and activation of T lymphocytes and the dynamic balance of T cells[6]. The ectopic expression of LAG-3 is also involved in the regulatory activity of T cells. The research of Workman et al.[7] has found that the number of T cells in LAG-3 deficient aged mice is 2 times that in the wild type mice, the $CD4^+CD8_+LAG-3^-$ T cells can enhance the proliferation of lymphocytes and maintain homeostasis, and this function is terminated in the wild type mice due to the ectopic expression of LAG-3. In addition, in the in vivo treatment with anti-LAG-3 monoclonal antibodies, the proliferation of T cells can be significantly enhanced compared to the LAG-3 deficient cells. The research of Workman et al.[8] by the real-time fluorescence quantitative PCR found that the expression level of LAG-3 on the surface of plasmacytoid dendritic cells is 10 times that on the surface of the regulatory T cells or activated effector T cells, indicating that LAG-3 molecule may play an important role in the biological function of plasmacytoid dendritic cells.

Th1 cells express LAG-3, while Th2 cells have no or low expression of LAG-3. IL-12 has a potential to stimulate the expression of the LAG-3 molecule maximally[9]. LAG-3 molecule negatively regulates T cell expansion and controls memory T cell pool[10]. This negative regulation function is inseparable from the binding of LAG-3: MHC class II molecule, and requires the signal transduction through its cytoplasmic region structure. In particular, the negative regulation function is most closely related to the highly conserved KIEELE sequence. This regulation function is not based on competing with the CD4 molecule to bind to a MHC class II molecule. Therefore, LAG-3 is an independent, negative regulatory molecule[2].

LAG-3 negatively regulates $CD4^+$ T cells, and inhibits the proliferation of CD4Th1 cells and the secretion of cytokines (IFN-γ, IL-2, and TNF, etc.) through its intracellular signalling under the interaction of LAG-3: MHC II molecule. However, anti-LAG-3 antibodies can restore these functions, and promote cell proliferation and the secretion of related cytokines[11].

LAG-3 molecule also negatively regulates the activity of $CD8^+$ T cells. In mouse experiments, the inhibition of LAG-3 molecule can increase the proliferation of $CD8^+$ T cells, and also increase their cytotoxic activity, then IFN-γ is significantly increased. Simultaneously, LAG-3 molecule exhibits direct regulatory effect on $CD8^+$ T cells. The involvement of $CD4^+$ T cells is not required during the interaction of LAG-3 with $CD8^+$ T cells[2,11].

LAG-3 molecule also exhibits direct regulatory effect on the inhibitory function of $CD4^+CD25_+$ regulatory T cells (Treg cells)[11, 12], and is required for Treg cells to perform their function. Anti-LAG-3 antibodies can significantly inhibit the function of Treg cells and are closely related to the degree of maximization for cell function. Anti-LAG-3 antibodies can also expand the effector T cells by inhibiting the function of Treg cells, but cannot promote the apoptosis of Treg cells[13]. At the same time, the effector T cells can increase the expression of LAG-3 molecule in Treg cells in a dose-dependent manner. In addition, the ectopically expressed LAG-3 is also associated with the regulatory function of Treg cells. It can thus be seen that LAG-3 plays a very important role in the homeostasis in lymphocytes[14]. In addition, Liang et al.[15] found that Treg cells can inhibit the maturation of dendritic cells via cytoplasmic signalling by the cell-cell contact action between LAG-3 molecule on Treg cell surface and the MHC II molecules on dendritic cell membrane. This effect requires the involvement of mediation of the immunoreceptor tyrosine activation motif (ITAM) pathway.

During the tumor development, the tumor-specific CD8+ T cells in tumor tissues are numerically increased, but partially lose their function. The function of CD8+ T cells can be restored if an anti-LAG-3 antibody is used or LAG-3 gene is removed. As the number of CD8+ T cells and their cytotoxicity is increased, the secretion of cytokines is also increased. In addition, after blocking the function of LAG-3, the number and function of cytotoxic T lymphocytes in tumor tissues is significantly increased, and the tumor growth is inhibited; therefore, it is believed that inhibiting LAG-3 expression can restore immunological function of lymphocytes and inhibit the tumor development. Gandhi et al.[13] found that LAG-3 is highly expressed in lymphocytes in tumor tissues and peripheral blood of patients with Hodgkin's lymphoma. The obviously impaired function of specific CD8+ T cells in tumor tissues is negatively correlated with the number of CD4+CD25+ T cells highly expressing LAG-3 and/or FoxP3. If LAG-3+ T cells are removed, it is found that the anti-tumor function of specific CD8+ T cells can be restored, and the secretion of cytokines is increased. Therefore, LAG-3 expression is related to the negative immunoregulatory function of specific T cells. Inhibition of the function of LAG-3 molecule can enhance the anti-tumor effect of specific CD8+ T cells. This molecule may be a potential target of tumor immunotherapy.

The depletion of T cells often occurs in chronic viral infectious diseases. The research of Blackburn et al.[16] found that the depletion of CD8+ T cells is negatively regulated by co-expression of multiple inhibitory receptors. The depleted CD8+ T cells can express seven inhibitory receptors. The co-expression of a variety of different inhibitory receptors is closely related to the T cell depletion and more severe infections[17]. Blocking T cell inhibitory receptors PD-1 and LAG-3 can synergistically improve the T cell response and reduce the viral load in vivo. Konnai et al.[18] analyzed LAG-3 expression in cells in the cattle infected with the bovine leukemia virus, and found that the number of MHC class II molecules bound on LAG-3+CD8+ cells and LAG-3+CD3+ cells were significantly higher than that in control group animals. Compared with the cattle in the control group and the asymptomatic group, the average fluorescence intensity of LAG-3 molecule on peripheral blood mononuclear cells of the cattle consistently infected with the virus is significantly increased. However, the blocking experiments of PD-1 and LAG-3 indicate that, increasing anti-PD-1 and anti-LAG-3 antibodies in peripheral blood mononuclear cells of the cattle consistently infected with the virus can up-regulate the expression of INF-γ and IL-2. The above findings indicate that when infected with the virus, T cells exert inhibitory effect through the restriction effect of LAG-3 molecules and the expression of MHC class II signal molecules, and thereby LAG-3 may also be a target of viral immunotherapy.

CONTENTS OF THE INVENTION

Summary of the Invention

The present invention relates to the following embodiments:

1. An antibody binding to lymphocyte activation gene-3 (LAG-3), wherein the antibody significantly inhibits the interaction between LAG-3 and the major histocompatibility complex (MHC) class II molecule.

2. The antibody of embodiment 1, comprising a heavy chain variable region and a light chain variable region, wherein the heavy chain variable region comprises the following amino acid sequences:
SEQ ID NO: 41, SEQ ID NO: 45, SEQ ID NO: 49, SEQ ID NO: 53, SEQ ID NO: 57, SEQ ID NO: 61, SEQ ID NO: 75, or SEQ ID NO: 77; and the light chain variable region comprises the following amino acid sequence:
SEQ ID NO: 43, SEQ ID NO: 47, SEQ ID NO: 51, SEQ ID NO: 55, SEQ ID NO: 59, or SEQ ID NO: 63.

3. The antibody of embodiment 1 or 2, comprising a combination of a heavy chain variable region and a light chain variable region as follows:
   (1) amino acid sequences of SEQ ID NOs: 41 and 43;
   (2) amino acid sequences of SEQ ID NOs: 45 and 47;
   (3) amino acid sequences of SEQ ID NOs: 49 and 51;
   (4) amino acid sequences of SEQ ID NOs: 53 and 55;
   (5) amino acid sequences of SEQ ID NOs: 57 and 59;
   (6) amino acid sequences of SEQ ID NOs: 61 and 63;
   (7) amino acid sequences of SEQ ID NOs: 75 and 43; or
   (8) amino acid sequences of SEQ ID NOs: 77 and 43.

4. The antibody of any one of embodiments 1-3, comprising a heavy chain variable region and a light chain variable region, wherein the heavy chain variable region comprises the amino acid sequence of SEQ ID NO: 41, and the light chain variable region comprises the amino acid sequence of SEQ ID NO: 43.

5. An isolated anti-LAG-3 antibody comprising a heavy chain variable region and a light chain variable region, wherein the heavy chain variable region comprises:
   (a) a heavy chain variable region CDR1 comprising the sequence SYGIS (SEQ ID NO: 88);
   (b) a heavy chain variable region CDR2 comprising the sequence WISAYNGNTNYAQKLQG (SEQ ID NO: 89); and
   (c) a heavy chain variable region CDR3 comprising the sequence DGWWELLRPDDAFDI (SEQ ID NO: 90); and
   the light chain variable region comprises:
   (d) a light chain variable region CDR1 comprising the sequence SGDKLGDKYAY (SEQ ID NO: 91);
   (e) a light chain variable region CDR2 comprising the sequence YDSDRPS (SEQ ID NO: 92); and
   (f) a light chain variable region CDR3 comprising the sequence QVWDSSSDQVV (SEQ ID NO: 93).

6. The antibody of embodiment 5, comprising a heavy chain variable region and a light chain variable region, wherein:
   (1) the heavy chain variable region comprises the amino acid sequence of SEQ ID NO: 41, and the light chain variable region comprises the amino acid sequence of SEQ ID NO: 43;
   (2) the heavy chain variable region comprises the amino acid sequence of SEQ ID NO: 75, and the light chain variable region comprises the amino acid sequence of SEQ ID NO: 43; and
   (3) the heavy chain variable region comprises the amino acid sequence of SEQ ID NO: 77, and the light chain variable region comprises the amino acid sequence of SEQ ID NO: 43.

7. The antibody of any one of embodiments 1-6, wherein the antibody is a monoclonal antibody, a human antibody, a humanized antibody, or a chimeric antibody.

8. The antibody of any one of embodiments 1-7, wherein the antibody is an antibody fragment binding to LAG-3.

9. The antibody of embodiment 8, wherein the antibody fragment is a Fab, Fab'-SH, Fv, scFv, or (Fab')$_2$ fragment.

10. The antibody of any one of embodiments 1-7, wherein the antibody is a full length antibody.

11. The antibody of any one of embodiments 1-7, wherein the antibody is an IgG antibody.

12. The antibody of any one of embodiments 1-11, wherein the antibody is a monospecific antibody.

13. The antibody of any one of embodiments 1-11, wherein the antibody is a multispecific antibody.

14. The antibody of embodiment 13, wherein the multispecific antibody is a bispecific antibody.

15. The antibody of embodiment 14, wherein the bispecific antibody comprises a second binding domain that binds to a second biomolecule, and wherein the second biomolecule is a cell surface antigen.

16. The antibody of embodiment 15, wherein the cell surface antigen is a tumor antigen.

17. A pharmaceutical composition comprising the antibody of any one of embodiments 1-16 and a pharmaceutically acceptable carrier.

18. An immunoconjugate comprising a therapeutic agent that is linked to the antibody of any one of embodiments 1-16.

19. The immunoconjugate of embodiment 18, wherein the therapeutic agent is a cytotoxic agent.

20. A pharmaceutical composition comprising the immunoconjugate of embodiment 18 or 19, further comprising a pharmaceutically acceptable carrier.

21. An article comprising a container containing the pharmaceutical composition of embodiment 17 or 20 and a package insert, wherein the package insert illustrates the usage of the pharmaceutical composition.

22. The article of embodiment 21, further comprising one or more containers containing one or more additional drugs.

23. The article of embodiment 22, wherein the additional drug is selected from the group consisting of: an immunostimulatory antibody, a chemotherapeutic agent, and an antiviral drug.

24. An isolated nucleic acid encoding the antibody of any one of embodiments 1-16.

25. A vector comprising the isolated nucleic acid of embodiment 24.

26. A host cell comprising the vector of embodiment 25.

27. The host cell of embodiment 26, wherein the host cell is a mammalian cell.

28. The host cell of embodiment 27, wherein the mammalian cell is a Chinese hamster ovary (CHO) cell.

29. A method for preparing the antibody of any one of embodiments 1-16, comprising culturing the host cell of any one of embodiments 26-28.

30. The method of embodiment 29, further comprising recovering the antibody or antibody fragment binding to LAG-3 from the host cell or the culture medium.

31. A method for stimulating an antigen-specific T cell response, comprising contacting T cell with the antibody of any one of embodiments 1-16 to stimulate the antigen-specific T cell response.

32. A method for stimulating an immune response in a subject, comprising administering the antibody of any one of embodiments 1-16 to the subject, thereby stimulating the immune response in the subject.

33. The method of embodiment 32, wherein the subject is a subject carrying a tumor, and the administration of the antibody of any one of embodiments 1-16 to the subject stimulates an immune response against the tumor.

34. The method of embodiment 32, wherein the subject is a subject carrying a virus, and the administration of the antibody of any one of embodiments 1-16 to the subject stimulates an immune response against the virus.

35. A method for inhibiting the tumor cell growth in a subject, comprising administering the antibody of any one of embodiments 1-16 to the subject.

36. A method for treating a viral infection in a subject, comprising administering the antibody of any one of embodiments 1-16 to the subject.

37. The method of any one of embodiments 31-36, wherein the antibody of any one of embodiments 1-16 is used in combination with one or more additional drugs.

38. The method of embodiment 37, wherein the additional drug is selected from the group consisting of: an immunostimulatory antibody, an anticancer drug, and an antiviral drug.

39. The method of embodiment 38, wherein the immunostimulatory antibody is selected from the group consisting of: an anti-PD-1 antibody, an anti-PD-L1 antibody, an anti-PD-L2 antibody, and an anti-CTLA-4 antibody.

40. Use of the antibody of any one of embodiments 1-16 in the preparation of a medicament for stimulating an antigen-specific T cell response.

41. Use of the antibody of any one of embodiments 1-16 in the preparation of a medicament for stimulating an immune response in a subject.

42. The use of embodiment 41, wherein the subject is a subject carrying a tumor, and the administration of the antibody of any one of embodiments 1-16 to the subject stimulates an immune response against the tumor.

43. The use of embodiment 42, wherein the subject is a subject carrying a virus, and the administration of the antibody of any one of embodiments 1-16 to the subject stimulates an immune response against the virus.

44. Use of the antibody of any one of embodiments 1-16 in the preparation of a medicament for inhibiting the tumor cell growth in a subject.

45. Use of the antibody of any one of embodiments 1-16 in the preparation of a medicament for treating a viral infection in a subject.

46. The use of any one of embodiments 40-45, wherein the antibody of any one of embodiments 1-16 is used in combination with one or more additional drugs.

47. The use of embodiment 46, wherein the additional drug is selected from the group consisting of: an immunostimulatory antibody, an anticancer drug, or an antiviral drug.

DETAILED DESCRIPTION OF EMBODIMENTS

1. Definitions

The term "antibody" is used herein in a broad sense and encompasses various antibody structures, and includes, but is not limited to, monoclonal antibodies, polyclonal antibodies, multispecific antibodies (e.g., bispecific antibodies), and antibody fragments, as long as they exhibit the activity of binding to LAG-3.

The term "monoclonal antibody" as used herein refers to an antibody obtained from a substantially homogeneous antibody population, i.e., the individual antibodies constituting the population are identical and/or bind to the same epitope, but with exception of possible variant antibodies, which generally present in a minor amount and for example comprise naturally occurring mutations or mutations occurring during the preparation of the monoclonal antibodies. Each monoclonal antibody in a monoclonal antibody formulation directs against a single epitope on the antigen, as compared with a polyclonal antibody formulation that typically includes different antibodies directing against different epitopes. Thus, the modifier "monoclonal" refers to an antibody that is characterized by being obtained from a substantially homogeneous antibody population, and should not be considered as an antibody that needs to be prepared by any particular method. For example, the monoclonal antibody of the present invention can be made by a variety of techniques including, but not limited to, hybridoma methods, recombinant DNA methods, phage display methods, and methods for utilizing transgenic animals comprising all or part of a human immunoglobulin gene locus.

The terms "full length antibody" and "intact antibody" are used interchangeably herein to refer to an antibody having a structure that is substantially similar to the structure of the native antibody.

The "human antibody" may also be referred to as a "human being antibody", "fully human native antibody" or "full human antibody", which is the antibody with an amino acid sequence corresponding to the amino acid sequence of an antibody produced by a human being or a human cell or derived from an antibody of a non-human origin utilizing a human antibody lineage or other human antibody coding sequences. This definition of the human antibody specifically excludes a humanized antibody comprising non-human antigen binding residues. Human antibodies can be prepared by a variety of techniques known in the art, including the phage display library technology, and the technologies described in Hoogenboom and Winter, J. Mol. Biol., 227:381(1991); Marks et al., J. Mol. Biol., 222:581 (1991); Cole et al., Monoclonal Antibodies and Cancer Therapy, Alan R. Liss, p. 77 (1985); and Boerner et al., J. Immunol., 147(1): 86-95 (1991). Human antibodies can be prepared by administering an antigen to a transgenic animal (e.g., immunizing a xenogeneic mouse) that has been modified to produce such antibodies in response to antigenic challenge but the endogenous gene locus of the antibodies has been disabled (for the XENOMOUSE™ technology, see, for example, U.S. Pat. Nos. 6,075,181 and 6,150,584). For the human antibodies produced by the human B cell hybridoma technology, see, for example, Li et al., Proc. Natl. Acad. Sci. USA, 103: 3557-3562 (2006).

The term "chimeric" antibody refers to an antibody with a portion of the heavy chain and/or light chain derived from a particular source or species, and the remainder of the heavy chain and/or light chain is derived from a different source or species.

The "human common framework" is a framework that represents the most frequently occurring amino acid residues in the selection of human immunoglobulin VL or VH framework sequences. In general, the human immunoglobulin VL or VH sequence is selected from a subgroup of variable domain sequences. In general, the subgroup of the sequences is a subgroup as described in Kabat et al., Sequences of Proteins of Immunological Interest, 5th edition, NIH Publication 91-3242, Bethesda MD (1991), Volumes 1-3. In one embodiment, for the VL, the subgroup is the subgroup kappa I as described by Kabat et al. (supra). In one embodiment, for the VH, the subgroup is the subgroup III as described by Kabat et al. (supra).

The "humanized" antibody refers to a chimeric antibody comprising the amino acid residues derived from a non-human HVR and amino acid residues derived from a human FR. In certain embodiments, a humanized antibody comprises at least one and typically two or substantially all of variable domains, wherein all or substantially all of the HVRs (e.g., CDRs) correspond to the HVRs of non-human antibodies, and all or substantially all of the FRs correspond to the FRs of human antibodies. The humanized antibody can optionally comprise at least a part of an antibody constant region derived from a human antibody. A "humanized form" of a non-human antibody refers to an antibody that has been humanized.

The term "hypervariable region" or "HVR" as used herein refers to the individual regions that have sequence hypervariability (also referred to as "complementarity determining regions" or "CDRs") and/or form a structurally defined loop ("hypervariable loop") and/or comprise antigen-contacting residues ("antigen contact sites") in an antibody variable domain. In general, the antibody comprises 6 HVRs: 3 HVRs in the VH (H1, H2, H3), and 3 HVRs in the VL (L1, L2, L3). Exemplary HVRs herein include:
  (a) the hypervariable loop occurring at the amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));
  (b) the CDR occurring at the amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th edition, Public Health Service, National Institutes of Health, Bethesda, MD (1991));
  (c) the antigen contact sites occurring at the amino acid residues 27c-36 (L1), 46-55 (L2), 89-96 (L3), 30-35b (H1), 47-58 (H2) and 93-101 (H3) (MacCallum et al., J. Mol. Biol. 262:732-745 (1996)); and
  (d) a combination of (a), (b) and/or (c), comprising the HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, the HVR residues and other residues in the variable domain (e.g., FR residues) are numbered herein according to Kabat et al. (supra).

The term "variable region" or "variable domain" refers to an antibody heavy chain or light chain domain associated with the binding of an antibody to an antigen. The variable domains of the heavy chain and light chain (VH and VL, respectively) of a native antibody generally have similar structures, with each domain comprising four conserved framework regions (FRs) and three hypervariable regions (HVRs). (See, for example, Kindt et al., Kuby Immunology, 6th edition). A single VH or VL domain may be sufficient to confer antigen binding specificity. In addition, the VH or VL domains derived from an antibody binding to a particular antigen can be used to isolate the antibodies binding to the antigen, so as to screen libraries of complementary VL or VH domains, respectively. See, for example, Portolano et al., J. Immunol. 150: 880-887 (1993); Clarkson et al., Nature 352: 624-628 (1991).

The "antibody fragment" refers to, apart from an intact antibody, a molecule comprising a portion of an intact antibody that binds to an antigen to which the intact antibody binds. Examples of antibody fragments include, but are not limited to, Fv, Fab, Fab', Fab'-SH, F(ab')$_2$; a bifunctional antibody; a linear antibody; a single-chain antibody molecule (e.g. scFv); and a multispecific antibody formed from antibody fragments.

The term "cytotoxic agent" as used herein refers to a substance that inhibits or prevents cellular function and/or causes cell death or destruction. Cytotoxic agents include, but are not limited to, radioisotopes (e.g., At211, I131, I125, Y90, Re186, Re188, Sm153, Bi212, P32, Pb212, and a radioisotope of Lu); chemotherapeutic agents or drugs (e.g., methotrexate, adriamycin, vinca alkaloids (vincristine, vinblastine, etoposide), doxorubicin, melphalan, mitomycin C, chlorambucil, daunorubicin or other intercalating agents);

growth inhibitors; enzymes and fragments thereof, such as nucleolytic enzymes; antibiotics; toxins, such as small molecule toxins or enzymatically active toxins of bacterial, fungal, plant or animal origin, including fragments and/or variants thereof; and various antitumor drugs or anticancer agents known in the art.

The "immunoconjugate" is a conjugate of an antibody with one or more heterologous molecules (including but not limited to cytotoxic agents).

The "subject" or "individual" is a mammal. The mammal includes, but are not limited to, domesticated animals (e.g., cattle, sheep, cats, dogs, and horses), primates (e.g., humans and non-human primates, such as monkeys), rabbits, and rodents (e.g., mice and rats). In certain embodiments, the subject or individual is a human.

The term "package insert" is used to refer to an instruction generally included in the commercial package of a therapeutic product, and comprises the information about the indications, usage, dosage, drug administration, combination therapies, contraindications, and/or warnings regarding the use of such therapeutic product.

"Affinity" refers to the strength of the sum of non-covalent interactions between a single binding site of a molecule (e.g., an antibody) and its binding partner (e.g., an antigen). As used herein, "binding affinity" refers to an intrinsic binding affinity that reflects a 1:1 interaction between binding partner members (e.g., an antibody and an antigen), unless otherwise indicated. The affinity of molecule X to its partner Y is generally represented by the dissociation constant (Kd). Affinity can be measured by conventional methods known in the art, including those described herein. Specific illustrative and exemplary embodiments for measuring the binding affinity are described hereinafter.

The "percent (%) amino acid sequence homology" with respect to a reference polypeptide sequence is defined as the percentage of amino acid residues in a candidate sequence identical to the amino acid residues in the reference polypeptide sequence, when the alignment of the candidate sequence with the reference polypeptide sequence is performed, and if necessary, a gap is introduced to achieve maximal percent sequence homology, and no conservative substitutions are considered as part of sequence homology. A variety of ways in the art can be used to determine the percent amino acid sequence homology, for example publicly available computer softwares, such as BLAST, BLAST-2, ALIGN or Megalign (DNASTAR) software. Those skilled in the art can determine appropriate parameters for aligning sequences, including any algorithm needed to achieve the maximum alignment over the full length of the sequences being compared.

For example, in the case of an amino acid sequence comparison by using ALIGN-2, the % amino acid sequence homology of the specified amino acid sequence A with, to or relative to the specified amino acid sequence B is calculated as follows:

100×fraction (X/Y)

wherein X is the number of identically matched amino acid residues scored by the sequence alignment program ALIGN-2 in the alignment of A and B by using the program, and wherein Y is the total number of amino acid residues in B. It should be understood that where the length of amino acid sequence A is not equal to the length of amino acid sequence B, the % amino acid sequence homology of A to B will not be equal to the % amino acid sequence homology of B to A. Unless specifically stated otherwise, all the % amino acid sequence homology values used herein are obtained by using the computer program ALIGN-2.

2. Antibodies, Preparation Methods, Compositions and Articles

1) Antibodies

The present invention relates to an anti-LAG-3 antibody. In certain embodiments, the present invention provides an anti-LAG-3 antibody, which comprises a binding domain comprising at least 1, 2, 3, 4, 5 or 6 hypervariable regions (HVRs) (or referred to as complementary determining region (CDRs)) selected from: (a) HVR-H1 comprising an amino acid sequence of SEQ ID NO: 88 or an amino acid sequence having at least 90%, 95%, 96%, 97%, 98%, or 99% homology to SEQ ID NO: 88; (b) HVR-H2 comprising an amino acid sequence of SEQ ID NO: 89 or an amino acid sequence having at least 90%, 95%, 96%, 97%, 98%, or 99% homology to SEQ ID NO: 89; (c) HVR-H3 comprising an amino acid sequence of SEQ ID NO: 90 or an amino acid sequence having at least 90%, 95%, 96%, 97%, 98%, or 99% homology to SEQ ID NO: 90; (d) HVR-L1 comprising an amino acid sequence of SEQ ID NO: 91 or an amino acid sequence having at least 90%, 95%, 96%, 97%, 98%, or 99% homology to SEQ ID NO: 91; (e) HVR-L2 comprising an amino acid sequence of SEQ ID NO: 92 or an amino acid sequence having at least 90%, 95%, 96%, 97%, 98%, or 99% homology to SEQ ID NO: 92; and (f) HVR-L3 comprising an amino acid sequence of SEQ ID NO: 93 or an amino acid sequence having at least 90%, 95%, 96%, 97%, 98%, or 99% homology to SEQ ID NO: 93. In some cases, in an anti-LAG-3 antibody, the heavy chain variable (VH) domain (region) may comprise an amino acid sequence having at least 90% sequence homology (e.g., at least 91%, 92%, 93%, 94%, 95%, 96%, 97%, 98% or 99% sequence homology) to SEQ ID NO: 41, 75 or 77, or an amino acid sequence consisting of SEQ ID NO: 41, 75 or 77, and/or the light chain variable (VL) domain (region) comprises an amino acid sequence having at least 90% sequence homology (e.g., at least 91%, 92%, 93%, 94%, 95%, 96%, 97%, 98%, or 99% sequence homology) to SEQ ID NO: 43, or an amino acid sequence consisting of SEQ ID NO: 43.

In some embodiments, the anti-LAG-3 antibody comprises a heavy chain variable region and a light chain variable region, wherein the heavy chain variable region comprises the following amino acid sequences:
SEQ ID NO: 41, SEQ ID NO: 45, SEQ ID NO: 49, SEQ ID NO: 53, SEQ ID NO: 57, SEQ ID NO: 61, SEQ ID NO: 75, or SEQ ID NO: 77; and
the light chain variable region comprises the following amino acid sequence:
SEQ ID NO: 43, SEQ ID NO: 47, SEQ ID NO: 51, SEQ ID NO: 55, SEQ ID NO: 59, or SEQ ID NO: 63.

In some embodiments, the anti-LAG-3 antibody comprises a combination of a heavy chain variable region and a light chain variable region as follows:
(1) amino acid sequences of SEQ ID NOs: 41 and 43;
(2) amino acid sequences of SEQ ID NOs: 45 and 47;
(3) amino acid sequences of SEQ ID NOs: 49 and 51;
(4) amino acid sequences of SEQ ID NOs: 53 and 55;
(5) amino acid sequences of SEQ ID NOs: 57 and 59;
(6) amino acid sequences of SEQ ID NOs: 61 and 63;
(7) amino acid sequences of SEQ ID NOs: 75 and 43; or
(8) amino acid sequences of SEQ ID NOs: 77 and 43.

In some embodiments, the anti-LAG-3 antibody comprises a heavy chain variable region and a light chain variable region, wherein the heavy chain variable region comprises the amino acid sequence of SEQ ID NO: 41, SEQ ID NO: 75, or SEQ ID NO: 77, and the light chain variable region comprises the amino acid sequence of SEQ ID NO: 43.

2) Antibody Fragments

In certain embodiments, an antibody provided herein is an antibody fragment. The antibody fragments include, but are not limited to Fab, Fab', Fab'-SH, (Fab')$_2$, Fv and scFv fragments and other fragments described hereinafter. For a review of certain antibody fragments, see Hudson et al., Nat. Med. 9:129-134 (2003). For a review of scFv fragment, see, for example, Pluckthün, The Pharmacology of Monoclonal Antibodies, Vol. 113, Rosenburg and Moore eds. (Springer-Verlag, New York), pp. 269-315 (1994); see also WO 93/16185; and U.S. Pat. Nos. 5,571,894 and 5,587,458.

An bifunctional antibody is an antibody fragment having two antigen binding sites, which can be bivalent or bispecific. See, for example, EP 404,097; WO 1993/01161; Hudson et al., Nat. Med. 9:129-134 (2003); and Hollinger et al., Proc. Natl. Acad. Sci. USA 90:6444-6448 (1993). Trifunctional and tetrafunctional antibodies are also described in Hudson et al., Nat. Med. 9:129-134 (2003).

A single domain antibody is an antibody fragment comprising all or part of a heavy chain variable domain or all or part of a light chain variable domain of an antibody. In certain embodiments, the single domain antibody is a human single domain antibody (Domantis, Inc., Waltham, MA; see, for example, U.S. Pat. No. 6,248,516 B1).

Antibody fragments can be produced by a variety of techniques including, but not limited to, proteolytic digestion of intact antibodies and production by recombinant host cells (e.g., *E. coli* or phage) as described herein.

3) Chimeric Antibodies and Humanized Antibodies

In certain embodiments, the antibody provided herein is a chimeric antibody. Certain chimeric antibodies are described, for example, in U.S. Pat. No. 4,816,567; and Morrison et al., Proc. Natl. Acad. Sci. USA, 81:6851-6855 (1984).

In certain embodiments, the chimeric antibody is a humanized antibody. Typically, a non-human antibody is humanized to reduce immunogenicity to humans, while retaining the specificity and affinity of the parental non-human antibody. In general, a humanized antibody comprises one or more variable domains, wherein the HVR, e.g., CDR, (or a part thereof) is derived from a non-human antibody, and the FR (or a part thereof) is derived from a human antibody sequence. A humanized antibody can also optionally comprise at least a part of a human constant region. In some embodiments, some of the FR residues in a humanized antibody are substituted with corresponding residues from a non-human antibody (e.g., an antibody obtaining the HVR residues), e.g., to repair or improve antibody specificity or affinity.

Humanized antibodies and methods of producing them can be found, for example, in Almagro and Fransson, Front. Biosci. 13: 1619-1633 (2008), and are further described, for example, in Riechmann et al., Nature 332:323-329 (1988); U.S. Pat. Nos. 5,821,337, 7,527,791, 6,982,321 and 7,087,409; Kashmiri et al., Methods 36:25-34 (2005) (describing the transplantation of specificity determining regions (SDRs)); Padlan, Mol. Immunol. 28: 489-498 (1991) (describing "surface reforming"); Dall and Acqua et al., Methods 36: 43-60 (2005) (describing "FR reshuffling"); and Osbourn et al., Methods 36: 61-68 (2005) and Klimka et al., Br. J. Cancer, 83: 252-260 (2000) (describing the "guided selection" method for FR reshuffling).

4) Human Antibodies

In certain embodiments, the antibody provided herein is a human antibody. Human antibodies can be produced by a variety of techniques known in the art.

A human antibody can be prepared by administering an immunogen to a modified transgenic animal, and then challenging with an antigen to produce an intact human antibody or an intact antibody having human variable regions. Such animals typically comprise all or part of a human immunoglobulin gene locus, which replaces the endogenous immunoglobulin gene locus, or is present extrachromosomally, or is randomly integrated into the animal's chromosome. In such transgenic mice, the endogenous immunoglobulin gene locus has been generally inactivated. For a method of obtaining a human antibody from a transgenic animal, see, for example, U.S. Pat. Nos. 6,075,181 and 6,150,584 (describing the XENOMOUSE™ technology); U.S. Pat. Nos. 5,770,429; 7,041,870 (describing the K-M technology); US Application Publication No. 2007/0061900. Human variable regions derived from the intact antibodies produced by such animals can be further modified, for example by combining with different human constant regions.

A human antibody can also be made by hybridoma-based methods. Human myeloma and mouse-human hybrid myeloma cell strains for the production of human monoclonal antibodies have been described in, for example, Kozbor J. Immunol., 133:3001 (1984); Brodeur et al., Monoclonal Antibody Production Techniques and Applications, pp. 51-63; Marcel Dekker, Inc., New York, 1987); and Boerner et al., J. Immunol., 147:86 (1991). The human antibody produced via the human B cell hybridoma technology is also described in Li et al., Proc. Natl. Acad. Sci. USA, 103: 3557-3562 (2006). Other methods include, for example, the methods described in U.S. Pat. No. 7,189,826 (describing the production of monoclonal human IgM antibodies from hybridoma cell strains), and Ni, Xiandai Mianyixue, 26(4): 265-268 (2006) (describing human-human hybridomas). The human hybridoma technology (the Trioma technology) is also described in Vollmers and Brandlein, Histology and Histopathology, 20(3): 927-937 (2005); and Vollmers and Brandlein, Methods and Findings in Experimental and Clinical Pharmacology, 27(3): 185-91 (2005).

A human antibody can also be prepared by isolating the variable domain sequences of the Fv clones selected from a human-derived phage display library. Such variable domain sequences can then be combined with the desired human constant domain. The process of screening a human antibody by a phage display library is described in the Example section of the invention.

Specifically, an antibody of the present invention having high affinity can be isolated by screening a combinatorial library for an antibody having the activity of binding to LAG-3. For example, various methods for generating a phage display library and screening such a library for antibodies having the desired binding characteristics are known in the art. Such methods can be found, for example, in Hoogenboom et al., Methods in Molecular Biology 178: 1-37 (O'Brien et al., ed., Human Press, Totowa, NJ, 2001) and are further described, for example, in McCafferty et al., Nature 348: 552-554; Clackson et al., Nature 352: 624-628 (1991); Marks et al., J. Mol. Biol. 222: 581-597 (1992);

Marks and Bradbury, Methods in Molecular Biology 248: 161-175 (Lo edited, Human Press, Totowa, NJ, 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004).

In certain phage display methods, the VH and VL gene lineages are individually cloned by polymerase chain reaction (PCR) and randomly recombined in a phage library, followed by screening for the antigen-binding phage as described in Winter et al., Ann. Rev. Immunol., 12:433-455 (1994). Bacteriophages typically present the antibody fragments as single chain Fv (scFv) fragments or Fab fragments. A library derived from an immune source provides the antibodies with a high affinity to the immunogen without the need to construct hybridomas. Patent publications describing human antibody phage libraries include, for example, U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

An antibody or antibody fragment isolated from a human antibody library is considered herein as a human antibody or a human antibody fragment.

5) Multispecific Antibodies

In any of the above aspects, the anti-LAG-3 antibody provided herein is a multispecific antibody, such as a bispecific antibody. The multispecific antibody is a monoclonal antibody with binding specificities for at least two different sites. In certain embodiments, one binding specificity is for LAG-3 and the other binding specificity is for any other antigen (for example, a second biomolecule, e.g., a cell surface antigen, such as a tumor antigen). Accordingly, the bispecific anti-LAG-3 antibody may have binding specificities against LAG-3 and a tumor antigen, such as CD3, CD20, FcRH5, HER2, LYPD1, LY6G6D, PMEL17, LY6E, CD19, CD33, CD22, CD79A, CD79B, EDAR, GFRA1, MRP4, RET, Steap1, or TenB2. The bispecific antibody can also be prepared as a full length antibody or an antibody fragment.

Techniques for making the multispecific antibodies include, but are not limited to, recombinant co-expression of heavy chain-light chain pairs of two immunoglobulins with different specificities (see Milstein and Cuello, Nature 305: 537 (1983); WO 93/08829; and Traunecker et al., EMBO J. 10: 3655 (1991); WO 2009/080253; Schaefer et al., Proc. Natl. Acad. Sci. USA, 108: 11187-11192 (2011); WO 2009/089004 A1, and so on).

6) Antibody Variants

An antibody of the invention encompasses amino acid sequence variants of the anti-LAG-3 antibody of the invention. For example, antibody variants prepared to further improve the binding affinity and/or other biological properties of the antibody may be desirable. Amino acid sequence variants of an antibody can be prepared by introducing appropriate modifications into a nucleotide sequence encoding the antibody or by peptide synthesis. Such modifications comprise, for example, deletions, and/or insertions, and/or substitutions of residues within the amino acid sequence of an antibody. Any combination of deletions, insertions, and substitutions can be made to obtain a final construct, provided that the final construct has desired characteristics, such as antigen binding.

a. Substitution Variants, Insertion Variants, and Deletion Variants

In certain embodiments, provided are antibody variants having one or more amino acid substitutions. The relevant sites induced by the substitutional mutations comprise HVRs and FRs. Conservative substitutions are shown below under the heading "Preferred Substitutions". Additional substantial changes are provided below under the heading "Exemplary Substitutions", and are further described below with reference to the classes of amino acid side chains. Amino acid substitutions can be introduced into the relevant antibodies, and the products are screened for the desired activity (e.g., retention/improvement of antigen binding or improvement of ADCC or CDC).

Exemplary Amino Acid Substitutions and Preferred Amino Acid Substitutions

Amino acids can be grouped according to the common nature of the side chains:
 (1) Hydrophobic: norleucine, Met, Ala, Val, Leu, and Ile;
 (2) Neutral hydrophilic: Cys, Ser, Thr, Asn, and Gln;
 (3) Acidic: Asp, and Glu;
 (4) Basic: His, Lys, and Arg;
 (5) Residues affecting chain orientation: Gly, and Pro; and
 (6) Aromatic: Trp, Tyr, and Phe.

Non-conservative substitutions will inevitably be accompanied by the exchange of a member of one of these categories into a member of another category.

One type of substitutional variants involves the substitution of one or more hypervariable region residues of a parent antibody (e.g., a humanized antibody or a human antibody). In general, the resulting variants selected for further study will be modified (e.g., improved) relative to the parent antibody in certain biological properties (e.g., increased affinity), and/or will substantially retain certain biological properties of the parent antibody. Exemplary substitutional variants are affinity matured antibodies, which can be conveniently produced by using, for example, the phage display-based affinity maturation techniques, such as those described herein. Briefly, one or more HVR residues are mutated, and the variant antibodies are displayed on the phage and screened for a particular biological activity (e.g., binding affinity).

In certain embodiments, substitutions, insertions, or deletions can occur within one or more HVRs (CDRs), as long as such changes do not substantially impair the ability of the antibody to bind LAG-3. For example, conservative changes (e.g., conservative substitutions as provided herein) can be made in the HVRs without substantially reducing the binding affinity. For example, such changes can be outside of the antigen-contacting residues in the HVRs. In certain embodiments of the variant VH and VL sequences provided above, each HVR is unchanged or comprises no more than 1, 2 or 3 amino acid substitutions.

A suitable method for identifying the antibody residues or regions targetable for mutation induction is referred to as "alanine scanning mutation induction", as described by Cunningham and Wells (1989) Science, 244: 1081-1085.

7) Recombination Methods

The anti-LAG-3 antibody of the invention can be prepared by recombinant methods, for example, as described in U.S. Pat. No. 4,816,567. In one embodiment, provided is an isolated nucleic acid encoding the anti-LAG-3 antibody described herein. Such nucleic acids may encode an amino acid sequence comprising the VL and/or an amino acid sequence comprising the VH of the antibody (e.g., the light chain and/or heavy chain of the antibody). In another embodiment, provided are one or more vectors (e.g., expression vectors) comprising such nucleic acids. In another embodiment, provided is a host cell comprising such nucleic acids. In one of such embodiments, the host cell comprises (e.g., has been transformed to have): (1) a vector comprising a nucleic acid that encodes an amino acid sequence comprising the VL of the antibody and an amino acid sequence comprising the VH of the antibody; or (2) a first vector comprising a nucleic acid that encodes an amino acid sequence comprising the VL of the antibody, and a second vector comprising a nucleic acid that encodes an amino acid sequence comprising the VH of the antibody. In one embodiment, the host cell is a eukaryotic cell, such as a Chinese hamster ovary (CHO) cell or a lymphoid cell (e.g., Y0, NS0, and Sp20 cells). In one embodiment, provided is a method for making an anti-LAG-3 antibody, wherein the method comprises culturing a host cell comprising a nucleic acid encoding the antibody as provided above under conditions suitable for the expression of the antibody, and optionally recovering the antibody from the host cell (or the culture medium of the host cell).

For recombinant production of the anti-LAG-3 antibody, the nucleic acid (e.g., as described above) encoding the antibody is isolated and inserted into one or more vectors for further cloning and/or expression in a host cell. Such nucleic acids can be readily isolated and sequenced by conventional procedures (e.g., by using oligonucleotide probes capable of specifically binding to the genes encoding the heavy chain and light chain of the antibody).

Host cells suitable for cloning or expressing antibody-encoding vectors comprise prokaryotic or eukaryotic cells as described herein. For example, antibodies can be produced in bacteria, especially when the glycosylation and Fc effector functions are not required. For the expression of antibody fragments and polypeptides in bacteria, see, for example, U.S. Pat. Nos. 5,648,237, 5,789,199, and 5,840,523. After expression, the antibody in the soluble portion can be isolated from the bacterial cytoplasm and can be further purified.

In addition to prokaryotes, eukaryotic microorganisms such as filamentous fungi or yeast are also suitable hosts for cloning or expressing the antibody-encoding vectors, including the fungal and yeast strains having the glycosylation pathways that have been "humanized" to produce antibodies having partial or complete human glycosylation patterns. See Gerngross, Nat. Biotech. 22: 1409-1414 (2004); and Li et al., Nat. Biotech. 24: 210-215 (2006).

Host cells suitable for expressing the glycosylated antibodies are also derived from multicellular organisms (invertebrates and vertebrates). Examples of invertebrate cells comprise plant and insect cells. A number of baculovirus strains capable of infecting insect cells, particularly transfecting *Spodoptera frugiperda* cells have been identified.

Plant cell cultures can also be used as hosts. See, for example, U.S. Pat. Nos. 5,959,177, 6,040,498, 6,420,548, 7,125,978, and 6,417,429 (describing the PLANTIBODIES technology for producing antibodies in transgenic plants).

Vertebrate cells can also be used as hosts. For example, mammalian cell strains suitable for growth in suspension may be applicable. Additional examples of applicable mammalian host cell stains are SV40 transformed monkey kidney CV1 cell strains (COS-7); human embryonic kidney cell strains (e.g., the 293 or 293 cells as described in Graham et al., J. Gen Virol. 36: 59 (1977)); baby hamster kidney cells (BHK); mouse Sertoli cells (e.g., the TM4 cells as described in Mather, Biol. Reprod. 23: 243-251 (1980)); monkey kidney cells (CV1); African green monkey kidney cells (VERO-76); human cervical cancer cells (HELA); canine kidney cells (MDCK); Buffalo rat liver cells (BRL3A); human lung cells (W138); human hepatocytes (Hep G2); mouse mammary tumors (MMT 060562); for example, the TRI cells as described in Mather et al., Annals NY Acad. Sci. 383: 44-68 (1982); MRC 5 cells; and FS4 cells. Other applicable mammalian host cell strains comprise Chinese hamster ovary (CHO) cells, including DHFR-CHO cells (Urlaub et al., Proc. Natl. Acad. Sci. USA 77: 4216 (1980)); and myeloma cell strains, such as Y0, NS0 and Sp2/0. For a review of certain mammalian host cell strains suitable for producing antibodies, see, for example, Yazaki and Wu, Methods in Molecular Biology, Vol. 248 (B.K.C.Lo, ed., Humana Press, Totowa, NJ), pp. 255-268 (2003).

8) Immunoconjugates

The invention also provides an immunoconjugate formed by the combination of anti-LAG-3 antibody with one or more cytotoxic agents, such as chemotherapeutic agents or chemotherapeutic drugs, growth inhibitors, toxins (e.g., protein toxins, enzymatically active toxins or fragments thereof derived from bacteria, fungi, plants or animals) or radioisotopes.

In one embodiment, the immunoconjugate is an antibody-drug conjugate (ADC), wherein the antibody binds to one or more drugs, including but not limited to: maytansine (see U.S. Pat. Nos. 5,208,020, 5,416,064 and European patent EP 0 425 235 B1); auristatin, such as monomethyl auristatin drug portion DE and DF (MMAE and MMAF) (see U.S. Pat. Nos. 5,635,483 and 5,780,588 and 7,498,298); dolastatin; calicheamicin or derivatives thereof (see U.S. Pat. Nos. 5,712,374, 5,714,586, 5,739,116, 5,767,285, 5,770,701, 5,770,710, 5,773,001 and 5,877,296; Hinman et al., Cancer Res. 53: 3336-3342 (1993); and Lode et al., Cancer Res. 58: 2925-2928 (1998)), methotrexate; vindesine; taxanes, such as docetaxel, paclitaxel, larotaxel, tesetaxel, and ortataxel; trichothecene; and CC1065.

In another embodiment, the immunoconjugate comprises a conjugate of the anti-LAG-3 antibody as described herein and an enzymatically active toxin or fragments thereof, the enzymatically active toxin including, but not limited to, diphtheria A chain, non-binding active fragments of diphtheria toxin, exotoxin A chain and trichothecene.

In another embodiment, the immunoconjugate comprises a radioconjugate formed by the combination of the anti-LAG-3 antibody as described herein with a radioactive atom. A variety of radioisotopes are available for the production of the radioconjugate. Examples of the radioisotopes comprise $At^{211}$, $I^{131}$, $I^{125}$, $Y^{90}$, $Re^{186}$, $Re^{188}$, $Sm^{153}$, $Bi^{212}$, $P^{32}$, $Pb^{212}$, and a radioisotope of Lu.

The conjugate of an antibody and a cytotoxic agent can be made by using a variety of bifunctional protein coupling agents, such as N-succinimido-3-(2-pyridyldithio)propionate (SPDP), succinimido-4-(N-maleimidomethyl)cyclohexane-1-carboxylate (SMCC), imidothiacyclopentane (IT), bifunctional derivatives of imidate ester (such as dimethyl adipate hydrochloride), active esters (such as disuccinimide octanedioate), aldehydes (such as glutaraldehyde), diazido compounds (such as bis(p-azidobenzoyl)hexanediamine), disazo derivatives (such as bis(p-diazobenzoyl)ethanediamine), diisocyanates (such as toluene 2,6-diisocyanate) and double active fluorine compounds (such as 1,5-difluoro-2,4-dinitrobenzene).

9) Pharmaceutical Formulations

A pharmaceutical formulation of the anti-LAG-3 antibody of the invention is prepared by mixing an antibody having the desired purity with optionally one or more pharmaceutically acceptable carriers (Remington's Pharmaceutical Sciences, 16th edition, Osol, A., ed. (1980)) to form a lyophilized formulation or an aqueous solution. The pharmaceutically acceptable carriers are generally non-toxic to a recipient at the dosage and concentration employed, and include, but are not limited to, buffers such as phosphates, citrates, and other organic acids; antioxidants, including ascorbic acid and methionine; preservatives (such as octadecyldimethylbenzyl ammonium chloride; hexamethonium chloride; benzalkonium chloride; benzethonium chloride; phenol, butanol or benzyl alcohol; alkyl p-hydroxybenzoates such as methyl p-hydroxybenzoate or propyl p-hydroxybenzoate; catechol; resorcinol; cyclohexanol; 3-pentanol; and m-cresol); low molecular weight (less than about 10 residues) polypeptides; proteins, such as serum albumin, gelatin or immunoglobulin; hydrophilic polymers, such as polyvinylpyrrolidone; amino acids, such as glycine, glutamine, asparagine, histidine, arginine, or lysine; monosaccharides, disaccharides and other carbohydrates, including glucose, mannose, or dextrins; chelating agents, such as EDTA; sugars, such as sucrose, mannitol, fucose, or sorbitol; salt-forming counterions, such as sodium; metal complexes (e.g., zinc-protein complexes); and/or non-ionic surfactants, such as polyethylene glycol (PEG).

Exemplary lyophilized antibody formulations are described in U.S. Pat. No. 6,267,958. Aqueous antibody formulations comprise those described in U.S. Pat. No. 6,171,586 and WO 2006/044908, and the formulation in the latter comprises histidine-acetate buffer.

The formulations herein may also comprise more than one active ingredients which is necessarily present for a particular indication being treated, preferably the active ingredients having complementary activities which do not adversely affect each other. For example, it may be desirable to further provide additional therapeutic agents (e.g., chemotherapeutic agents, cytotoxic agents, growth inhibitors, and/or antihormone agents). Such active ingredients are suitably present in combination in an amount effective for the intended purpose.

10) Articles

In another aspect of the invention, provided is an article comprising an antibody or pharmaceutical composition of the invention. The article comprises a container and a label or package insert on or associated with the container. Suitable containers comprise, for example, bottles, vials, syringes, IV solution bags, and the like. Such containers can be formed from a variety of materials such as glass or plastic. The container holds the composition of the invention itself or a combination of the composition with another composition, and can have a sterile access port (for example, the container can be an intravenous solution bag or a vial having a stopper which can be pierced by a hypodermic needle). At least one active agents in the composition is the antibody of the invention. The label or package insert indicates that the composition is used to treat a selected tumor or viral infection. Additionally, the article comprises: (a) a first container comprising a composition, wherein the composition comprises the antibody of the invention; and (b) a second container comprising a composition, wherein the composition comprises another cytotoxic agent or additional therapeutic agents. The article of this embodiment of the invention can further comprise a package insert indicating that such compositions are useful for treating a tumor or a viral infection. Alternatively or in addition, the article can further comprise a second (or third) container comprising a pharmaceutically acceptable buffer, such as bacteriostatic water for injection (BWFI), a phosphate buffered saline, Ringer's solution, and a dextrose solution. It can further comprise other materials required from a commercial and user perspective, including other buffers, diluents, filters, needles, and syringes.

BRIEF DESCRIPTION OF THE DRAWINGS

FIG. 11 shows the amino acid sequences of the heavy chain variable region and the light chain variable region and the CDR sequences of clone 11452, clone 13380 and clone 13381.

EXAMPLES

Figure 1:
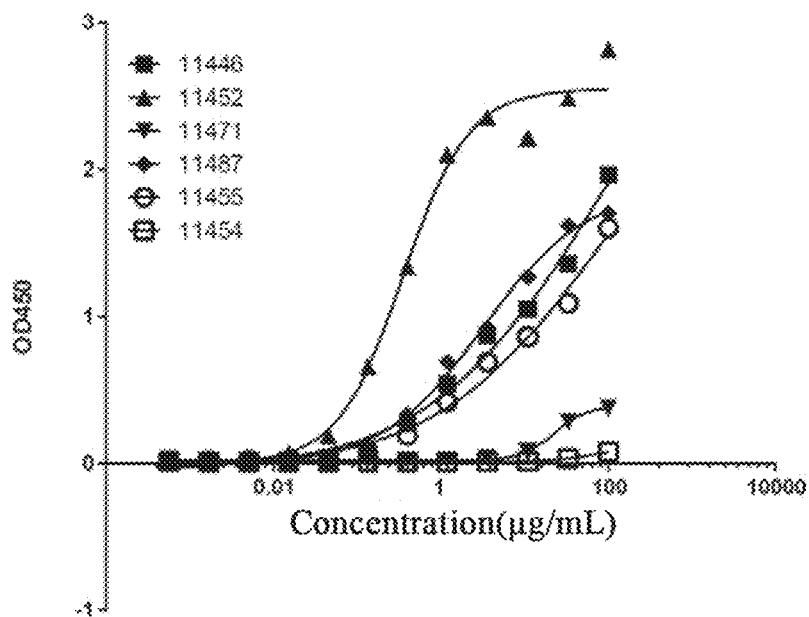
FIG. 1 shows the results of the in vitro binding activity assay of six IgG4 monoclonal antibodies and a human LAG-3-6*His tag fusion protein.

Example 1. Preparation of an Anti-LAG-3 Monoclonal Antibody 1.1. Panning of a Single Chain Antibody that Binds to a Human LAG-3 Recombinant Fusion Protein with High Affinity This example describes a method for panning a single chain antibody that binds to the human LAG-3 recombinant fusion protein with high affinity from a full human single chain scFv phage display library, and the method involves utilizing a full human single chain scFv phage display library as described below and a commercially available human LAG-3-6*His recombinant fusion protein (Novoprotein corporation, Cat #CJ91), *E. coli* TG1 (Lucigen, Cat #60502-1) and M13KO7 helper phage (Thermo Fisher, Cat

18311019). The full human single chain scFv phage display library of this example was constructed from the phagemid vector pCLS1.0 (SEQ ID NO: 1) comprising the pBR3.22 promoter and the M13 phage pIII protein display system, and the phagemid vector pCLS1.0 comprises Myc-His tag at the C-terminus. The *E. coli* TG1 was used for library construction. The full human single chain scFv phage display library was established by conventional methods well known in the literatures, and the main procedures are summarized as follows: RNAs were obtained from commercially available PBMCs of healthy population (ALLCELLS, Cat #PB-003F-S, 50 samples) by using an RNA extraction kit (TaKaRa, Cat #9767), and each full human scFv single chain phage display sub-library was established by mixing the RNAs of five or ten samples. The RNA was reverse transcribed to synthesize the first strand of cDNA by using a reverse transcription kit (Thermo Fisher, Cat #4368814), and the specific primers for amplifying the genes of human antibody variable regions were designed and synthesized with reference to the literature (Cai X H and Garen A. PNAS, 1995, 92(14): 6537-6541) and the V-base database. The first strand of cDNA was used as a template to amplify the genes of the heavy chain variable region and light chain variable region of the human antibody respectively by PCR. The gene fragments of the heavy chain variable region and light chain variable region of the human antibody were cloned respectively into the phagemid vector pCLS1.0 by molecular cloning techniques. Specifically, the gene of the human antibody light chain variable region was double-digested with Nhe I/Not I and cloned into the vector pCLS1.0, and then electrotransformed into *E. coli* TG1 to obtain phage light chain sub-libraries, thereby obtaining vector pCLS1.0-VL. The gene of the human antibody heavy chain variable region was cloned into the vector pCLS1.0-VL by continuing double digestion with Sfi I/Xho I. Full human scFv phage display sub-libraries having a combination of the heavy chain and light chain variable regions were obtained by using the same method. The total library capacity of the sub-libraries was $9 \times 10^9$.

All of the human LAG-3-6*His tag fusion proteins in the panning experiment were labelled with biotin by using the Biotin Labeling Kit-NH2 (Dojindo, Cat #LK03). The panning experiment is briefly described as follows: the M13K07 helper phage was prepared by using *E. coli* TG1, with a detected titer of about $1.0 \times 10^{13}$, and the above full human scFv single chain phage display library with OD600 value of 0.5-0.6 was infested with the phage to obtain the first round of input phages. Using liquid phase panning strategy, the phage of the scFv single chain antibody binding to the human LAG-3 was enriched by the human LAG-3-6*His tag recombinant fusion protein labelled with biotin, and the recombinant fusion protein was pre-incubated with the Dynabeads® M-280 Streptavidin (Thermo, Cat #11206D). The single chain antibody phage enriched was eluted with a 0.1 M glycine-hydrochloric acid solution (pH 2.2) to obtain the first round of output phages. The *E. coli* TG1 with an OD600 value of 0.5-0.6 was infected with the first round of output phages to obtain the second round of input phages. The second round of output phages that binds to the human LAG-3-6*His tag recombinant fusion protein were obtained by continuing to use the above bio-panning method. The third round or the fourth round of panning was performed by repeating the second round of bio-panning process. The *E. coli* TG1 was infected by the output phage enriched in the third round or the fourth round of panning, thereby obtaining single clones. By phage ELISA, the single clone *E. coli* with a high affinity to the human LAG-3-6*His tag recombinant fusion protein was identified and selected for sequencing analysis. 19 individual nucleotide sequences were obtained. See Table 1 for the specific sequence information.

TABLE 1

Corresponding relationship of the 19 clones and their nucleotide and amino acid sequences

| Clones | Nucleotide sequences | Amino acid sequences |
|---|---|---|
| 11446 | SEQ ID NO: 2 | SEQ ID NO: 3 |
| 11449 | SEQ ID NO: 4 | SEQ ID NO: 5 |
| 11451 | SEQ ID NO: 6 | SEQ ID NO: 7 |
| 11452 | SEQ ID NO: 8 | SEQ ID NO: 9 |
| 11453 | SEQ ID NO: 10 | SEQ ID NO: 11 |
| 11454 | SEQ ID NO: 12 | SEQ ID NO: 13 |
| 11455 | SEQ ID NO: 14 | SEQ ID NO: 15 |
| 11458 | SEQ ID NO: 16 | SEQ ID NO: 17 |
| 11465 | SEQ ID NO: 18 | SEQ ID NO: 19 |
| 11469 | SEQ ID NO: 20 | SEQ ID NO: 21 |
| 11471 | SEQ ID NO: 22 | SEQ ID NO: 23 |
| 11474 | SEQ ID NO: 24 | SEQ ID NO: 25 |
| 11482 | SEQ ID NO: 26 | SEQ ID NO: 27 |
| 11487 | SEQ ID NO: 28 | SEQ ID NO: 29 |
| 11489 | SEQ ID NO: 30 | SEQ ID NO: 31 |
| 11491 | SEQ ID NO: 32 | SEQ ID NO: 33 |
| 11501 | SEQ ID NO: 34 | SEQ ID NO: 35 |
| 11506 | SEQ ID NO: 36 | SEQ ID NO: 37 |
| 11507 | SEQ ID NO: 38 | SEQ ID NO: 39 |

1.2. Selection of the Single Chain Antibodies Binding to LAG-3 Protein for IgG Conversion by Flow Cytometry Analysis To test the binding activity of the 19 monoclonal scFv single chain antibodies to LAG-3 protein on the cell surface, the *E. coli* single clones carrying the scFv single chain antibodies were induced with IPTG to express the soluble scFv single chain antibody protein. The filtered supernatant was taken to detect their binding activity to the activated human CD4+ cells. The CD4+ T cells were isolated from human peripheral blood PBMCs using human CD4+ T cell enrichment kit (STEMCELL, Cat #19052). The isolated CD4+ T cells were activated by co-incubating with CD3/CD28 Dynabeads (Gibco, Cat #11131D) for 48 h in 5% $CO_2$ incubator at 37° C. The described 19 soluble scFv single chain antibody proteins expressed under IPTG induction, the 2YT medium (Sangon Biotech (Shanghai) Co., Ltd., Cat #SD7019) and blank control PBS (Hyclone, Cat #SH30256.01) were respectively co-incubated with the activated human CD4+ T cells at 4° C. for 1 h. The cells were then washed twice with a cold 1×PBS buffer. An anti-His-PE-labelled antibody (Miltenyi Biotec, Cat #130-092-691) diluted at 1:50 was added, and the mixture was incubated at 4° C. for 30 minutes, followed by washing twice with cold 1×PBS buffer. The binding activity of the scFv single chain antibody expressed under induction to the activated CD4 positive T cells was analyzed by a Guava easyCyte HT flow cytometer (MERCK MILLIPORE). In the flow cytometry analysis, gating is used to screen the CD4 positive T cells expressing LAG-3. The results are shown in Table 2. Six (11446, 11452, 11454, 11455, 11471, and 11487) of the 19 soluble scFv single chain antibody proteins expressed by the monoclones under induction have the highest binding activity to the activated human CD4 positive T cells.

TABLE 2

Binding activity of the 19 soluble scFv single chain antibody proteins expressed under IPTG induction to the activated human CD4+ T cells

| Test Articles | Binding activity |
|---|---|
| 2YT medium | − |
| Blank control PBS | − |
| 11446 | ++ |
| 11449 | + |
| 11451 | + |
| 11452 | +++ |
| 11453 | − |
| 11454 | ++ |
| 11455 | +++ |
| 11458 | + |

TABLE 2-continued

Binding activity of the 19 soluble scFv single chain antibody proteins expressed under IPTG induction to the activated human CD4+ T cells

| Test Articles | Binding activity |
|---|---|
| 11465 | + |
| 11469 | − |
| 11471 | ++ |
| 11474 | − |
| 11482 | − |
| 11487 | ++ |
| 11489 | − |
| 11491 | − |
| 11501 | − |
| 11506 | + |
| 11507 | + |

The 6 genes of scFv single chain antibodies (11446, 11452, 11454, 11455, 11471, and 11487) were selected for molecular cloning to convert into the form of fully IgG4 antibody. In general, the sequences comprising a leader peptide, Nhe I/Not I restriction sites, a heavy chain constant region gene, and a human IgG4-Fc were cloned and constructed into the pCDNA3.3+, thereby obtaining a vector pCDNA3.3-IgG4. Similarly, the sequences comprising a leader peptide, Nhe I/B siW I restriction sites, and a light chain Kappa constant region gene were cloned and constructed into the pCDNA3.3+, thereby obtaining a vector pCDNA3.3-VKappa, or the sequences comprising a leader peptide, BamH I/Hind III restriction sites, and a light chain lambda constant region gene were cloned and constructed into the pCDNA3.3+, thereby obtaining a vector pCDNA3.3-VLambda. Nhe I/Not I sites were added to two ends of the nucleotide sequence of the heavy chain variable region gene of the aforementioned scFv single chain antibody, and the resulting sequence was inserted into the corresponding site of the pCDNA3.3-IgG4 plasmid; Nhe I/BsiW I sites were added to two ends of the nucleotide sequence of the light chain variable region of the aforementioned scFv single chain antibody, and the resulting sequence was inserted into the corresponding site of the pCDNA3.3-Vkappa plasmid, or the nucleotide sequence of the light chain variable region of the scFv single chain antibody was inserted into the pCDNA3.3-VLambda vector using the BamH I/Hind III restriction sites. The recombinant plasmids expressing the monoclonal antibodies were obtained (see Table 3), wherein all of the heavy chains were IgG4 (Padlan E A Mol Immunol. 1994 February; 31(3):169-217. Anatomy of the antibody molecule).

TABLE 3

The sequences of the heavy chain variable regions and light chain variable regions of the 6 monoclonal antibodies

| Clones | Heavy chain variable region Nucleotide sequences | Heavy chain variable region Amino acid sequences | Light chain variable region Nucleotide sequences | Light chain variable region Amino acid sequences |
|---|---|---|---|---|
| 11452 | SEQ ID NO: 40 | SEQ ID NO: 41 | SEQ ID NO: 42 | SEQ ID NO: 43 (Lambda) |
| 11446 | SEQ ID NO: 44 | SEQ ID NO: 45 | SEQ ID NO: 46 | SEQ ID NO: 47 (Kappa) |
| 11454 | SEQ ID NO: 48 | SEQ ID NO: 49 | SEQ ID NO: 50 | SEQ ID NO: 51 (Lambda) |
| 11455 | SEQ ID NO: 52 | SEQ ID NO: 53 | SEQ ID NO: 54 | SEQ ID NO: 55 (Kappa) |
| 11471 | SEQ ID NO: 56 | SEQ ID NO: 57 | SEQ ID NO: 58 | SEQ ID NO: 59 (Kappa) |
| 11487 | SEQ ID NO: 60 | SEQ ID NO: 61 | SEQ ID NO: 62 | SEQ ID NO: 63 (Lambda) |

1.3. Expression, Purification, Identification and Binding Activity of the IgG4 Monoclonal Antibodies The recombinant plasmids comprising the heavy chain variable region and the light chain variable region listed in the Table 3 above were transiently transfected into the suspension-cultured ExpiCHO-S cells (Thermo Fisher, cat #A29127) by the liposome method with the ExpiFectamine™ CHO Transfection Kit (Thermo Fisher, Cat #A29129).

The resulting transfected ExpiCHO-S cells were cultured in 30 ml of ExpiCHO Expression medium (Thermo Fisher, Cat #A29100-01) under conditions of 37° C., 8% $CO_2$ with a rotation speed of 120 rpm.

After culturing for 10-14 days the transfected cells were subjected to two stages of centrifugation (the first stage of centrifugation lasted for 20 min at 400 g; and the second stage of centrifugation lasted for 20 min at 10000 g) to remove the cells and cell debris, and a supernatant was obtained. The clarified supernatant was loaded onto a Protein A affinity chromatography column (GE Healthcare, Cat #GE-17-5438-04). The impurities were removed by three-step washing (the washing buffers were a phosphate buffer comprising 150 mM NaCl, pH 5.0; 20 mM sodium citrate-1 M sodium chloride, pH 5.0; and 20 mM sodium citrate, pH 5.0, sequentially). Then the antibody of interest was captured and isolated by 20 mM sodium citrate solution at pH 3.0. Finally, the antibody of interest was exchanged into 1×PBS buffer at pH 7.4 by Ultrafiltration and Diafiltration.

The purified 6 IgG antibodies (11446, 11452, 11454, 11455, 11471, and 11487) were tested for their in vitro binding activity to the human LAG-3-6*His tag recombinant fusion protein antigen by the ELISA method. The test involved a commercial human LAG-3-6*His tag fusion protein (Novoprotein corporation, Cat #CJ91). Specifically, the human LAG-3-6*His tag fusion protein was diluted with coating buffer (carbonate buffer) to a concentration of 1 µg/ml, and coated in a 96-well plate (CORNING, Cat #9018) at 4° C. over night. After washing three times with 1×PBS buffer at pH 7.4, the plate was blocked with 5% skim milk for 2 h. The 6 purified IgG antibodies were subjected to 3-fold gradient dilution starting from 100 µg/ml with 1×PBS buffer at pH 7.4, and co-incubated with the coated antibody at 25° C. for 2 h. The binding of the antibodies to the human LAG-3-6*His tag fusion protein antigen is then detected by using the HRP detection antibody with an anti-hIgG tag. As shown in FIG. 1 and Table 4, the clone 11452 has the best affinity to the human LAG-3-6*His tag fusion protein antigen, and is named as MV705-3 with the following amino acid sequences: the amino acid sequence of heavy chain CDR1 (HCDR1) is SYGIS (SEQ ID NO: 88), the amino acid sequence of heavy chain CDR2 (HCDR2) is WISAYNGNTNYAQKLQG (SEQ ID NO: 89), the amino acid sequence of heavy chain CDR3 (HCDR3) is DGWWELLRPDDAFDI (SEQ ID NO: 90), the amino acid sequence of light chain CDR1 (LCDR1) is SGDKLGDKYAY (SEQ ID NO: 91), the amino acid sequence of light chain CDR2 (LCDR2) is YDSDRPS (SEQ ID NO: 92), and the amino acid sequence of light chain CDR3 (LCDR3) is QVWDSSSDQVV (SEQ ID NO: 93).

TABLE 4

The in vitro binding activity of the IgG4 monoclonal antibodies to the human LAG-3-6*His tag fusion protein

| Test Articles | EC50 (µg/ml) |
| --- | --- |
| 11446 | 85.6 |
| 11452 | 0.364 |
| 11471 | 22.3 |
| 11487 | 3.35 |
| 11455 | 83.1 |
| 11454 | 85.8 |

Example 2. Preparation of MV705-3 LAG-3 Monoclonal Antibody from the Transfected ExpiCHO-S Cells The recombinant plasmids comprising the heavy chain and light chain genes of the preferred clone MV705-3 were transiently transfected into the suspension-cultured (on a relatively large scale (200-600 ml)) ExpiCHO-S cells (Thermo Fisher, Cat #A29127) by the liposome method with the ExpiFectamine™ CHO Transfection Kit (Thermo Fisher, Cat #A29129). The methods of transfection, culture, and purification are as described in Example 1.3. The antibody of interest was prepared. Finally, the antibody of interest was exchanged into 1×PBS buffer at pH 7.4 by Ultrafiltration and Diafiltration, for the subsequent in vitro and in vivo activity detection and bioassay experiments.

Example 3. Purity Analysis of the Transiently Expressed and Purified MV705-3 Antibody 3.1. Capillary Electrophoresis (CE) Analysis of the Purity of the LAG-3 Monoclonal Antibody MV705-3 Obtained in Example 2.

The monoclonal antibody MV705-3 samples were subjected to the reduced and non-reduced treatments by using the SDS-MW Analysis kit (Beijing Bosiya Biochemical Technology Research Institute, Cat #BSYK018), the procedures are as follows.

Non-reduced treatment: 100 µg of anti-human LAG-3 full human monoclonal MV705-3 antibody sample was added to 75 µl of 1% SDS buffer, making up to 95 µl with 0.1 M Tris-HCl. Then 5 µl of iodoacetamide was added. After mixing well by vortex, the solution was incubated at 70° C. for 5 min, and centrifuged at 6,000 g for 1 min at 8° C.

Reduced treatment: 100 µg of anti-human LAG-3 full human monoclonal MV705-3 antibody sample was added to 75 µl of 1% SDS buffer, making up to 95 µl with 0.1 M Tris-HCl. Then 5 µl of β-mercaptoethanol was added. After vortexing, the solution was incubated at 70° C. for 5 min, and centrifuged at 6,000 g for 1 min at 8° C.

Purity analysis was then carried out by a capillary electrophoresis apparatus (Beckman, model: PA800 plus). The results show that under the reduced (R-CE-SDS) and non-reduced (NR-CE-SDS) conditions, the samples of the anti-human LAG-3 full human monoclonal MV705-3 antibody expressed and purified after transiently transfecting the ExpiCHO-S cells in the present invention were performed for purity analysis shown as the peak percentages of the heavy chain (HC), light chain (LC) and main peak, in Table 5.

TABLE 5

Purity percentages of the heavy chain, light chain and main peak of the MV705-3 monoclonal antibody

| MV705-3 | LC purity % | HC purity % | Main peak purity % |
| --- | --- | --- | --- |
| NR-CE-SDS | NA | NA | 83.6% |
| R-CE-SDS | 32.4% | 66.7% | 99.1% (LC + HC purity) |

3.2. Size Exclusion Chromatography (SEC) Analysis of the Purity of the LAG-3 Monoclonal Antibody MV705-3 Obtained in Example 2.

Figure 2:
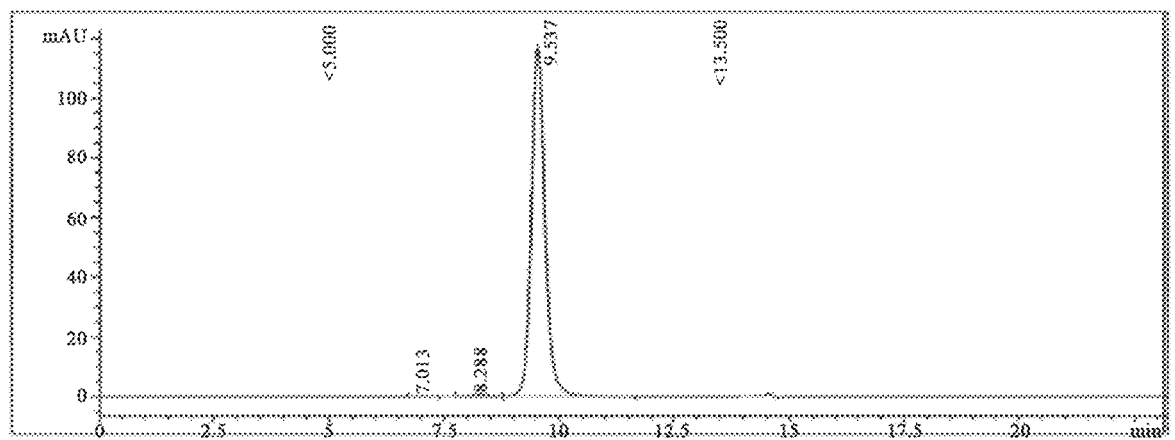
FIG. 2 shows the purity of the MV705-3 monoclonal antibody expressed and purified after transiently transfecting the ExpiCHO-S, as detected by SEC-HPLC.

20 µg of anti-human LAG-3 full human monoclonal MV705-3 antibody (with a concentration adjusted to 1 mg/ml) was loaded onto the chromatographic column (TOSOH, model: TSKgel G3000 SWXL) in a HPLC chromatographic instrument (Agilent Technologies) (mobile phase: 50 mM phosphate buffer, 300 mM sodium chloride, pH 7.0; flow rate: 0.8 ml/min; and detection wavelength: 280 nm). The results are shown in FIG. 2. Peak calculations were performed and analyzed using ChemStation software. The percentage of the main peak of the anti-human LAG-3 full human monoclonal MV705-3 antibody of the present invention was >99.2%, and the percentage of the multimer peak was <1%.

Figure 3:
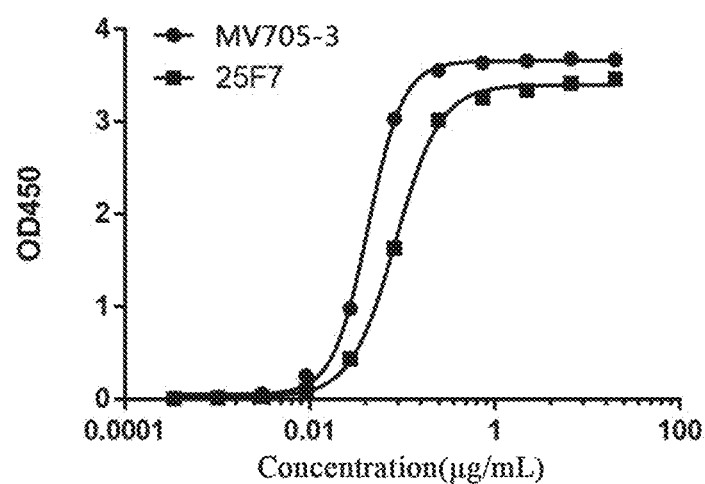
FIG. 3 shows the results of the ELISA assay for the binding of the MV705-3 monoclonal antibody to the human LAG-3-6*His tag recombinant fusion protein.

Example 4. Binding of the MV705-3 Monoclonal Antibody to the Human LAG-3-6*His Tag Recombinant Fusion Protein 4.1. Detection of the Affinity of the MV705-3 Monoclonal Antibody to the Human LAG-3-6*His Tag Recombinant Fusion Protein by ELISA Method This example involves testing the binding affinity of the MV705-3 monoclonal antibody to the human LAG-3-6*His tag recombinant fusion protein antigen by using an in vitro activity experiment. A commercially available human LAG-3-6*His tag fusion protein (Novoprotein corporation, Cat #CJ91) and a positive control antibody (i.e., antibody 25F7 (US 2011/0150892 A1, PCT/US 2009/053405)) are used in this experiment. The heavy chain nucleotide sequence, heavy chain amino acid sequence, light chain nucleotide sequence, and light chain amino acid sequence of the positive control antibody are: SEQ ID NO: 64, SEQ ID NO: 65, SEQ ID NO: 66, and SEQ ID NO: 67, respectively. The method for constructing the IgG4 kappa vector can refer to Example 1.2. The ExpiCHO-S cells were transfected by the method as described in Example 1.3 for the antibody expression and purification, and the antibody was stored in 1×PBS buffer at pH 7.4. The anti-human LAG-3 full human monoclonal antibody MV705-3 and the positive control antibody were respectively diluted with coating buffer (carbonate buffer) to a concentration of 1 μg/ml, and coated in a 96-well plate (CORNING, Cat #9018) at 4° C. over night. After washing three times with 1×PBS buffer at pH 7.4, the plate was blocked with 5% skim milk for 2 h. The human LAG-3-6*His tag fusion protein was subjected to 3-fold gradient dilution starting from 20 μg/ml with 1×PBS buffer at pH 7.4, and co-incubated with the coating antibody at 25° C. for 2 h. The binding of the antibodies to the human LAG-3-6*His tag fusion protein antigen is then detected using the HRP detection antibody with anti-His tag activity. The results of a single ELISA experiment are shown in FIG. 3. The MV705-3 monoclonal antibody has higher affinity to the human LAG-3 recombinant fusion protein, with an EC50 value of 40 ng/ml human LAG-3-6*His tag fusion protein antigen detection by ELISA. Table 6 summarizes the range of EC50 values (40-100 ng/ml) for the binding activity of the MV705-3 monoclonal antibody to the human LAG-3-6*His tag recombinant fusion protein in three independent ELISA experiments.

TABLE 6

The binding activity of the MV705-3 monoclonal antibody to the human LAG-3 recombinant fusion protein

| Test Articles | EC50 (μg/ml) |
|---|---|
| MV705-3 | 0.04-0.10 |
| Antibody 25F7 | 0.08-0.14 |

4.2. ForteBio Detection of Affinity Equilibrium Dissociation Constant KD of the MV705-3 Monoclonal Antibody The ability of the MV705-3 monoclonal antibody for binding to the human LAG-3-6*His tag recombinant fusion protein was detected using the Octet Red96 Biomolecular Interaction System (Octet Red96, ForteBio). The kinetic-grade biosensor (Fortebio, Cat #18-5063) of the anti-human IgG Fc (AHC) was pre-treated with glycine at pH 1.7, and then soaked in the detection PBS buffer. The MV705-3 was immobilized to the AHC biosensor at a concentration of 10 μg/ml. The AHC biosensor loaded with MV705-3 was then immersed in the human LAG-3-6*His antigen at different concentrations and the buffer. The last dilution point of the analyte column comprises only the detection buffer to test for non-specific binding between the buffer and the loaded biosensor. The binding of the antigen to the antibody was detected from 0 to 300 seconds, and then the dissociation occurred from 300 to 900 seconds. A 60-second baseline was determined with the detection buffer. The affinity curve for anti-LAG-3 monoclonal antibodies was fitted by a kinetic sensing monovalence binding model at a 1:1 binding. The binding kinetic analysis is shown in Table 7.

TABLE 7

Affinity of the human LAG-3-6*His tag recombinant fusion protein and the MV705-3

| The loading concentration (nM) of test samples | KD (M) | Kon (1/Ms) | Kdis (1/s) | Full X^2 | Full R^2 |
|---|---|---|---|---|---|
| 1000 | 1.795E−9 | 5.928E+04 | 1.064E−04 | 2.5950 | 0.9689 |
| 500 | 2.495E−9 | 3.988E+04 | 9.952E−05 | 0.9091 | 0.9955 |
| 250 | <1.00E−12 | 1.377E+04 | <1.0E−07 | 0.8298 | 0.9944 |

4.3. BIAcore Detection of the Affinity Equilibrium Dissociation Constant KD of the MV705-3 Monoclonal Antibody This example uses the BIAcore SPR technique to examine the binding of the MV705-3 monoclonal antibody or the positive control antibody described above to the human LAG-3-6*His tag recombinant fusion protein. The monoclonal antibody MV705-3 (1.1 μg/ml) or the positive control antibody (12.9 μg/ml) was set to a level of 500 RU, and coated on a CM5 chip (GE, Cat No.: BR100530) based on the standard immobilization operation procedure recommended by the manufacturer. Different concentrations (0.352 to 45 nM) of the human LAG-3-6*His tag recombinant fusion protein were injected on the surface of the chip coupled with the antibody at a flow rate of 30 μl/min and analyzed for 120 seconds, respectively. The antigen was allowed to dissociate for 10 minutes. After the dissociation of the antigen binding was complete, the surface of the chip was regenerated for 30 seconds with a Gly-HCl regenerating solution at pH 2.1 at a flow rate of 30 μl/min, and the chip was further recovered by washing it with the PBS buffer for 60 seconds to stabilize the chip state. All experiments were performed on a BIAcore T200 (No. 1602831) surface plasmon resonator using BIAcore control software (version 2.0.1). Data analysis was performed by BiaEvaluation software version 3.0. The analysis of the binding kinetics is shown in Table 8. The MV705-3 monoclonal antibody has higher KD of binding to the human LAG-3-6*His tag recombinant fusion protein than that of the positive control antibody 25F7.

TABLE 8

Binding kinetics of the anti-LAG-3 antibody to the human LAG-3-6*His tag recombinant fusion protein

| Test Articles | KD (M) | Kon (1/Ms) | Kdis (1/s) |
|---|---|---|---|
| Antibody 25F7 | 3.56E−10 | 4.808E+6 | 0.001712 |
| MV705-3 | 8.51E−12 | 1.078E+5 | 9.176E−7 |

Example 5. Blocking Effect of the MV705-3 on the Binding of the Human LAG-3-mFc Recombinant Fusion Protein to the MHC Class II Molecule An in vitro binding activity test is carried out in this example. The test can illustrate the blocking effect of the anti-human LAG-3 full human monoclonal antibody MV705-3 on the binding of the human LAG-3-mFc recombinant fusion protein to the MHC class II molecule. This test utilized the human LAG-3-mFc recombinant fusion protein and Daudi cells expressing the human MHC class II molecule on the surface; the human LAG-3-mFc fusion protein (hLAG-3-mFc) is formed by fusing a human LAG-3 extracellular domain with a mouse Fc, and the human LAG-3-mFc has a nucleotide sequence as shown in SEQ ID NO: 68, and an amino acid sequence as shown in SEQ ID NO: 69. The nucleotide sequence expressing the LAG-3-mFc fusion protein was cloned into the expression vector pcDNA3.3, and then transfected into the Expi293 cells (Thermo Fisher, Cat No. A14527). The above hLAG-3-mFc recombinant fusion protein was obtained after purification via a method similar to that of Example 1.3. The sequence #10161 was constructed into the expression vector pcDNA3.3, and then transfected into Expi293 cells as an isotype control. It was obtained after expression and purification. Both the positive control antibody 25F7 (as described in Example 4) and this isotype control protein were tested in this in vitro binding activity test To test the blocking effect of the antibody on the binding of the human LAG-3-mFc recombinant fusion protein to the MHC class II molecule, the MV705-3, positive control antibody 25F7 and isotype control protein were subjected to 3-fold gradient dilution starting from 100 μg/ml with 1×PBS buffer pre-cooled at 4° C. Simultaneously, 10 μg/ml of hLAG-3-mFc recombinant fusion protein solution was added to each gradient dilution. The mixture was incubated for 30 min at 4° C. Then 2×10⁵ Daudi cells washed with 1×PBS buffer pre-cooled at 4° C. were added, and then incubated for 1 h at 4° C. Subsequently, washing was performed once with 1×PBS buffer pre-cooled at 4° C. The PE-labelled rabbit anti-mouse IgG antibody (Abcam, Cat #ab7000) was incubated with the washed Daudi cells for 1 h. The binding of the hLAG-3-mFc recombinant protein to the Daudi cells was analyzed using the Guava easyCyte HT flow cytometer (MERCK MILLIPORE).

Figure 4:
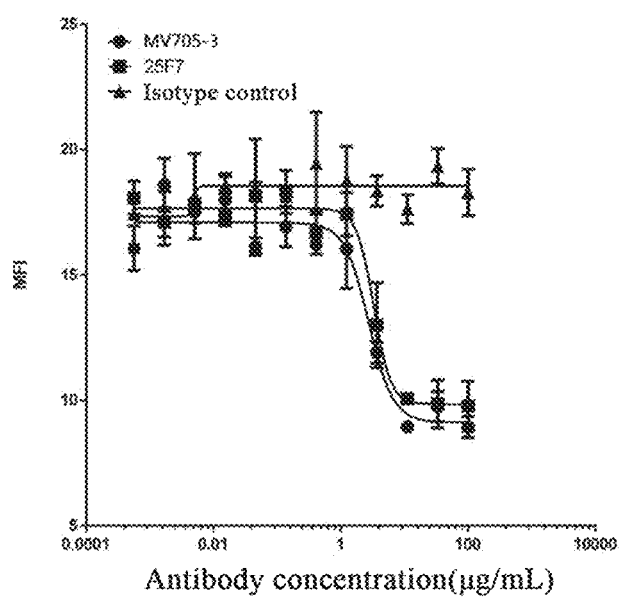
FIG. 4 shows the blocking effect of an anti-human LAG-3 full human monoclonal antibody on the binding of a human LAG-3-mFc recombinant fusion protein to a MHC class II molecule.

As shown in the results of FIG. 4 and Table 9, the monoclonal antibody MV705-3 is able to effectively block the binding of the human LAG-3-mFc recombinant fusion protein to the MHC class II molecule on the surface of the Daudi cells, with an IC50 value of 2.8 μg/ml for the blocking; this is comparable with the ability of the positive control antibody 25F7 to block the binding of the human LAG-3-mFc to the MHC class II molecule on the surface of the Daudi cells. The positive control antibody 25F7 has an IC50 value of 3.3 μg/ml for the blocking.

TABLE 9

Blocking effect of the MV705-3 on the binding of the human LAG-3-mFc to the MHC class II molecule

| Test Articles | IC50 (μg/ml) |
|---|---|
| MV705-3 | 2.8 |
| Antibody 25F7 | 3.3 |
| Isotype control | NA |

Example 6. Binding Activity of the MV705-3 to a *Macaca fascicularis* LAG-3 Antigen and a Mouse LAG-3 Antigen An in vitro activity test was carried out in this example to illustrate whether the antibody cross-reacts with a *Macaca fascicularis* LAG-3 antigen and a mouse LAG-3 antigen. The test involved a commercially available recombinant *Macaca fascicularis* LAG-3-6*His tag fusion protein (Novoprotein corporation, Cat #C998) and a recombinant mouse LAG-3-6*His tag fusion protein expressed by construction. The full-length cDNA of the mouse LAG-3 gene (Sinobiological, Cat #MG53069-G) was cloned into the expression vector pcDNA3.3, then transfected into the Expi293 cells and thereby obtaining the above described recombinant mouse LAG-3-6*His tag fusion protein (with a nucleotide sequence of SEQ ID NO: 70, and an amino acid sequence of SEQ ID NO: 71).

To test the cross-reactivity of the antibody with the *Macaca fascicularis* LAG-3 antigen, the anti-human LAG-3 full human monoclonal antibody MV705-3 and the positive control antibody 25F7 were respectively diluted with coating buffer (carbonate buffer) to a concentration of 1 μg/ml, and coated in a 96-well plate (CORNING, Cat #9018) at 4° C. over night. After washing three times with 1×PBS buffer, the plate was blocked with 5% skim milk for 2 h. The *Macaca fascicularis* LAG-3-6*His tag fusion protein was subjected to 3-fold gradient dilution starting from 20 μg/ml with 1×PBS buffer, and co-incubated with the coating antibody at 25° C. for 2 h. The binding of the antibodies to the *Macaca fascicularis* LAG-3-6*His tag fusion protein antigen is then detected by the HRP detection antibody with anti-His tag activity.

Figure 5:
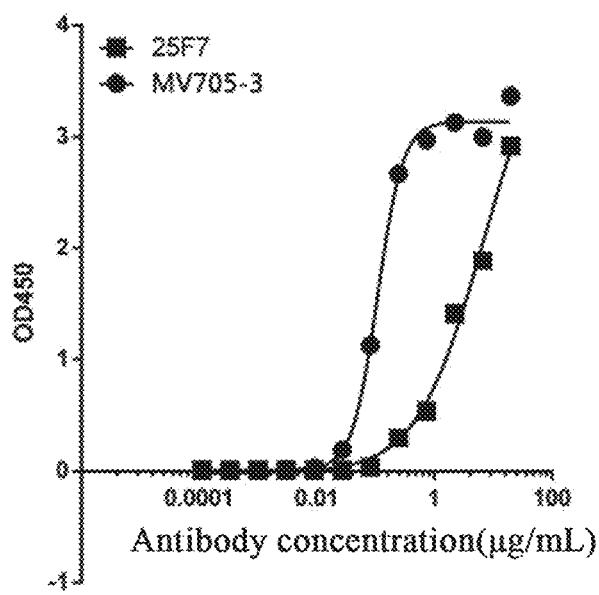
FIG. 5 shows the cross-binding activity of the anti-human LAG-3 full human monoclonal antibody to a *Macaca fascicularis* LAG-3*6His tag fusion protein antigen.

Results are shown in FIG. 5 and Table 10, the monoclonal antibody MV705-3 has a good cross-reactivity with the *Macaca fascicularis* LAG-3-6*His tag fusion protein with an EC50 value of 0.11 μg/ml; the positive control antibody 25F7 has weak cross-reactivity with the *Macaca fascicularis* LAG-3-6*His tag fusion protein with the corresponding EC50 value of 7.0 μg/ml.

TABLE 10

Cross-reactivity of the MV705-3 with the *Macaca fascicularis* LAG-3 antigen

| Test Articles | EC50 (μg/ml) |
|---|---|
| MV705-3 | 0.11 |
| Antibody 25F7 | 7.0 |

Figure 6:
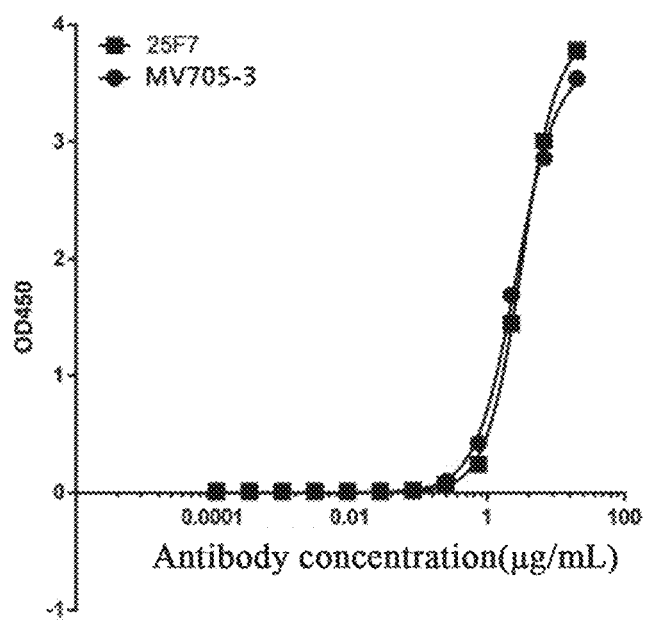
FIG. 6 shows the cross-reactivity of the anti-human LAG-3 full human monoclonal antibody with a mouse LAG-3 antigen.

To test the cross-reactivity of the antibody with the mouse LAG-3 antigen, the binding activity of the antibody MV705-3 to the mouse LAG-3-6*His tag fusion protein antigen was detected by the method described above. Results are shown in FIG. 6 and Table 11, both the antibody MV705-3 and the positive control antibody 25F7 have weak cross-reactivity to the mouse LAG-3 antigen.

TABLE 11

Cross-reactivity of the MV705-3 with the mouse LAG-3 antigen

| Test Articles | EC50 (μg/ml) |
|---|---|
| MV705-3 | 2.6 |
| Antibody 25F7 | 3.2 |

Figure 7:
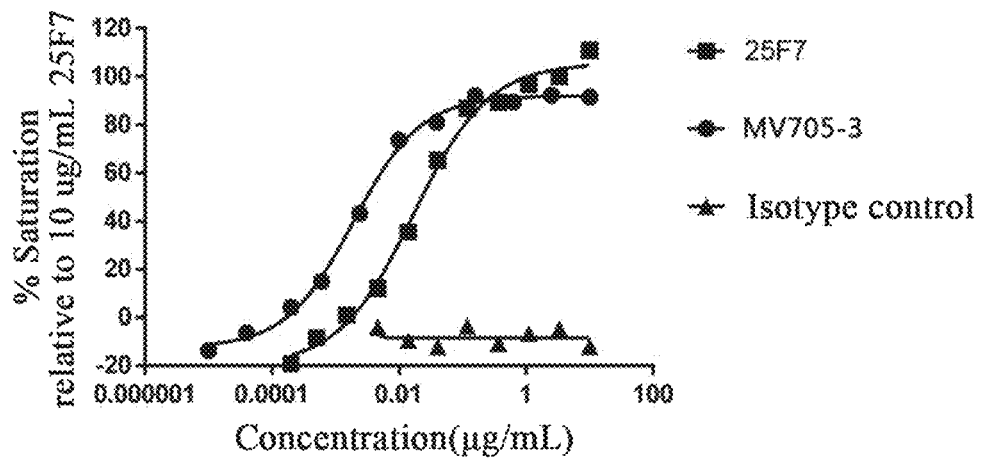
FIG. 7 shows the binding activity of the anti-human LAG-3 full human monoclonal antibody to the activated human $CD4^+$ T cells.

Example 7. Binding Activity of the MV705-3 to the Activated Human CD4⁺ T Cells An in vitro binding activity test was carried out in this example, intending to test binding activity of the antibody to the activated human CD4⁺ T cells which express the native human LAG-3 on their surface. The CD4⁺ T cells were activated using the method in Example 1.2. Then the antibody MV705-3, the positive control antibody 25F7, and the above negative control (the isotype control) were subjected to a 3-fold or 4-fold gradient dilution starting from 10 μg/ml with cold 1×PBS buffer (Hyclone, Cat #SH30256.01). For the binding activity detection, the binding of the antibodies to the CD4⁺ T cells was detected using a PE-labelled goat anti-human antibody (Abcam, Cat #ab98596) diluted at 1:200. The binding activity of the antibodies to the cells was analyzed using Guava easyCyte HT flow cytometer (MERCK MILLIPORE). In the flow cytometry analysis, gating is used to select the CD4 positive T cells expressing LAG-3. Results are shown in FIG. 7 and Table 12. The MV705-3 monoclonal antibody is able to bind to the CD4 positive T cells expressing the LAG-3 with high affinity, and with an EC50 value of 1.9 ng/ml for the binding.

TABLE 12

Binding activity of the MV705-3 to the activated human CD4⁺ T cells

| Test Articles | EC50 (ng/ml) |
|---|---|
| MV705-3 | 1.9 |
| Antibody 25F7 | 16.8 |

Example 8. In Vitro Biological Function Analysis of the MV705-3

An in vitro biological function analysis was carried out in this example. This test utilized a commercially available cell line LAG3/NFAT Reporter-Jurkat stably expressing the human LAG-3 (BPS bioscience, Cat #71278), Raji cells (ATCC, Cat #CCL-86), a superantigen reagent (Toxin technology-ET404), and a bio-glo luciferase reagent (Promega, Cat. No. G7940).

To test the in vitro T cell activation biological function of the antibody, the antibody MV705-3 and the positive control antibody 25F7 were subjected to a 3-fold gradient dilution starting from 150 μg/ml (5×final concentration) with RPIM1640 (Gibco, Cat. No. 11875093) in triplicate wells. A blank control was set. The antibodies at each dilution gradient were respectively mixed with the LAG3/NFAT Reporter-Jurkat cells at 4×10⁴ cells/well, and pre-incubated for 30 minutes in 5% CO₂ incubator at 37° C. Subsequently, the Raji cells at 3×10⁴ cells/well and 10 μl of a superantigen reagent at a concentration of 0.08 ng/ml (10×final concentration) were sequentially added. The mixture was co-incubated for 5-6 hours in 5% CO₂ incubator at 37° C. 100 μl of bio-glo luciferase detection reagent was quickly added and incubated for 5-10 minutes, and the signal of biofluorescence was measured by a TECAN fluorescence detection instrument (TECAN infinite M1000 PRO), to analyze the in vitro T cell activation function of the antibody. The induction fold was determined as the ratio of the biofluorescence signal value of each concentration gradient to the biofluorescence signal value of the blank control. The experimental data was used nonlinear regression analysis with GraphPad Prism Software.

Figure 8:
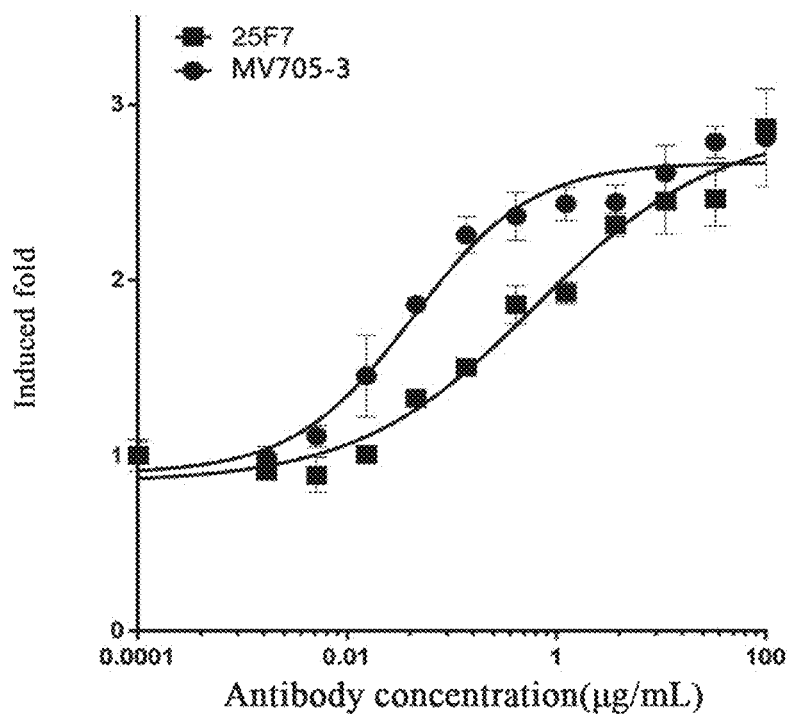
FIG. 8 shows the in vitro biofunctional analysis of the anti-human LAG-3 full human monoclonal antibody.

The results are shown in FIG. 8 and Table 13. With the increase of the concentration of the antibody MV705-3, the signal intensity of biofluorescence increases in a gradient-dependent manner, indicating that the antibody MV705-3 can increase the expression of the NFAT reporter gene, with an EC50 value of 0.04 μg/ml. The antibody MV705-3 clearly showed an in vitro T cell activation biological function superior to the positive control antibody 25F7 which has an EC50 value of 0.64 μg/ml.

TABLE 13

The ability of the MV705-3 to activate T cells in vitro

| Test Articles | EC50 (μg/ml) |
|---|---|
| MV705-3 | 0.04 |
| Antibody 25F7 | 0.64 |

Figure 9:
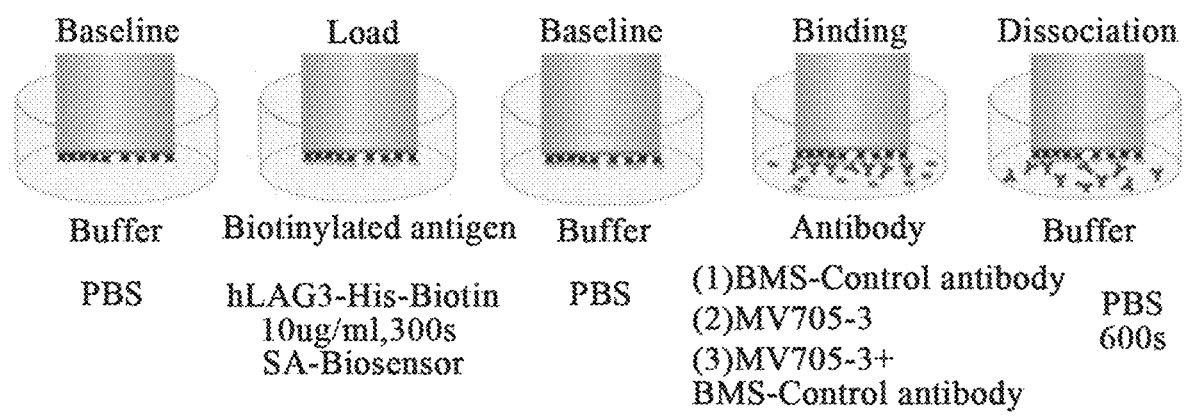
FIG. 9 shows the experimental design of the binding epitope analysis of the MV705-3 and BMS control monoclonal antibodies (BMS-25F7 and BMS-986016).
Figure 10A:
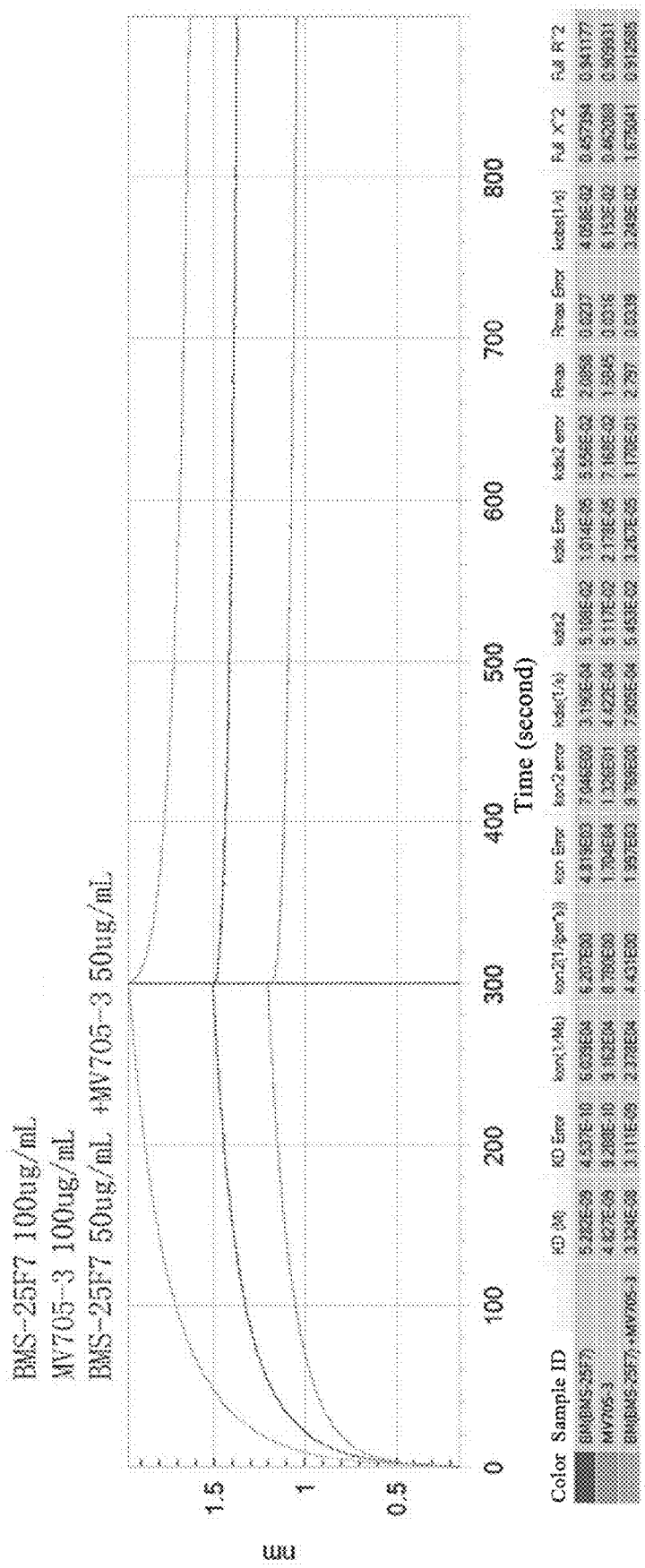
FIGS. 10a-10d show the results of binding epitope analysis of the MV705-3 and the BMS control monoclonal antibodies (BMS-25F7 and BMS-986016).
Figure 10B:
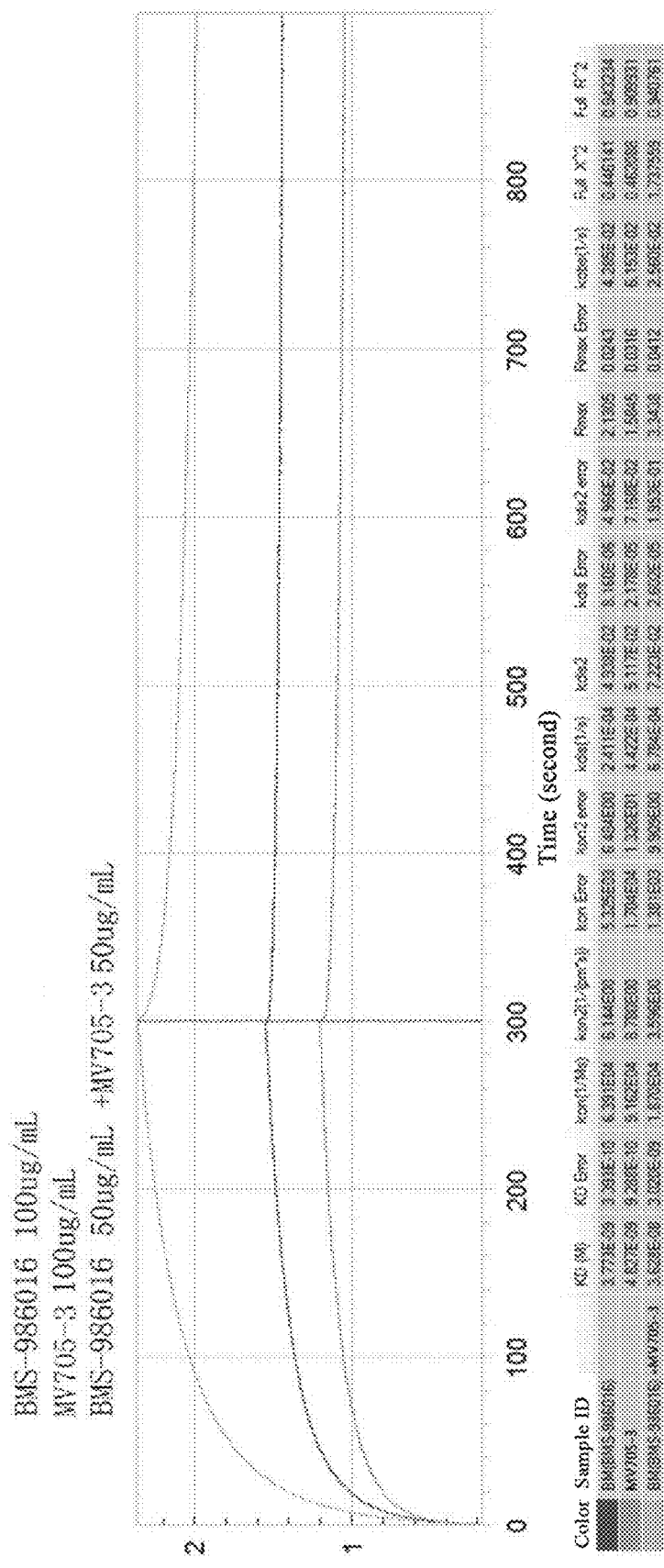
Figure 10C:
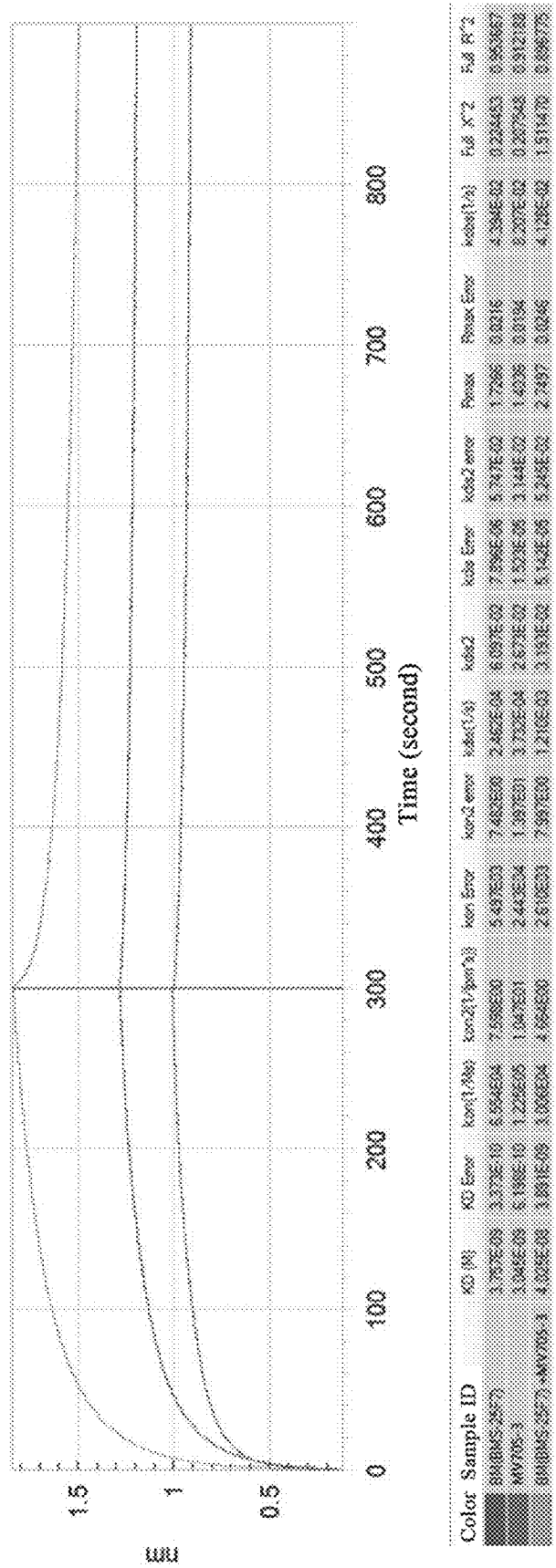
Figure 10D:
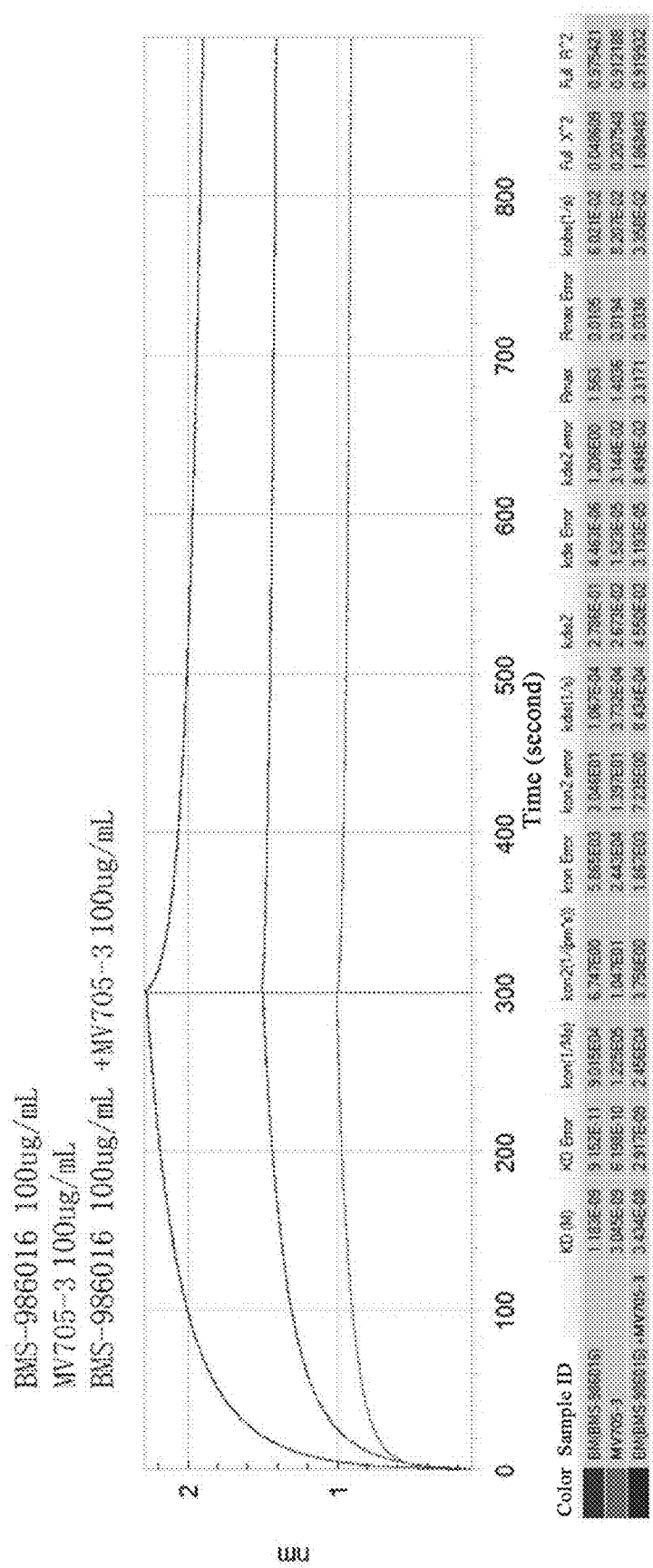

Example 9. Binding Epitope Analysis of the MV705-3, the BMS-25F7 Antibody and the BMS-986016 Antibody This example is intended to analyze whether the MV705-3 monoclonal antibody has the same binding epitope with the BMS-25F7 antibody (disclosed in the literatures, for example, US 2011/0150892 A1 and PCT/US 2009/053405, which are incorporated herein by reference), or the BMS-986016 antibody (which comprises the heavy chain and light chain respectively represented by SEQ ID NOs: 1 and 2 as described in WO 2015116539, also described in WO 2014/008218, which are incorporated herein by reference). The experiment is characterized by the Octet Red96 Biomolecular Interaction System (Octet Red96, ForteBio). The experimental design is shown in FIG. 9, the procedures are briefly described as follows: biotin-labelled hLAG-3-6*his tag recombinant protein at a concentration of 10 μg/ml was immobilized to the SA biosensor (Fortebio, Cat. No. 18-5020), immersing in a PBS buffer after equilibration for 300 seconds, then the SA biosensor loaded with the hLAG-3-6*his tag recombinant protein was immersed in the following samples of each group: (1) 100 μg/ml of the BMS control monoclonal antibody (BMS-25F7, or BMS-986016); (2) 100 μg/ml of the MV705-3 monoclonal antibody; (3) a mixture of 100 μg/ml of the MV705-3 monoclonal antibody and 100 μg/ml of the BMS control monoclonal antibody BMS-25F7 or BMS-986016; (4) a mixture of 50 μg/ml of the MV705-3 monoclonal antibody and 50 μg/ml of the BMS control monoclonal antibody BMS-25F7 or BMS-986016. A 60-second baseline was determined with the PBS buffer. The binding of the antigen to the antibody was detected from 0 to 300 seconds, and then the dissociation occurred from 300 to 900 seconds. The affinity curve for anti-LAG-3 monoclonal antibodies was fitted with a kinetic sensing monovalence binding model at a 1:2 binding ratio. The mixtures of the two antibodies were able to increase the signal value of the binding to the hLAG-3-his tag recombinant protein at a concentration of 100 μg/ml+100 μg/ml or 50 μg/ml+50 μg/ml, indicating that the MV705-3 monoclonal antibody and the BMS control antibody bind to different epitopes of the hLAG-3 antigen.

Example 10. Design, Construction and Expression, and Activity Testing of Variants of the MV705-3 Monoclonal Antibody

10.1 Design, Construction and Expression of Variants of the MV705-3 Monoclonal Antibody There are two sites revealed in the heavy chain of the antibody comprising a "DD" amino acid sequence by digging potential degradation sites in the amino acid sequence of the MV705-3 monoclonal antibody. The two sites are potential recognition sites for the isomerization of asparagine, and located at the positions 89 and 90 and positions 108 and 109 of SEQ ID NO: 41, respectively. Site-directed mutagenesis at positions 89 and 90 and positions 108 and 109 in the VH region of the MV705-3 monoclonal antibody was performed by using the Q5® Site-Directed Mutagenesis Kit (New England Biolabs, Cat. No. E0552S), to change the amino acid residues into DE or ED. The variant VH region of the mutagenized MV705-3 monoclonal antibody was subcloned into the original vector of the MV705-3 monoclonal antibody comprising the human IgG4 S228P constant region (the resulting clone numbers are shown in Table 14; and the numbers of the nucleotide sequence and amino acid sequence of the heavy chain VH of the resulting clones are shown in Table 15). The vector expressing each of the variant heavy chains of the MV705-3 monoclonal antibody and the vector expressing the light chain of the MV705-3 monoclonal antibody were respectively co-transfected into the Expi-CHO-S cells.

TABLE 14

Clone comprising the optimized variant heavy chain of the MV705-3 monoclonal antibody

| Clone information | Clone numbers |
|---|---|
| MV705-3-VH-DD + DE-IgG4 | 13365 |
| MV705-3-VH-DE + DD-IgG4 | 13380 |
| MV705-3-VH-ED + DD-IgG4 | 13381 |
| MV705-3-VH-DD + ED-IgG4 | 13386 |
| MV705-3-VH-DE + ED-IgG4 | 13563 |
| MV705-3-VH-ED + DE-IgG4 | 13564 |
| MV705-3-VH-DE + DE-IgG4 | 13565 |
| MV705-3-VH-ED + ED-IgG4 | 13616 |

TABLE 15

The nucleotide sequences and amino acid sequences of the variant heavy chains

| Description | Sequence numbers |
|---|---|
| 13365-MV705-3-VH-DD + DE The nucleotide sequence of heavy chain VH | SEQ ID NO: 72 |
| 13365-MV705-3-VH-DD + DE The amino acid sequence of heavy chain VH | SEQ ID NO: 73 |
| 13380-MV705-3-VH-DE + DD The nucleotide sequence of heavy chain VH | SEQ ID NO: 74 |
| 13380-MV705-3-VH-DE + DD The amino acid sequence of heavy chain VH | SEQ ID NO: 75 |
| 13381-MV705-3-VH-ED + DD The nucleotide sequence of heavy chain VH | SEQ ID NO: 76 |
| 13381-MV705-3-VH-ED + DD The amino acid sequence of heavy chain VH | SEQ ID NO: 77 |
| 13386-MV705-3-VH-DD + ED The nucleotide sequence of heavy chain VH | SEQ ID NO: 78 |
| 13386-MV705-3-VH-DD + ED The amino acid sequence of heavy chain VH | SEQ ID NO: 79 |
| 13563-MV705-3-VH-DE + ED The nucleotide sequence of heavy chain VH | SEQ ID NO: 80 |

TABLE 15-continued

The nucleotide sequences and amino acid sequences of the variant heavy chains

| Description | Sequence numbers |
|---|---|
| 13563-MV705-3-VH-DE + ED The amino acid sequence of heavy chain VH | SEQ ID NO: 81 |
| 13564-MV705-3-VH-ED + DE The nucleotide sequence of heavy chain VH | SEQ ID NO: 82 |
| 13564-MV705-3-VH-ED + DE The amino acid sequence of heavy chain VH | SEQ ID NO: 83 |
| 13565-MV705-3-VH-DE + DE The nucleotide sequence of heavy chain VH | SEQ ID NO: 84 |
| 13565-MV705-3-VH-DE + DE The amino acid sequence of heavy chain VH | SEQ ID NO: 85 |
| 13616-MV705-3-VH-ED + ED The nucleotide sequence of heavy chain VH | SEQ ID NO: 86 |
| 13616-MV705-3-VH-ED + ED The amino acid sequence of heavy chain VH | SEQ ID NO: 87 |

The obtained eight MV705-3 monoclonal antibody variants described above and the MV705-3 monoclonal antibody were tested for activity by a variety of analytical methods as described below: (a) the ELISA of binding to the human LAG-3 recombinant protein; (b) the experiment of binding to the cells expressing the human LAG-3 protein; (c) the in vitro bioanalysis by a commercially available cell line LAG3/NFAT Reporter-Jurkat stably expressing the human LAG-3.

10.2. Testing the Activity of MV705-3 Monoclonal Antibody Variants (a) The ELISA method for the binding of MV705-3 monoclonal antibody variants to the human LAG-3 recombinant protein is as described in Example 4.

The results are shown in Table 16. Two variant proteins 13380 (DE+DD) and 13381 (ED+DD) have the similar ability to bind to the human LAG-3-his tag recombinant fusion protein as that of the MV705-3 monoclonal antibody, and the binding ability of other variants is reduced in different degrees.

TABLE 16

The results of the ELISA experiments for the binding of the variants of the MV705-3 monoclonal antibody to the human LAG-3 recombinant protein

| Test Articles | EC50 (μg/ml) |
|---|---|
| MV705-3 | 0.039 ± 0.0057 (N = 5) |
| 13380 (DE + DD) | 0.044 ± 0.0091 (N = 3) |
| 13381 (ED + DD) | 0.044 ± 0.0067 (N = 3) |
| 13365 (DD + DE) | 1.29 |
| 13386 (DD + ED) | 0.15 |
| 13563 (DE + ED) | 0.21 |
| 13564 (ED + DE) | 2.43 |
| 13565 (DE + DE) | 3.13 |
| 13616 (ED + ED) | 0.21 ± 0.039 (N = 2) |

(b) The experimental methods for the binding of the variants of the MV705-3 monoclonal antibody to the cells expressing the human LAG-3 are briefly described as follows:

The test antibody MV705-3 monoclonal antibody and variants thereof, the positive control antibodies (BMS-25F7 and BMS-986016 antibodies) were subjected to a 3-fold or 4-fold gradient dilution starting from 10 μg/ml in cold 1×PBS buffer (Hyclone, Cat #SH30256.01). For the binding activity detection, the binding of the antibody to the cells expressing the human LAG-3 was detected using a PE-labelled goat anti-human IgG antibody (Abcam, Cat #ab98596) diluted at 1:200. The binding activity of the antibody to the cells was analyzed using Guava easyCyte HT flow cytometer (MERCK MILLIPORE). In the flow cytometry analysis, gating is set to select the positive cells expressing the LAG-3. The results are shown in Table 17. Similar to the ELISA results, The two variants 13380 (DE+DD) and 13381 (ED+DD) have similar binding ability to the cells expressing the human LAG-3 as that of the MV705-3 monoclonal antibody protein. The binding ability of other variants is decreased to some extent.

TABLE 17

The binding ability of the variants of the MV705-3 monoclonal antibody to the cells expressing the human LAG-3

| Test Articles | EC50 (ng/ml) |
|---|---|
| BMS-25F7 | 39 ± 12 (N = 4) |
| BMS-986016 | 69 ± 56 (N = 3) |
| MV705-3(DD + DD) | 2.3 ± 0.9 (N = 4) |
| 13380 (DE + DD) | 1.8 ± 0.5 (N = 4) |
| 13381 (ED + DD) | 2.2 ± 0.6 (N = 4) |
| 13386 (DD + ED) | 5.9 ± 3.5 (N = 4) |
| 13563 (DE + ED) | 4.7 ± 0.8 (N = 4) |
| 13616 (ED + ED) | 5.1 ± 3 (N = 2) |
| 13365 (DD + DE) | >10 (N = 1) |
| 13565 (DE + DE) | >10 (N = 2) |
| 13564 (ED + DE) | >10 (N = 1) |

(c) The in vitro bioanalysis using the commercially available cell line LAG3/NFAT Reporter-Jurkat stably expressing the human LAG-3 is as described in Example 8. It is known that the binding ability of the MV705-3 variant clones 13365 (DD+DE), 13565 (DE+DE) and 13564 (ED+DE) to the LAG-3 is greatly decreased. Therefore, only the MV705-3 monoclonal antibody and the following 5 variants were tested: 13380 (DE+DD); 13381 (ED+DD); 13386 (DD+ED); 13563 (DE+ED) and 13616 (ED+ED). Results are as shown in Table 18. The variants 13380 (DE+DD) and 13381 (ED+DD) have the similar activity to activate T cells in vitro as that of the MV705-3 monoclonal antibody.

TABLE 18

Ability of the MV705-3 monoclonal antibody and its five variants to activate T cells in vitro

| Test Articles | EC50 (µg/ml) |
|---|---|
| MV705-3 | 0.13 ± 0.036 (n = 5) |
| 13380(DE + DD) | 0.05 ± 0.03 (n = 2) |
| 13381(ED + DD) | 0.1 ± 0.059 (n = 2) |
| 13386(DD + ED) | >30 (n = 1) |
| 13563(DE + ED) | >30 (n = 1) |
| 13616(ED + ED) | >30 (n = 1) |

Example 11. Efficacy of the 13381 Variant in Inhibiting the Tumor Cell Growth In Vivo In order to test the efficacy of the 13381 variant of the MV705-3 monoclonal antibody in inhibiting the growth of tumor cell in vivo, the mice (purchased from Southern Model Biotechnology Co., Ltd.; the full name of the strain: B6.129-Lag3tm(hLAG3)/Smoc; Cat #NM-KI-00049) with the humanized LAG-3 were used. The sequence of the extracellular region of the mouse endogenous LAG3 gene was completely replaced with the human LAG3 sequence by homologous recombination in the mice, thereby allowing the mice to express the humanized chimeric LAG3 protein. The mice was inoculated with a murine MC38 colon cancer cell line to prepare a tumor transplantation model.

The above humanized LAG-3 mice (B6.129-Lag3tm (hLAG3)/Smoc) were each implanted with $1 \times 10^6$ MC38 cells on day 0, and were grouped for dosing when the tumor grew to a volume of about 123 (mm$^3$) in average. Administration was performed twice a week for three consecutive weeks (BIW×3). Mean tumor volumes were observed and measured for three to four consecutive weeks from start of the administration. Animals were divided into four groups (n=8). (1) control group, treated with PBS, BIW×3, ip; (2) single drug treated, mPD-1 antibody (BE0146, BioCell), 1 mg/kg, BIW×3, ip; (3) single drug treated, the 13381 variant of the MV705-3 monoclonal antibody, 10 mg/kg, BIW×3, ip; (4) combination two drugs treated, the 13381 variant of the MV705-3 monoclonal antibody, 10 mg/kg, and mPD-1 antibody (BE0146, BioCell), 1 mg/kg, BIW×3, ip.

Figure 12:
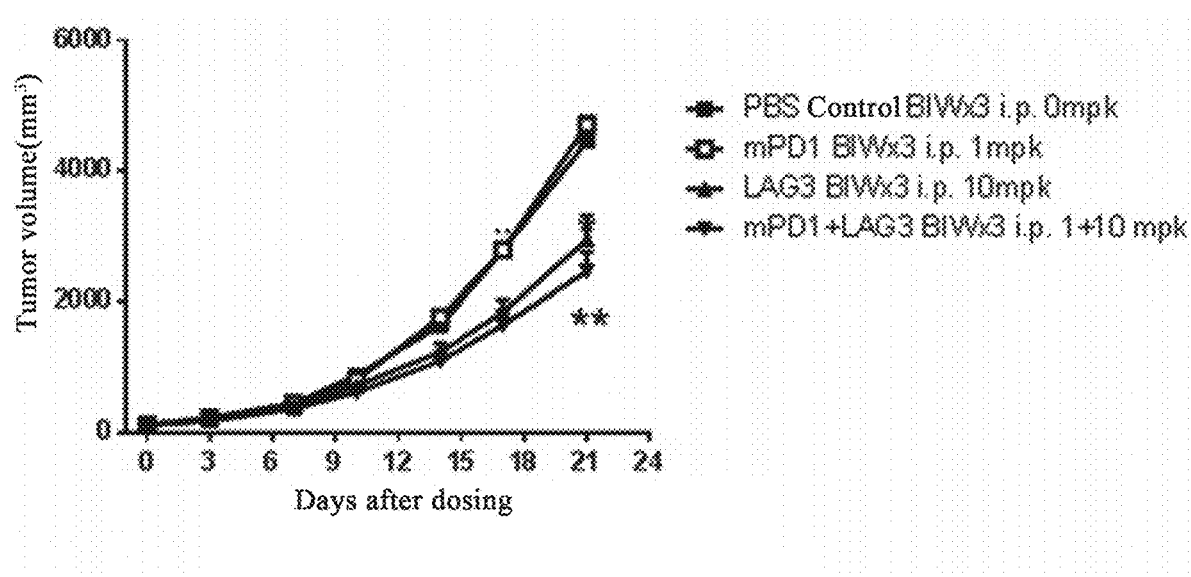
FIG. 12 shows the in vivo verification of the antitumor efficacy of the 13381 variant in the LAG3 humanized mouse MC38 tumor-bearing model. The figure shows the mean volume of the tumor±SEM. * The significance level is 0.05; ** the significance level is 0.01.

The results are shown in Table 19 and FIG. 12. tThe treatment with single 13381 variant of the MV705-3 monoclonal antibody can effectively inhibit the tumor growth, with an average tumor growth inhibition rate of 35.11%

$$\left(\text{Average tumor growth inhibition rate} = \left(1 - \frac{Ti - T0}{Vi - V0}\right) \times 100\right);$$

Ti or Vi represents the mean tumor volume of the treatment group or the control group at a specific time point; T0 or V0 represents the mean tumor volume of the treatment group or the control group after the grouping and before the administration); while the treatment with single mPD-1 antibody had no inhibitory effect on the tumor growth. The combination treatment with the 13381 variant of the MV705-3 monoclonal antibody and the mPD-1 antibody had the strongest inhibitory effect on the tumor growth, with an average tumor growth inhibition rate of 46.07%.

TABLE 19

Verification of the tumor inhibition effect of the 13381 variant of the MV705-3 monoclonal antibody in the LAG3 humanized mouse MC38 model in vivo
Average tumor growth inhibition rate for the MC38 model

| Days | PBS | mPD-1 | LAG-3 | mPD-1 + LAG-3 |
|---|---|---|---|---|
| 21 | — | −5.61% | 35.11% | 46.07% |

REFERENCES

1. Triebel F, Jitsukawa S, Baixeras E, et al. LAG-3, a novel lymphocyte activation gene closely related to CD4 [J]. J Exp Med, 1990, 171(5):1393-1405.
2. Workman C J, Dugger K J, Viganli D A, et al. Cutting edge: molecular analysis of the negative regulatory function of lymphocyte activation gene-3 W. J Immunol, 2002, 169(10):5392-5395.
3. Li N, Workman C J, Martin S M, et al. Biochemical analysis of the regulatory T cell protein lymphocyte activation gene-3 (LAG-3; CD223) J Immunol, 2004, 173(11):6806-6812.
4. Li N, Wang Y, Forbes K, et al. Metalloproteases regulate T cell proliferation and effect or function via LAG-3 W. EMBO J, 2007, 26(2):494-504.
5. Workman C J, Rice D S, Dugger K J, et al. Phenotypic analysis of the murine CD4-related glycoprotein, CD223 (LAG-3) [J]. Eur J Immunol, 2002, 32(8): 2255-2263.

6. Blackburn S D, Shin H, Haining W N, et al. Coregulation of CD8+T cell exhaustion by multiple inhibitory receptors during chronic viral infection [J]. Nat Immunol, 2009, 10(1): 29-37.
7. Workman C J, Vignali D A. Negative regulation of T cell homeostasis by lymphocyte activation gene-3 (CD223) J Immunol, 2005, 174(2): 688-695.
8. Workman C J, Wang Y, El Kasmi K C. LAG-3 regulates plasmacytoid dendritic cell homeostasis [J]. J Immunol, 2009, 182(4): 1885-1891.
9. An nunziato F, Manetti R, Tomasevic I, et al. Expression and release of LAG-3-encoded protein by human CD4 T cells are associated with IFN-gama production [J]. FASEB J, 1996, 10 (7):769-775.
10. Workman C J, Cauley L S, Kim I J, et al. Lymphocyte activation gene-3 (CD223) regulates the size of the expanding T cell population following antigen activation in vivo W. J Immunol, 2004, 172(9):5450-5455.
11. Macon-Lemaitre L, Triebel F. The negative regulatory function of the lymphocyte-activation gene-3 co-receptor (CD223) on human T cells [J]. Immunol, 2005, 115(2): 170-178.
12. Huang C T, Workman C J, Flies D, et al. Role of LAG-3 in regulatory T cells [J]. Immun, 2004, 21(4):503-513.
13. Gandhi M K, Lambley E, Duraiswamy J, et al. Expression of LAG-3 by tumor infiltrating lymphocytes is coincident with the suppression of latent membrane antigen specific CD8+T cell function in Hodgkin-lymphoma patients W. Blood, 2006, 108(7):2280-2289.
14. Andreae S, Biosson S, Triebel F, et al. MHC class II signal transduction in human dendritic cells induced by a natural ligand, the LAG-3 protein (CD223) W. Blood, 2003, 102(6):2130-2137.
15. Liang B, Workman C J, Lee J, et al. Regulatory T cells inhibit dendritic cells by lymphocyte activation gene-3 engagement of MHC class II [J]. Immunol, 2008, 180(9): 5916-5926.
16. Blackburn S D, Shin H, Nicholas Haining W. Coregulation of CD8+T cell exhaustion by multiple inhibitory receptors during chronic viral infection Pt Nat Immunol, 2009, 10(1):29-37.
17. Kassu A, Marcus RA. Receptors during Chronic HIV Infection Function by Multiple Costimulatory Regulation of Virus-Specific CD4+T Cell [J]. J Immunol, 2010, 185(5): 3007-3018.
18. Konnai S, Suzuki S, Shirai T. Enhanced expression of LAG-3 on lymphocyte subpopulations from persistently lymphocytotic cattle infected with bovine leukemia virus [J]. Comp Immunol Microbiol Infect Dis, 2013, 36(1): 63-69.

The invention claimed is:

1. An isolated anti-LAG-3 antibody comprising a heavy chain variable region and a light chain variable region, wherein the heavy chain variable region comprises:
   (a) a heavy chain variable region CDR1 comprising the sequence SYGIS (SEQ ID NO: 88);
   (b) a heavy chain variable region CDR2 comprising the sequence WISAYNGNTNYAQKLQG (SEQ ID NO: 89), and
   (c) a heavy chain variable region CDR3 comprising the sequence DGWWELLRPDDAFDI (SEQ ID NO: 90), and
   the light chain variable region comprises:
   (d) a light chain variable region CDR1 comprising the sequence SGDKLGDKYAY (SEQ ID NO: 91),
   (e) a light chain variable region CDR2 comprising the sequence YDSDRPS (SEQ ID NO: 92), and
   (f) a light chain variable region CDR3 comprising the sequence QVWDSSSDQW (SEQ ID NO: 93).

2. The antibody of claim 1, comprising a heavy chain variable region and a light chain variable region, wherein:
   (1) the heavy chain variable region comprises the amino acid sequence of SEQ ID NO: 41, and the light chain variable region comprises the amino acid sequence of SEQ ID NO: 43;
   (2) the heavy chain variable region comprises the amino acid sequence of SEQ ID NO: 75, and the light chain variable region comprises the amino acid sequence of SEQ ID NO: 43; and
   (3) the heavy chain variable region comprises the amino acid sequence of SEQ ID NO: 77, and the light chain variable region comprises the amino acid sequence of SEQ ID NO: 43.

3. The antibody of claim 1, wherein the antibody is a monoclonal antibody, a human antibody, or a chimeric antibody.

4. The antibody of claim 1, wherein the antibody is an antibody fragment binding to LAG-3.

5. The antibody of claim 4, wherein the antibody fragment is a Fab, Fab'-SH, Fv, scFv, or (Fab')$_2$ fragment.

6. The antibody of claim 1, wherein the antibody is a full length antibody.

7. The antibody of claim 1, wherein the antibody is an IgG antibody.

8. The antibody of claim 1, wherein the antibody is a monospecific antibody.

9. The antibody of claim 1, wherein the antibody is a multispecific antibody.

10. The antibody of claim 9, wherein the multispecific antibody is a bispecific antibody.

11. The antibody of claim 10, wherein the bispecific antibody comprises a second binding domain that binds to a second biomolecule, and wherein the second biomolecule is a cell surface antigen.

12. The antibody of claim 11, wherein the cell surface antigen is a tumor antigen.

13. An isolated nucleic acid encoding the antibody of claim 1.

14. The isolated nucleic acid of claim 13, wherein the antibody is an antibody fragment binding to LAG-3.

15. The isolated nucleic acid of claim 14, wherein the antibody fragment is a Fab, Fab'-SH, Fv, scFv, or (Fab')$_2$ fragment.

16. An antibody immunoconjugate comprising a therapeutic agent that is linked to the antibody of claim 5.

17. The immunoconjugate of claim 16, wherein the therapeutic agent is a cytotoxic agent.

18. A pharmaceutical composition comprising the antibody immunoconjugate of claim 16 and a pharmaceutically acceptable carrier.

19. A pharmaceutical composition comprising the antibody of claim 1 and a pharmaceutically acceptable carrier.

* * * * *

```
SEQUENCE LISTING

<160> NUMBER OF SEQ ID NOS: 93

<210> SEQ ID NO 1
<211> LENGTH: 6333
<212> TYPE: DNA
<213> ORGANISM: Artificial Sequence
<220> FEATURE:
<223> OTHER INFORMATION: synthesized sequence

<400> SEQUENCE: 1
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagcttc     240
catgaaaatt ctatttcaag gagacagtca taatgaaata cctattgcct acggcagccg     300
ctggattgtt attactcgcg gcccagccgg ccatggccta gtgataacct ggctccacac     360
tctggctgtc ctgtggggta cccctgact ctgtgtccag gggccccctc tcctggaccc     420
atgtgcaccc aagggcct aagtcattgc tgagcctaga gctgaaggac gatcgcccgg     480
ccagagatat gtgggtaatg gagacgggtc tgttgttgcc ccgggccaca gctcaagacg     540
ctggaaagta ttattgtcac cgtggcaacc tgaccatgtc attccacctg gagatcactg     600
ctcggccagt actatgcac tggctgctga ggactggtgg ctggaaggtc tcagctgtga     660
ctttggctta tctgatcttc tgcctgtgtt cccttgtggg cattcttcat cttcaaagag     720
ccctggtcct gaggaggaaa agaaagcgaa tgactgaccc caccaggaga ttcttcaaag     780
tgacgcctcc cccaggaagc gggccccaga accagtacgg gaacgtgctg tctctcccca     840
cacccacctc aggcctcgga cgcgcccagc gttgggccgc aggcctgggg ggcactgccc     900
cgtcttatgg aaacccgagc agcgacgtcc aggcggatgg agccttgggg tcccggagcc     960
cgccgggagt gggcccagaa gaagaggaag gggagggcta tgaggaacct gacagtgagg    1020
aggactccga gttctatgag aacgactcca accttgggca ggaccagctc tcccaggatg    1080
```

```
gcagcggcta cgagaaccct gaggatgagc ccctgggtcc tgaggatgaa gactccttct   1140
ccaacgctga gtcttatgag aacgaggatg aagagctgac ccagccggtc gccaggacaa   1200
tggacttcct gagccctcat gggtcagcct gggaccccag ccgggaagca acctccctgg   1260
ggtcccagtc ctatgaggat atgagaggaa tcctgtatgc agcccccag ctccgctcca    1320 ttcggggcca gcctggaccc aatcatgagg aagatgcaga ctcttatgag aacatggata   1380
atcccgatgg gccagaccca gcctggggag aggggggccg catgggcacc tggagcacca   1440
ggtagtgata aaactcgagc ggtggtggcg gttctggtgg tggtggtagc ggtggcggtg   1500
gtagtggcgg tggcggtgct agctagtgat aatctgggcc ctggggctgc atcctcacct   1560
acagagatgg cttcaacgtc tccatcatgt ataacctcac tgttctgggt ctggagcccc   1620
caactccctt gacagtgtac gctggagcag gttccagggt ggggctgccc tgccgcctgc   1680
ctgctggtgt ggggacccgg tctttcctca ctgccaagtg gactcctcct gggggaggcc   1740
ctgacctcct ggtgactgga gacaatggcg acttttaccct tcgactagag gatgtgagcc   1800
aggcccaggc tgggacctac acctgccata tccatctgca ggaacagcag ctcaatgcca   1860
ctgtcacatt ggcaatcatc acagtgactc ccaaatcctt tgggtcacct ggatccctgg   1920
ggaagctgct ttgtgaggtg actccagtat ctggacaaga acgctttgtg tggagctctc   1980
tggacacccc atcccagagg agtttctcag gaccttggct ggaggcacag gaggcccagc   2040
tcctttccca gccttggcaa tgccagctgt accaggggga gaggcttctt ggagcagcag   2100
tgtacttcac agagctgtct agcccaggtg cccaacgctc tgggagagcc ccaggtgccc   2160
tcccagcagg ccacctcgat atcgagggtc gtatggatcc caaatcttgt gacaaaactc   2220
acacatgccc accgtgccca gcacctgaac tcctgggggg accgtcagtc ttcctcttcc   2280
ccccaaaacc caaggacacc ctcatgatct cccggacccc tgaggtcaca tgcgtggtgg   2340
tggacgtgag ccacgaagac cctgaggtca agttcaactg gtacgtggac ggcgtggagg   2400
tgcataatgc caagacaaag ccgcgggagg agcagtacaa cagcacgtac cgtgtggtca   2460
gcgtcctcac cgtcctgcac caggactggc tgaatggcaa ggagtacaag tgcaaggtct   2520
ccaacaaagc cctcccagcc cccatcgaga aaaccatctc caaagccaaa gggcagcccc   2580
gagagccaca ggtgtacacc ctgcccccat cccgggatga gctgaccaag aaccaggtca   2640
gcctgacctg cctggtcaaa ggcttctatc ccagcgacat cgccgtggag tgggagagca   2700
atgggcagcc ggagaacaac tacaagacca cgcctcccgt gctggactcc gacggctcct   2760
tcttcctcta cagcaagctc accgtggaca agagcaggtg gcagcagggg aacgtcttct   2820
catgctccgt gatgcatgag gctctgcaca accactacac gcagaagagc ctctccctgt   2880
ctccgggtaa atagtgataa gcggccgcag gcgcggaaca aaaactcatc tcagaagagg   2940
atctgaatgg ggccgcacat catcatcacc atcactaggg tggcggctcc ggttccggtg   3000
attttgatta tgaaaagatg gcaaacgcta ataaggggc tatgaccgaa atgccgatg     3060 aaaacgcgct acagtctgac gctaaaggca aacttgattc tgtcgctact gattacggtg   3120
ctgctatcga tggtttcatt ggtgacgttt ccggccttgc taatggtaat ggtgctactg   3180
gtgattttgc tggctctaat tcccaaatgg ctcaagtcgg tgacggtgat aattcacctt   3240
taatgaataa tttccgtcaa tatttacctt ccctccctca atcggttgaa tgtcgccctt   3300
ttgtctttgg cgctggtaaa ccatatgaat tttctattga ttgtgacaaa ataaacttat   3360
tccgtggtgt ctttgcgttt cttttatatg ttgccacctt tatgtatgta ttttctacgt   3420
```

```
ttgctaacat actgcgtaat aaggagtctt aataagaatt cactggccgt cgttttacaa    3480
cgtcgtgact gggaaaaccc tggcgttacc caacttaatc gccttgcagc acatccccct    3540
ttcgccagct ggcgtaatag cgaagaggcc cgcaccgatc gcccttccca acagttgcgc    3600
agcctgaatg gcgaatggcg cctgatgcgg tattttctcc ttacgcatct gtgcggtatt    3660
tcacaccgca tacgtcaaag caaccatagt acgcgcctg tagcggcgca ttaagcgcgg     3720
cgggtgtggt ggttacgcgc agcgtgaccg ctacacttgc cagcgcccta gcgcccgctc    3780
ctttcgcttt cttcccttcc tttctcgcca cgttcgccgg ctttccccgt caagctctaa    3840
atcgggggct ccctttaggg ttccgattta gtgctttacg gcacctcgac cccaaaaaac    3900
ttgatttggg tgatggttca cgtagtgggc catcgccctg atagacggtt tttcgccctt    3960
tgacgttgga gtccacgttc tttaatagtg gactcttgtt ccaaactgga acaacactca    4020
accctatctc gggctattct tttgatttat aagggatttt gccgatttcg gcctattggt    4080
taaaaaatga gctgatttaa caaaaattta acgcgaattt taacaaaata ttaacgttta    4140
caatttatg gtgcactctc agtacaatct gctctgatgc cgcatagtta agccagcccc     4200
gacacccgcc aacacccgct gacgcgccct gacgggcttg tctgctcccg gcatccgctt    4260
acagacaagc tgtgaccgtc tccgggagct gcatgtgtca ggttttca ccgtcatcac      4320
cgaaacgcgc gagacgaaag gcctcgtga tacgcctatt tttataggtt aatgtcatga     4380
taataatggt ttcttagacg tcaggtggca cttttcgggg aaatgtgcgc ggaacccta    4440
tttgtttatt tttctaaata cattcaaata tgtatccgct catgagacaa taaccctgat    4500
aaatgcttca ataatattga aaaggaaga gtatgagtat tcaacatttc cgtgtcgccc    4560
ttattccctt ttttgcggca ttttgccttc ctgtttttgc tcacccagaa acgctggtga    4620
aagtaaaaga tgctgaagat cagttgggtg cacgagtggg ttacatcgaa ctggatctca    4680
acagcggtaa gatccttgag agttttcgcc ccgaagaacg ttttccaatg atgagcactt    4740
ttaaagttct gctatgtggc gcggtattat cccgtattga cgccgggcaa gagcaactcg    4800
gtcgccgcat acactattct cagaatgact tggttgagta ctcaccagtc acagaaaagc    4860
atcttacgga tggcatgaca gtaagagaat tatgcagtgc tgccataacc atgagtgata    4920
acactgcggc caacttactt ctgacaacga tcggaggacc gaaggagcta accgcttttt    4980
tgcacaacat gggggatcat gtaactcgcc ttgatcgttg ggaaccggag ctgaatgaag    5040
ccataccaaa cgacgagcgt gacaccacga tgcctgtagc aatggcaaca acgttgcgca    5100
aactattaac tggcgaacta cttactctag cttcccggca acaattaata gactggatgg    5160
aggcggataa agttgcagga ccacttctgc gctcggccct tccggctggc tggtttattg    5220
ctgataaatc tggagccggt gagcgtgggt ctcgcggtat cattgcagca ctggggccag    5280
atggtaagcc ctcccgtatc gtagttatct acacgacggg gagtcaggca actatggatg    5340
aacgaaatag acagatcgct gagataggtg cctcactgat taagcattgg taactgtcag    5400
accaagttta ctcatatata ctttagattg atttaaaact tcatttttaa tttaaaagga    5460
tctaggtgaa gatccttttt gataatctca tgaccaaaat cccttaacgt gagttttcgt    5520
tccactgagc gtcagacccc gtagaaaaga tcaaaggatc ttcttgagat ccttttttc     5580
tgcgcgtaat ctgctgcttg caaacaaaaa aaccaccgct accagcggtg gtttgtttgc    5640
cggatcaaga gctaccaact ctttttccga aggtaactgg cttcagcaga gcgcagatac    5700
caaatactgt ccttctagtg tagccgtagt taggccacca cttcaagaac tctgtagcac    5760
cgcctacata cctcgctctg ctaatcctgt taccagtggc tgctgccagt ggcgataagt    5820
```

```
cgtgtcttac cggqttggac tcaagacgat agttaccgga taaggcgcag cggtcgggct    5880
gaacgggggg ttcgtgcaca cagcccagct tggagcgaac gacctacacc gaactgagat    5940
acctacagcg tgagctatga gaaagcgcca cgcttcccga agggagaaag gcggacaggt    6000
atccggtaag cggcagggtc ggaacaggag agcgcacgag ggagcttcca gggggaaacg    6060
cctggtatct ttatagtcct gtcgggtttc gccacctctg acttgagcgt cgattttgt    6120 gatgctcgtc agggggggcgg agcctatgga aaaacgccag caacgcggcc ttttacggt    6180 tcctggcctt tgctggcct tttgctcaca tgttctttcc tgcgttatcc cctgattctg    6240
tggataaccg tattaccgcc tttgagtgag ctgataccgc tcgccgcagc cgaacgaccg    6300
agcgcagcga gtcagtgagc gaggaagcgg aag                                  6333

<210> SEQ ID NO 2
<211> LENGTH: 747
<212> TYPE: DNA
<213> ORGANISM: Artificial Sequence
<220> FEATURE:
<223> OTHER INFORMATION: synthesized sequence

<400> SEQUENCE: 2
gaggtgcagc tggtggagtc tgggggaggc gtggtccagc ctggaggtc cctgagactc       60 tcctgtgcag cctctggatt caccttcagt aattatgcta tgcactgggt ccgccaggct     120
ccaggcaagg ggctggagtg ggtggcagtt atatcatatg atggaagcga taaatactac     180
gcagactccg tgaagggccg attcaccatc tccagagaca attccaagaa cacgctgtat     240
ctgcaaatga aaagcctgag agctgaggac acggctgtgt attactgtgc gagatcaatc     300
gggtttcttg agagcgatgc ttttgatatc tggggccaag gaccacggt caccgtctcg     360 agcggtggtg gcggttctgg tggtggtggt agcggtggcg gtggtagtgg cggtggcggt     420
gctagcgaca tcgtgctgac acagtctcca tcctccctgt ctgcatctgt aggagacaga     480
gtcaccatca cttgccaggc gagtcacggc atttccaact tttaaattg gtatcagcag     540 aaaccaggaa aagccctaa gctcctcatc tacgatgcat ccactttgga aacaggggtc     600
ccatcaaggt tcagtggaag tggatctggg acagatttta gattcaccat cagcagcctg     660
cagcctgaag atattgcaac atattactgt caacaatttg ataatctccc gatcaccttc     720
ggccaaggga cacgactgga gattaaa                                         747

<210> SEQ ID NO 3
<211> LENGTH: 249
<212> TYPE: PRT
<213> ORGANISM: Artificial Sequence
<220> FEATURE:
<223> OTHER INFORMATION: synthesized sequence

<400> SEQUENCE: 3

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Lys Ser Leu Arg Ala Glu Asp Thr Ala Val Tyr Tyr Cys
                85                  90                  95

Ala Arg Ser Ile Gly Phe Leu Glu Ser Asp Ala Phe Asp Ile Trp Gly
            100                 105                 110

Gln Gly Thr Thr Val Thr Val Ser Ser Gly Gly Gly Gly Ser Gly Gly
        115                 120                 125

Gly Gly Ser Gly Gly Gly Ser Gly Gly Gly Ala Ser Asp Ile
    130                 135                 140

Val Leu Thr Gln Ser Pro Ser Ser Leu Ser Ala Ser Val Gly Asp Arg
145                 150                 155                 160

Val Thr Ile Thr Cys Gln Ala Ser His Gly Ile Ser Asn Phe Leu Asn
                165                 170                 175

Trp Tyr Gln Gln Lys Pro Gly Lys Ala Pro Lys Leu Leu Ile Tyr Asp
            180                 185                 190

Ala Ser Thr Leu Glu Thr Gly Val Pro Ser Arg Phe Ser Gly Ser Gly
        195                 200                 205

Ser Gly Thr Asp Phe Arg Phe Thr Ile Ser Ser Leu Gln Pro Glu Asp
    210                 215                 220

Ile Ala Thr Tyr Tyr Cys Gln Gln Phe Asp Asn Leu Pro Ile Thr Phe
225                 230                 235                 240

Gly Gln Gly Thr Arg Leu Glu Ile Lys
            245

<210> SEQ ID NO 4
<211> LENGTH: 756
<212> TYPE: DNA
<213> ORGANISM: Artificial Sequence
<220> FEATURE:
<223> OTHER INFORMATION: synthesized sequence

<400> SEQUENCE: 4
caggtccagt tggtgcaatc tggagctgag gtgaagaagc tggggcctc agtgaaggtc      60 tcctgcaagg cttctggtta cacctttacc agctatggta tcagctgggt gcgacaggcc    120
cctggacaag gcttgagtg gatgggatgg atcagcgctt acaatggtaa cacaaactat     180
gcacagaagc tccagggcag agtcaccatg accacagaca catccacgag cacagcctac    240
atggagctga ggagcctgag atctgacgac acggccgtgt attactgtgc gagagatgag    300
ggagctaact ggggtgatgc ttttgatatc tggggccaag gaccatggt caccgtctcg     360 agcggtggtg gcggttctgg tggtggtggt agcggtggcg gtggtagtgg cggtggcggt    420
gctagccagc ttgtgctgac tcaatcgccc tcagcgtctg gaccccccgg cagagggtc    480 accatctctt gttctggaag cagctccaac atcggaaata atgctgtaaa ctggtaccag    540
cagctcccag gaacggcccc caaaatcctc atctatagta ataatcagcg gccctcaggg    600
gtccctgacc gattctctgg ctccaagtct ggcgcctcag cctccctggc catcagtggg    660
ctccagtctg aggatgagtc tgattattac tgtgcagcat gggatgacag cctgaatgct    720
gtggtattca gcggagggac cgagctgacc gtccta                              756

<210> SEQ ID NO 5
<211> LENGTH: 252
<212> TYPE: PRT
<213> ORGANISM: Artificial Sequence
<220> FEATURE:
<223> OTHER INFORMATION: synthesized sequence

<400> SEQUENCE: 5

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Glu Gly Ala Asn Trp Gly Asp Ala Phe Asp Ile Trp Gly
            100                 105                 110

Gln Gly Thr Met Val Thr Val Ser Ser Gly Gly Gly Gly Ser Gly Gly
        115                 120                 125

Gly Gly Ser Gly Gly Gly Gly Ser Gly Gly Gly Ala Ser Gln Leu
    130                 135                 140

Val Leu Thr Gln Ser Pro Ser Ala Ser Gly Thr Pro Gly Gln Arg Val
145                 150                 155                 160

Thr Ile Ser Cys Ser Gly Ser Ser Asn Ile Gly Asn Asn Ala Val
                165                 170                 175

Asn Trp Tyr Gln Gln Leu Pro Gly Thr Ala Pro Lys Ile Leu Ile Tyr
            180                 185                 190

Ser Asn Asn Gln Arg Pro Ser Gly Val Pro Asp Arg Phe Ser Gly Ser
            195                 200                 205

Lys Ser Gly Ala Ser Ala Ser Leu Ala Ile Ser Gly Leu Gln Ser Glu
        210                 215                 220

Asp Glu Ser Asp Tyr Tyr Cys Ala Ala Trp Asp Ser Leu Asn Ala
225                 230                 235                 240

Val Val Phe Ser Gly Gly Thr Glu Leu Thr Val Leu
                245                 250
```

<210> SEQ ID NO 6
<211> LENGTH: 756
<212> TYPE: DNA
<213> ORGANISM: Artificial Sequence
<220> FEATURE:
<223> OTHER INFORMATION: synthesized sequence

<400> SEQUENCE: 6

```
caggtacagc ttcaggagtc gggcccagga ctggtgaagc cttcggagac cctgtccctc    60
acctgcactg tctctggtgg ctccatcagc agtggtggtt actactgggg ctggatccgc   120
cagcccccag ggaaggggct ggagtggatt gggagtatct attatagtgg gagaacctac   180
tacaacccgt ccctcaagag tcgagtcacc atatccgtag acacgtccag gaaccagttc   240
tccctgaaac tgagctctct gaccgccgca gacacggctg tgtattactg cgagaact    300
ggggggggag cctacggttt tgactactgg ggccagggaa ccctggtcac cgtctcgagc   360
ggtggtggcg gttctggtgg tggtggtagc ggtggcggtg gtagtggcgg tggcggtgct   420
agccagcctg tgctgactca gccgcactct gtgtcggagt ctccgggcaa gacggtgacc   480
atctcctgca cccgcagcag tggcaacatt gccagcaact atgtgcagtg gtatcagaag   540
cgcccgggca gtccccccac cactgtgatc tatgaggaca ccaaaggcc ctctggggtc   600
```

```
cctgatcgct tctccgcctc catcgacagc tcctccaact ctgcctccct caccatctct    660
ggactgagga ctgaggacga ggctgactac tactgtcagt cttatgacac tatcttgggt    720
tatgtcttcg gaggaggcac ccagctgacc gccta                               756
```

<210> SEQ ID NO 7
<211> LENGTH: 252
<212> TYPE: PRT
<213> ORGANISM: Artificial Sequence
<220> FEATURE:
<223> OTHER INFORMATION: synthesized sequence

<400> SEQUENCE: 7

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Gly Tyr Tyr Trp Gly Trp Ile Arg Gln Pro Pro Gly Lys Gly Leu Glu
        35                  40                  45

Trp Ile Gly Ser Ile Tyr Tyr Ser Gly Arg Thr Tyr Tyr Asn Pro Ser
    50                  55                  60

Leu Lys Ser Arg Val Thr Ile Ser Val Asp Thr Ser Arg Asn Gln Phe
65                  70                  75                  80

Ser Leu Lys Leu Ser Ser Leu Thr Ala Ala Asp Thr Ala Val Tyr Tyr
                85                  90                  95

Cys Ala Arg Thr Gly Gly Gly Ala Tyr Gly Phe Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Gly Gly Gly Ala Ser Gln Pro Val
    130                 135                 140

Leu Thr Gln Pro His Ser Val Ser Glu Ser Pro Gly Lys Thr Val Thr
145                 150                 155                 160

Ile Ser Cys Thr Arg Ser Ser Gly Asn Ile Ala Ser Asn Tyr Val Gln
                165                 170                 175

Trp Tyr Gln Lys Arg Pro Gly Ser Pro Pro Thr Thr Val Ile Tyr Glu
            180                 185                 190

Asp Asn Gln Arg Pro Ser Gly Val Pro Asp Arg Phe Ser Ala Ser Ile
        195                 200                 205

Asp Ser Ser Ser Asn Ser Ala Ser Leu Thr Ile Ser Gly Leu Arg Thr
    210                 215                 220

Glu Asp Glu Ala Asp Tyr Tyr Cys Gln Ser Tyr Asp Thr Ile Leu Gly
225                 230                 235                 240

Tyr Val Phe Gly Gly Gly Thr Gln Leu Thr Ala Leu
                245                 250
```

<210> SEQ ID NO 8
<211> LENGTH: 759
<212> TYPE: DNA
<213> ORGANISM: Artificial Sequence
<220> FEATURE:
<223> OTHER INFORMATION: synthesized sequence

<400> SEQUENCE: 8

```
gaggttcagc tgttggagtc tggagctgag gtgaagaagc ctggggcctc agtgaaggtc     60
tcctgcaagg cttctggtta cacctttacc agctatggta tcagctgggt gcgacaggcc    120
cctggacaag ggcttgagtg gatgggatgg atcagcgctt acaatggtaa cacaaactat    180
```

```
gcacagaagc tccagggcag agtcaccatg accacagaca catccacgag cacagcctac    240
atggagctga ggagcctgag atctgacgac acggccgtgt attactgtgc gagagatggc    300
tggtgggagc tactacgtcc cgatgatgct tttgatatct ggggccaagg acaacggtc    360 accgtctcga gcggtggtgg cggttctggt ggtggtggta gcggtggcgg tggtagtggc    420
ggtggcggtg ctagccagct tgtgctgact cagtcgccct cagtgtccgt gtccccagga    480
cagacagcca gcatcacctg ctctggagat aagttgggag ataaatatgc ttactggtat    540
cagcagaagc caggccaggc ccctgtgctg gtcatctatt atgatagcga ccggccctca    600
gggatccctg agcgattctc tggctccaac tctgggaaca cggccaccct gaccatcagc    660
agggtcgaag ccggggatga ggccgactat tactgtcagg tgtgggatag tagtagtgat    720
caagtggtat tcggcggagg cacccagctg accgtcctc                           759
```

<210> SEQ ID NO 9
<211> LENGTH: 253
<212> TYPE: PRT
<213> ORGANISM: Artificial Sequence
<220> FEATURE:
<223> OTHER INFORMATION: synthesized sequence

<400> SEQUENCE: 9

```
Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Trp Trp Glu Leu Leu Arg Pro Asp Asp Ala Phe Asp
            100                 105                 110

Ile Trp Gly Gln Gly Thr Thr Val Thr Val Ser Ser Gly Gly Gly Gly
        115                 120                 125

Ser Gly Gly Gly Gly Ser Gly Gly Gly Gly Ser Gly Gly Gly Gly Ala
    130                 135                 140

Ser Gln Leu Val Leu Thr Gln Ser Pro Ser Val Ser Val Ser Pro Gly
145                 150                 155                 160

Gln Thr Ala Ser Ile Thr Cys Ser Gly Asp Lys Leu Gly Asp Lys Tyr
                165                 170                 175

Ala Tyr Trp Tyr Gln Gln Lys Pro Gly Gln Ala Pro Val Leu Val Ile
            180                 185                 190

Tyr Tyr Asp Ser Asp Arg Pro Ser Gly Ile Pro Glu Arg Phe Ser Gly
        195                 200                 205

Ser Asn Ser Gly Asn Thr Ala Thr Leu Thr Ile Ser Arg Val Glu Ala
    210                 215                 220

Gly Asp Glu Ala Asp Tyr Tyr Cys Gln Val Trp Asp Ser Ser Ser Asp
225                 230                 235                 240

Gln Val Val Phe Gly Gly Gly Thr Gln Leu Thr Val Leu
                245                 250
```

<210> SEQ ID NO 10
<211> LENGTH: 756
<212> TYPE: DNA
<213> ORGANISM: Artificial Sequence
<220> FEATURE:
<223> OTHER INFORMATION: synthesized sequence

<400> SEQUENCE: 10

```
gaggtgcagc tggtggagtc tgggggaggc gtggtccagc ctgggaggtc cctgagactc    60
tcctgtgcag cgtctggatt caccttcagt agctttggca tacactgggt ccgccaggct   120
ccaggcaagg gctggagtg gtggcagtt atatggtacg atggaagtaa taaatactat    180
gcagactccg tgaagggccg attcaccatc tccagagaca attccaagaa cacgctctat   240
ctgcaaatga acagcctgag agccgaggac acggctgtgt attactgtgc aaggattttt   300
ggggtggtg actggggtat ggacgtctgg ggccaaggga ccacggtcac cgtctcgagc   360
ggtggtggcg ttctggtgg tggtggtagc ggtggcggtg gtagtggcgg tggcggtgct   420
agccagtctg tgctgactca gccgccctca gtgtctgggg ccccagggca gagggtcacc   480
atctcctgca ctgggagcag ctccaacatc ggggcaggtg atgatgtaca ttggtaccag   540
cagcttccag gaacagcccc caaactcctc atctatacta caacaatcg gccctcaggg   600
gtccctgacc gattctctgg ctccaagtct ggcacctcag cctccctggc catcagtgag   660
ctccagtctg aggatgaggc tgattattat tgtgcagcat gggatgacag cctgaatggt   720
ccggtgttcg gcggaggaac ccagctgacc gccctc                              756
```

<210> SEQ ID NO 11
<211> LENGTH: 252
<212> TYPE: PRT
<213> ORGANISM: Artificial Sequence
<220> FEATURE:
<223> OTHER INFORMATION: synthesized sequence

<400> SEQUENCE: 11

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Ile His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Gly Gly Gly Asp Trp Gly Met Asp Val Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Gly Gly Gly Ala Ser Gln Ser Val
    130                 135                 140

Leu Thr Gln Pro Pro Ser Val Ser Gly Ala Pro Gly Gln Arg Val Thr
145                 150                 155                 160

Ile Ser Cys Thr Gly Ser Ser Ser Asn Ile Gly Ala Gly Asp Asp Val
                165                 170                 175
```

His Trp Tyr Gln Gln Leu Pro Gly Thr Ala Pro Lys Leu Leu Ile Tyr
            180                 185                 190

Thr Asn Asn Arg Pro Ser Gly Val Pro Asp Arg Phe Ser Gly Ser
        195                 200                 205

Lys Ser Gly Thr Ser Ala Ser Leu Ala Ile Ser Glu Leu Gln Ser Glu
    210                 215                 220

Asp Glu Ala Asp Tyr Tyr Cys Ala Ala Trp Asp Ser Leu Asn Gly
225                 230                 235                 240

Pro Val Phe Gly Gly Gly Thr Gln Leu Thr Ala Leu
                245                 250

<210> SEQ ID NO 12
<211> LENGTH: 747
<212> TYPE: DNA
<213> ORGANISM: Artificial Sequence
<220> FEATURE:
<223> OTHER INFORMATION: synthesized sequence

<400> SEQUENCE: 12
gaggtgcagc tgttgcagtc tggggggaggc ttggtacagc ctggagggtc cctgagactc      60
tcctgtgcag cctctggatt caccttcagt agttatgaaa tgaactgggt ccgccaggct     120
ccagggaagg ggctggagtg ggtttcatac attagtagta gtggtagtac catatactac     180
gcagactctg tgaagggccg attcaccatc tccagagaca acgccaagaa ctcactgtat     240
ctgcaaatga acagcctgag agccgaggac acggctgtgt attactgtgc gagagttgga     300
ctccttgatg ctttttgatat ctggggccaa gggaccatgg tcaccgtctc gagcggtggt     360
ggcggttctg gtggtggtgg tagcggtggc ggtggtagtg gcggtggcgg tgctagccag     420
tctgtcttga cgcagccgcc ctcagtgtct gcggccccag gacagaaggt caccatctcc     480
tgctctggaa gcagctccaa cattgggaat aattatgtat cctggtacca gctgatccca     540
gaaaaagccc ccagactcct catttatgac gatgataagc gaccctccgg gattcctgac     600
cgattctctg gctcccagtc tggcacgtca gccaccctgg gcatcaccgg actccagact     660
ggggacgagg ccgattattt ctgcggaaca tgggataaca gcctgagtgg tgcggtattc     720
ggcggaggaa cccagctgat cattttta                                       747

<210> SEQ ID NO 13
<211> LENGTH: 249
<212> TYPE: PRT
<213> ORGANISM: Artificial Sequence
<220> FEATURE:
<223> OTHER INFORMATION: synthesized sequence

<400> SEQUENCE: 13

Glu Val Gln Leu Leu Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Leu Asp Ala Phe Asp Ile Trp Gly Gln Gly Thr
            100                 105                 110

Met Val Thr Val Ser Ser Gly Gly Gly Ser Gly Gly Gly Ser
        115                 120                 125

Gly Gly Gly Gly Ser Gly Gly Gly Ala Ser Gln Ser Val Leu Thr
        130                 135                 140

Gln Pro Pro Ser Val Ser Ala Ala Pro Gly Gln Lys Val Thr Ile Ser
145                 150                 155                 160

Cys Ser Gly Ser Ser Asn Ile Gly Asn Asn Tyr Val Ser Trp Tyr
                165                 170                 175

Gln Leu Ile Pro Glu Lys Ala Pro Arg Leu Leu Ile Tyr Asp Asp Asp
            180                 185                 190

Lys Arg Pro Ser Gly Ile Pro Asp Arg Phe Ser Gly Ser Gln Ser Gly
        195                 200                 205

Thr Ser Ala Thr Leu Gly Ile Thr Gly Leu Gln Thr Gly Asp Glu Ala
        210                 215                 220

Asp Tyr Phe Cys Gly Thr Trp Asp Asn Ser Leu Ser Gly Ala Val Phe
225                 230                 235                 240

Gly Gly Gly Thr Gln Leu Ile Ile Leu
                245

<210> SEQ ID NO 14
<211> LENGTH: 750
<212> TYPE: DNA
<213> ORGANISM: Artificial Sequence
<220> FEATURE:
<223> OTHER INFORMATION: synthesized sequence

<400> SEQUENCE: 14
gaggtgcatc tggtagagtc tgggggaggc gtggtccagc ctggggaggtc cctgagactc     60
tcctgtgcag cctctggatt caccttcagt aactatgcta tgcactgggt ccgccaggct    120
ccaggcaagg gctggagtg gtggcagtt atatcatatg atggaaacaa tcaatactac    180
gcagactccg tgaagggccg attcaccatc tccagagaca attccaagaa cacgctgtat    240
ctgcaaatga acagcctgag agctgaggac acggctgtgt tttactgtgc gagatcaatc    300
ggattccttg agagcgatgc ttttgatatc tggggccaag ggacaacggt caccgtctcg    360
agcggtggtg gcggttctgg tggtggtggt agcggtggcg gtggtagtgg cggtggcgtg    420
gctagcgaaa tagtgttgat gcagtctcca ggcaccctgt ctttgtctcc aggggaaaga    480
gccaccctct cctgcagggc cagtcaaagt tttagtgacg gtccttagc ctggtaccag    540
cagaaacctg gccagcctcc cagactcgtc atctatgatg catcgaagcg ggccactggc    600
atccctgaca ggttcagtgg cagtaggtct gggacagagt tcactctcac catcagcagc    660
ctgcagtctg aagattttgc agttattcc tgtcagcagt attataactg gcctcccacc    720
ttcggccaag ggacacgact ggagattaaa    750

<210> SEQ ID NO 15
<211> LENGTH: 250
<212> TYPE: PRT
<213> ORGANISM: Artificial Sequence
<220> FEATURE:
<223> OTHER INFORMATION: synthesized sequence

<400> SEQUENCE: 15

Glu Val His Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Phe Tyr Cys
                85                  90                  95

Ala Arg Ser Ile Gly Phe Leu Glu Ser Asp Ala Phe Asp Ile Trp Gly
            100                 105                 110

Gln Gly Thr Thr Val Thr Val Ser Ser Gly Gly Gly Gly Ser Gly Gly
        115                 120                 125

Gly Gly Ser Gly Gly Gly Ser Gly Gly Gly Ala Ser Glu Ile
    130                 135                 140

Val Leu Met Gln Ser Pro Gly Thr Leu Ser Leu Ser Pro Gly Glu Arg
145                 150                 155                 160

Ala Thr Leu Ser Cys Arg Ala Ser Gln Ser Phe Ser Asp Gly Ser Leu
                165                 170                 175

Ala Trp Tyr Gln Gln Lys Pro Gly Gln Pro Pro Arg Leu Val Ile Tyr
            180                 185                 190

Asp Ala Ser Lys Arg Ala Thr Gly Ile Pro Asp Arg Phe Ser Gly Ser
        195                 200                 205

Arg Ser Gly Thr Glu Phe Thr Leu Thr Ile Ser Ser Leu Gln Ser Glu
    210                 215                 220

Asp Phe Ala Val Tyr Ser Cys Gln Gln Tyr Tyr Asn Trp Pro Pro Thr
225                 230                 235                 240

Phe Gly Gln Gly Thr Arg Leu Glu Ile Lys
                245                 250

<210> SEQ ID NO 16
<211> LENGTH: 762
<212> TYPE: DNA
<213> ORGANISM: Artificial Sequence
<220> FEATURE:
<223> OTHER INFORMATION: synthesized sequence

<400> SEQUENCE: 16
cgggtgcggc tgcaggagtc gggcccagga ctggtgaagc cttcggagac cctgtccctc      60
acctgcactg tctctggtgg ctccatcagc agtagtagtt actactgggg ctggatccgc     120
cagcccccag gaagggggct ggagtggatt gggagtatct attatagtgg gagcacctac     180
tacaacccgt ccctcaagag tcgagtcacc atatcagtag acacgtccaa gaaccagttc     240
tccctgaagc tgagctctgt gaccgccgcg gacacggccg tgtattactg cgagagag      300 tatagtggct acgatgggc ttatgttggc tactggggcc agggaaccct ggtcaccgtc     360
tcgagcggtg gtggcggttc tggtggtggt ggtagcggtg gcggtggtag tggcggtggc     420
ggtgctagcc agtctgtcct gacgcagccg ccctcagtgt ctggggcccc agggcagagg     480
gtcaccatct cctgcactgg gagcaactcc aacatccggg caggttatga tgtacactgg     540
taccagcagc ttccaggaac agtccccaaa ctcctcatct atggtaacag caatcgaccc     600 tcagggggtcc ctgaccgatt ctctggctcc aagtctggca cctcagcctc cctggccatc     660
agtgggctcc agtccgaaga tgagggtaat tacttctgtg ctacatggga tgacagcctg     720
tggggctggg tgttcggcgc agggaccgag ctgaccgtcc ta          762

<210> SEQ ID NO 17
<211> LENGTH: 254
<212> TYPE: PRT
<213> ORGANISM: Artificial Sequence
<220> FEATURE:
<223> OTHER INFORMATION: synthesized sequence

<400> SEQUENCE: 17

Arg Val Arg Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Tyr Ser Gly Tyr Asp Gly Ala Tyr Val Gly Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Gly Gly Gly Ala Ser Gln
    130                 135                 140

Ser Val Leu Thr Gln Pro Pro Ser Val Ser Gly Ala Pro Gly Gln Arg
145                 150                 155                 160

Val Thr Ile Ser Cys Thr Gly Ser Asn Ser Asn Ile Arg Ala Gly Tyr
                165                 170                 175

Asp Val His Trp Tyr Gln Gln Leu Pro Gly Thr Val Pro Lys Leu Leu
            180                 185                 190

Ile Tyr Gly Asn Ser Asn Arg Pro Ser Gly Val Pro Asp Arg Phe Ser
        195                 200                 205

Gly Ser Lys Ser Gly Thr Ser Ala Ser Leu Ala Ile Ser Gly Leu Gln
    210                 215                 220

Ser Glu Asp Glu Gly Asn Tyr Phe Cys Ala Thr Trp Asp Asp Ser Leu
225                 230                 235                 240

Trp Gly Trp Val Phe Gly Ala Gly Thr Glu Leu Thr Val Leu
                245                 250

<210> SEQ ID NO 18
<211> LENGTH: 747
<212> TYPE: DNA
<213> ORGANISM: Artificial Sequence
<220> FEATURE:
<223> OTHER INFORMATION: synthesized sequence

<400> SEQUENCE: 18
caggtccagt tggtgcagtc tggggctgag gtgaagaagc ctgggtcctc ggtgaaggtc          60
tcctgcaaga cttctggagg cacctttagt aattatgcta tcaactgggt gcgacaggcc         120
cctggacaag gcttgagtg gatgggagtg atcatcccta tgtttggtcc agcaaactac         180
gtacagaagt tccagggcag agtcacaatt accgcggacg aaaccacgag cacagcctac         240
atggagctga gcagcctgag atctgaggac acggccatct attactgtgc gagagacttg         300

```
gctccagctg gcttctacgg tatggacgtc tggggccaag ggaccacggt caccgtctcg      360
agcggtggtg gcggttctgg tggtggtggt agcggtggcg gtggtagtgg cggtggcggt      420
gctagcgaca ttgtgttgac tcagtctcca tcttccgtgt ctgcatctgt aggagacaga      480
gtcaccatca cttgtcgggc gagtcagggt attagcaact ggttagcctg gtatcagcag      540
aagccaggga aagcccctaa actcctcatc tatgctgcat ccagtttaca aagtggggtc      600
ccatcaaggt tcagcggcag tagatctggg acagatttca ctctcaccat cagcagcctg      660
cagcctgaag attttgcaac ttactattgt caacaggcta ggaatttccc cttcaccttc      720
ggccaaggga cacgactgga gattaaa                                         747
```

<210> SEQ ID NO 19
<211> LENGTH: 249
<212> TYPE: PRT
<213> ORGANISM: Artificial Sequence
<220> FEATURE:
<223> OTHER INFORMATION: synthesized sequence

<400> SEQUENCE: 19

```
Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Asn Tyr
            20                  25                  30

Ala Ile Asn Trp Val Arg Gln Ala Pro Gly Gln Gly Leu Glu Trp Met
        35                  40                  45

Gly Val Ile Ile Pro Met Phe Gly Pro Ala Asn Tyr Val Gln Lys Phe
    50                  55                  60

Gln Gly Arg Val Thr Ile Thr Ala Asp Glu Thr Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Asp Leu Ala Pro Ala Gly Phe Tyr Gly Met Asp Val Trp Gly
            100                 105                 110

Gln Gly Thr Thr Val Thr Val Ser Ser Gly Gly Gly Ser Gly Gly
        115                 120                 125

Gly Gly Ser Gly Gly Gly Gly Ser Gly Gly Gly Gly Ala Ser Asp Ile
    130                 135                 140

Val Leu Thr Gln Ser Pro Ser Ser Val Ser Ala Ser Val Gly Asp Arg
145                 150                 155                 160

Val Thr Ile Thr Cys Arg Ala Ser Gln Gly Ile Ser Asn Trp Leu Ala
                165                 170                 175

Trp Tyr Gln Gln Lys Pro Gly Lys Ala Pro Lys Leu Leu Ile Tyr Ala
            180                 185                 190

Ala Ser Ser Leu Gln Ser Gly Val Pro Ser Arg Phe Ser Gly Ser Arg
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gln Gln Ala Arg Asn Phe Pro Phe Thr Phe
225                 230                 235                 240

Gly Gln Gly Thr Arg Leu Glu Ile Lys
                245
```

<210> SEQ ID NO 20
<211> LENGTH: 756
<212> TYPE: DNA

<213> ORGANISM: Artificial Sequence
<220> FEATURE:
<223> OTHER INFORMATION: synthesized sequence

<400> SEQUENCE: 20

```
caggtgcagc tgttgcagtc tggggctgag gtgaagaagc ctgggtcctc ggtgaaggtc       60
tcctgcaagg cttctggagg caccttcagc agctatgcta tcagctgggt gcgacaggcc      120
cctggacaag gcttgagtg gatgggaggg atcatcccta tctttggtac agcaaactac       180
gcacagaagt tccagggcag agtcacgatt accgcggacg aatccacgag cacagcctac      240
atggagctga gcagcctgag atctgaggac acggccgtgt attactgtgc gagacacccc      300
tacgactact acggtatgga cgtctggggc caagggacaa cggtcaccgt ctcgagcggt      360
ggtggcggtt ctggtggtgg tggtagcggt ggcggtggta gtggcggtgg cggtgctagc      420
gaaattgtgt tgacacagtc tccactctcc ctgcccgtca cccctggaga gccggcctcc      480
atctcctgca ggtctagtca gagcctcctg catagtaatg gatacaacta tttggattgg      540
tacctgcaga agccagggca gtctccacag ctcctgatct atttgggttc taatcgggcc      600
tccggggtcc ctgacaggtt cagtggcagt ggatcaggca cagatttac actgaaaatc       660
agcagagtgg aggctgagga tgttggggtt tattactgca tgcaagctct acaaactccg      720
tggacgttcg gccaagggac caaagtggat atcaaa                                756
```

<210> SEQ ID NO 21
<211> LENGTH: 252
<212> TYPE: PRT
<213> ORGANISM: Artificial Sequence
<220> FEATURE:
<223> OTHER INFORMATION: synthesized sequence

<400> SEQUENCE: 21

```
Gln Val Gln Leu Leu Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Pro Tyr Asp Tyr Tyr Gly Met Asp Val Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Gly Gly Gly Ala Ser Glu Ile Val Leu
    130                 135                 140

Thr Gln Ser Pro Leu Ser Leu Pro Val Thr Pro Gly Glu Pro Ala Ser
145                 150                 155                 160

Ile Ser Cys Arg Ser Ser Gln Ser Leu Leu His Ser Asn Gly Tyr Asn
                165                 170                 175

Tyr Leu Asp Trp Tyr Leu Gln Lys Pro Gly Gln Ser Pro Gln Leu Leu
            180                 185                 190

Ile Tyr Leu Gly Ser Asn Arg Ala Ser Gly Val Pro Asp Arg Phe Ser
```

Gly Ser Gly Ser Gly Thr Asp Phe Thr Leu Lys Ile Ser Arg Val Glu
            210                 215                 220

Ala Glu Asp Val Gly Val Tyr Tyr Cys Met Gln Ala Leu Gln Thr Pro
225                 230                 235                 240

Trp Thr Phe Gly Gln Gly Thr Lys Val Asp Ile Lys
                245                 250

<210> SEQ ID NO 22
<211> LENGTH: 738
<212> TYPE: DNA
<213> ORGANISM: Artificial Sequence
<220> FEATURE:
<223> OTHER INFORMATION: synthesized sequence

<400> SEQUENCE: 22
cgggtgcggc tgcaggagtc gggcccagga ctggtgaagc cttcacagac cctgtccctc    60
acctgcactg tctctggtgg ctccatcagc agtagtaact ggtggagttg ggtccgccag   120
cccccaggga aggggctgga gtggattggg gaaatctatc atagtgggag caccaactac   180
aacccgtccc tcaagagtcg agtcaccata tcagtagaca gtccaagaac cagttctccc   240 tgaagctga gctctgtgac cgccgcggac acggccgtgt attactgtgc gagagatcgg   300
gcgatacgcg atgcttttga tatctggggc caagggacaa cggtcaccgt ctcgagcggt   360
ggtggcggtt ctggtggtgg tggtagcggt ggcggtggta gtggcggtgg cggtgctagc   420
gacatccaga tgacccagtc tccatcgtcc ctgtctgcat ctgtgggaga cagagtcacc   480
atcacttgcc gggcaagtca gagcgttagc agctatttaa attggtatca gcagaaacca   540
gggaaagccc ctaacctcct gatctatgct gcatccagtt tgcaaagtgg ggtcccatca   600
aggttcagtg gcagtggatc tgggacagat ttcactctca ccatcagcag tctgcaacct   660
gaagattttg caacttacta ctgtcaacag agttacagta cccccctttt cggcggaggg   720
accaaactgg agatcaaa                                                 738

<210> SEQ ID NO 23
<211> LENGTH: 246
<212> TYPE: PRT
<213> ORGANISM: Artificial Sequence
<220> FEATURE:
<223> OTHER INFORMATION: synthesized sequence

<400> SEQUENCE: 23

Arg Val Arg Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Arg Ala Ile Arg Asp Ala Phe Asp Ile Trp Gly Gln Gly
            100                 105                 110

Thr Thr Val Thr Val Ser Ser Gly Gly Gly Gly Ser Gly Gly Gly Gly

```
                     115                 120                 125
Ser Gly Gly Gly Gly Ser Gly Gly Gly Ala Ser Asp Ile Gln Met
        130                 135                 140

Thr Gln Ser Pro Ser Ser Leu Ser Ala Ser Val Gly Asp Arg Val Thr
145                 150                 155                 160

Ile Thr Cys Arg Ala Ser Gln Ser Val Ser Ser Tyr Leu Asn Trp Tyr
                165                 170                 175

Gln Gln Lys Pro Gly Lys Ala Pro Asn Leu Leu Ile Tyr Ala Ala Ser
            180                 185                 190

Ser Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Ser Tyr Ser Thr Pro Leu Phe Gly Gly Gly
225                 230                 235                 240

Thr Lys Leu Glu Ile Lys
                245
```

<210> SEQ ID NO 24
<211> LENGTH: 759
<212> TYPE: DNA
<213> ORGANISM: Artificial Sequence
<220> FEATURE:
<223> OTHER INFORMATION: synthesized sequence

<400> SEQUENCE: 24

```
gaagtgcagc tggtgcagtc tgggggaggc gtggtccagc ctggagggtc cctgagactc      60
tcctgtgcag cctctggatt caccttcagt agctatggca tgcactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gaaagtcctg     300
actcctgggc ttactactac ctacggtatg gacgtctggg gccaagggac cacggtcacc     360
gtctcgagcg gtggtggcgg ttctggtggt ggtggtagcg gtggcggtgg tagtggcggt     420
ggcggtgcta gcgaagttat gttgatgcag tctccaggca ccctgtcttt gtctccaggg     480
gaaagagcca ccctctcctg cagggccagt cagagtgtta gcatcagcta cttagcctgg     540
taccagcaga aacctggcca ggctcccagg ctcctcatct atggtacatc tagcagggcc     600
actggcatcc cagacaggtt cagtggcagt gggtctggga cagacttcac tctcaccatc     660
agcagactgg agcctgaaga ttttgcagtg tattactgtc agcagtatgg tagctcaccc     720
ccattcactt tcggccctgg gaccaaactg gaaatcaaa                            759
```

<210> SEQ ID NO 25
<211> LENGTH: 253
<212> TYPE: PRT
<213> ORGANISM: Artificial Sequence
<220> FEATURE:
<223> OTHER INFORMATION: synthesized sequence

<400> SEQUENCE: 25

```
Glu Val Gln Leu Val Gln Ser Gly Gly Gly Val Val Gln Pro Gly Arg
1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
```

```
            35                  40                  45
Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Leu Thr Pro Gly Pro Tyr Tyr Tyr Gly Met Asp Val
            100                 105                 110

Trp Gly Gln Gly Thr Thr Val Thr Val Ser Ser Gly Gly Gly Gly Ser
            115                 120                 125

Gly Gly Gly Gly Ser Gly Gly Gly Ser Gly Gly Gly Ala Ser
        130                 135                 140

Glu Val Met Leu Met Gln Ser Pro Gly Thr Leu Ser Leu Ser Pro Gly
145                 150                 155                 160

Glu Arg Ala Thr Leu Ser Cys Arg Ala Ser Gln Ser Val Ser Ile Ser
                165                 170                 175

Tyr Leu Ala Trp Tyr Gln Gln Lys Pro Gly Gln Ala Pro Arg Leu Leu
            180                 185                 190

Ile Tyr Gly Thr Ser Ser Arg Ala Thr Gly Ile Pro Asp Arg Phe Ser
            195                 200                 205

Gly Ser Gly Ser Gly Thr Asp Phe Thr Leu Thr Ile Ser Arg Leu Glu
        210                 215                 220

Pro Glu Asp Phe Ala Val Tyr Tyr Cys Gln Gln Tyr Gly Ser Ser Pro
225                 230                 235                 240

Pro Phe Thr Phe Gly Pro Gly Thr Lys Leu Glu Ile Lys
                245                 250

<210> SEQ ID NO 26
<211> LENGTH: 768
<212> TYPE: DNA
<213> ORGANISM: Artificial Sequence
<220> FEATURE:
<223> OTHER INFORMATION: synthesized sequence

<400> SEQUENCE: 26
cgggtgcggc tgcaggagtc gggccctggc ctggtgaagt cctcacagac cctgtccctc     60
acctgcagtg tctctggtga ctccatcagt agtggtaaat actactggac ctggatccgg    120
cagcccgccg ggaagggact ggagtggctt gggcgcatcc attccagtgg gtttgcccag    180
tacaacccct ccctcaaggg tcgtctcacc atctctatag acacgtccaa gaaccagttc    240
tccctgaacc tgagctctgt gaccgctgcg gacacggccg tgtattactg cgagacta     300
cccacgccga cgtacttcta cggtatggac gtctggggcc aagggaccac ggtcaccgtc    360
tcgagcggtg gtggcggttc tggtggtggt ggtagcggtg gcggtggtag tggcggtggc    420
ggtgctagcg aaactgtgat gacccagtct ccagactccc tggctgtgtc tctgggcgag    480
agggccacca tcaactgcaa gtccagccag agtatttat acagctccaa caataagaac    540
tacttagctt ggtaccagca gaaaccagga cagcctccta ggctgctcat ttactgggcc    600
tctacccggc aatccggggt ccctgaccga ttcagtggta gcgggtctgg gacagatttc    660
actctcacca tcagcagcct gcggcctgaa gatgtggctg tttattactg tcaacaatat    720
tatggtgctc cgatcacctt cggccaaggg acacgactgg agattaaa                 768

<210> SEQ ID NO 27
```

<211> LENGTH: 256
<212> TYPE: PRT
<213> ORGANISM: Artificial Sequence
<220> FEATURE:
<223> OTHER INFORMATION: synthesized sequence

<400> SEQUENCE: 27

```
Arg Val Arg Leu Gln Glu Ser Gly Pro Gly Leu Val Lys Ser Ser Gln
 1               5                  10                  15
Thr Leu Ser Leu Thr Cys Ser Val Ser Gly Asp Ser Ile Ser Ser Gly
            20                  25                  30
Lys Tyr Tyr Trp Thr Trp Ile Arg Gln Pro Ala Gly Lys Gly Leu Glu
        35                  40                  45
Trp Leu Gly Arg Ile His Ser Ser Gly Phe Ala Gln Tyr Asn Pro Ser
 50                  55                  60
Leu Lys Gly Arg Leu Thr Ile Ser Ile Asp Thr Ser Lys Asn Gln Phe
 65                  70                  75                  80
Ser Leu Asn Leu Ser Ser Val Thr Ala Ala Asp Thr Ala Val Tyr Tyr
                85                  90                  95
Cys Ala Arg Leu Pro Thr Pro Thr Tyr Phe Tyr Gly Met Asp Val Trp
            100                 105                 110
Gly Gln Gly Thr Thr Val Thr Val Ser Ser Gly Gly Gly Ser Gly
        115                 120                 125
Gly Gly Gly Ser Gly Gly Gly Ser Gly Gly Gly Ala Ser Glu
    130                 135                 140
Thr Val Met Thr Gln Ser Pro Asp Ser Leu Ala Val Ser Leu Gly Glu
145                 150                 155                 160
Arg Ala Thr Ile Asn Cys Lys Ser Ser Gln Ser Ile Leu Tyr Ser Ser
                165                 170                 175
Asn Asn Lys Asn Tyr Leu Ala Trp Tyr Gln Gln Lys Pro Gly Gln Pro
            180                 185                 190
Pro Arg Leu Leu Ile Tyr Trp Ala Ser Thr Arg Gln Ser Gly Val Pro
        195                 200                 205
Asp Arg Phe Ser Gly Ser Gly Ser Gly Thr Asp Phe Thr Leu Thr Ile
 210                 215                 220
Ser Ser Leu Arg Pro Glu Asp Val Ala Val Tyr Tyr Cys Gln Gln Tyr
225                 230                 235                 240
Tyr Gly Ala Pro Ile Thr Phe Gly Gln Gly Thr Arg Leu Glu Ile Lys
                245                 250                 255
```

<210> SEQ ID NO 28
<211> LENGTH: 759
<212> TYPE: DNA
<213> ORGANISM: Artificial Sequence
<220> FEATURE:
<223> OTHER INFORMATION: synthesized sequence

<400> SEQUENCE: 28

| caggtgcagc tggtggagtc tgggggaggc ttggtacagc ctggccggtc cctgagactc | 60 |
| tcctgtgtag cctctggatt cacctttgat gatcatgcca tgcactgggt caggcaaact | 120 |
| ccagagaagg gcctggagtg gtctcaggt attagttgga atggaggtga catacgctat | 180 |
| gcggactctg tgaagggccg attcatcatc tccagagaca acgccaagaa ctccctgcat | 240 |
| ctgcaaatga acagtctgag aggtgaagac acggctgtgt attactgtgc gagagatggt | 300 |
| ggatatagtg ttcttagggc ttttgatatc tggggccaag gaccacggt caccgtctcg | 360 |
| agcggtggtg gcggttctgg tggtggtggt agcggtggcg gtggtagtgg cggtggcggt | 420 |

```
gctagccagt ctgtgttgac gcagccgccc tcagtgtctg gggcccgggg gcagagggtc    480
accatctcct gcactgggag cagctccaac atcggggcag ttatgatgt acactggtac     540 cagcagcttc caggaacagc ccccaaactc ctcatctatg gtaacagcaa tcggccctca    600
ggggtccctg accgattctc tggctccaag tctggcacct cagcctccct ggccatcact    660
gggctccagg ctgaggatga ggctgattat tactgccagt cctatgacag cagcctgagt    720
ggttgggtgt tcggcggagg aacccagctg atcattta                            759
```

```
<210> SEQ ID NO 29
<211> LENGTH: 253
<212> TYPE: PRT
<213> ORGANISM: Artificial Sequence
<220> FEATURE:
<223> OTHER INFORMATION: synthesized sequence

<400> SEQUENCE: 29
```

```
Gln Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asp Asp His
            20                  25                  30

Ala Met His Trp Val Arg Gln Thr Pro Glu Lys Gly Leu Glu Trp Val
        35                  40                  45

Ser Gly Ile Ser Trp Asn Gly Gly Asp Ile Arg Tyr Ala Asp Ser Val
    50                  55                  60

Lys Gly Arg Phe Ile Ile Ser Arg Asp Asn Ala Lys Asn Ser Leu His
65                  70                  75                  80

Leu Gln Met Asn Ser Leu Arg Gly Glu Asp Thr Ala Val Tyr Tyr Cys
                85                  90                  95

Ala Arg Asp Gly Gly Tyr Ser Val Leu Arg Ala Phe Asp Ile Trp Gly
            100                 105                 110

Gln Gly Thr Thr Val Thr Val Ser Ser Gly Gly Gly Ser Gly Gly
        115                 120                 125

Gly Gly Ser Gly Gly Gly Gly Ser Gly Gly Gly Ala Ser Gln Ser
    130                 135                 140

Val Leu Thr Gln Pro Pro Ser Val Ser Gly Ala Pro Gly Gln Arg Val
145                 150                 155                 160

Thr Ile Ser Cys Thr Gly Ser Ser Asn Ile Gly Ala Gly Tyr Asp
                165                 170                 175

Val His Trp Tyr Gln Gln Leu Pro Gly Thr Ala Pro Lys Leu Leu Ile
            180                 185                 190

Tyr Gly Asn Ser Asn Arg Pro Ser Gly Val Pro Asp Arg Phe Ser Gly
        195                 200                 205

Ser Lys Ser Gly Thr Ser Ala Ser Leu Ala Ile Thr Gly Leu Gln Ala
    210                 215                 220

Glu Asp Glu Ala Asp Tyr Tyr Cys Gln Ser Tyr Asp Ser Ser Leu Ser
225                 230                 235                 240

Gly Trp Val Phe Gly Gly Gly Thr Gln Leu Ile Ile Leu
                245                 250
```

```
<210> SEQ ID NO 30
<211> LENGTH: 750
<212> TYPE: DNA
<213> ORGANISM: Artificial Sequence
<220> FEATURE:
<223> OTHER INFORMATION: synthesized sequence
```

<400> SEQUENCE: 30

```
cgggtgcggc tgcaggagtc gggccctggc ctggtgaagt cctcacagac cctgtccctc    60
acctgcagtg tctctggtga ctccatcagt agtggtaaat actactggac ctggatccgg   120
cagcccgccg ggaagggact ggagtggctt gggcgcatcc attccagtgg gtttgcccag   180
tacaacccct ccctcaaggg tcgactcacc atatcagtgg acacgcgcaa gaatgagttc   240
tccctgaagc tgagctctgt gaccgctgcg gacacggccg tgtattactg tgcggctacg   300
gtggtaactc cggtcgactc tgcttttgat atctggggcc aagggacaat ggtcaccgtc   360
tcgagcggtg gtggcggttc tggtggtggt ggtagcggtg gcggtggtag tggcggtggc   420
ggtgctagcg atacagtgat gacacagtct ccatcctccc tgtctgcatc tgtaggagac   480
agagtcacca tcacttgccg ggcaagtcag agcattagca gctatttaaa ttggtatcag   540
cagaaaccag ggaaagcccc taagctcctg atctatgctg catccagttt gcaaagtggg   600
gtcccatcaa ggttcagtgg cagtggatct gggacagatt tcactctcac catcagcagt   660
ctgcaacctg aagattttgc aacttactac tgtcaacaga gttacagtac cccgctcact   720
ttcggcggag ggaccaaggt ggagatcaaa                                    750
```

<210> SEQ ID NO 31
<211> LENGTH: 250
<212> TYPE: PRT
<213> ORGANISM: Artificial Sequence
<220> FEATURE:
<223> OTHER INFORMATION: synthesized sequence

<400> SEQUENCE: 31

Arg Val Arg Leu Gln Glu Ser Gly Pro Gly Leu Val Lys Ser Ser Gln
1               5                   10                  15

Thr Leu Ser Leu Thr Cys Ser Val Ser Gly Asp Ser Ile Ser Ser Gly
            20                  25                  30

Lys Tyr Tyr Trp Thr Trp Ile Arg Gln Pro Ala Gly Lys Gly Leu Glu
        35                  40                  45

Trp Leu Gly Arg Ile His Ser Ser Gly Phe Ala Gln Tyr Asn Pro Ser
    50                  55                  60

Leu Lys Gly Arg Leu Thr Ile Ser Val Asp Thr Arg Lys Asn Glu Phe
65                  70                  75                  80

Ser Leu Lys Leu Ser Ser Val Thr Ala Ala Asp Thr Ala Val Tyr Tyr
                85                  90                  95

Cys Ala Ala Thr Val Val Thr Pro Val Asp Ser Ala Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Ser Gly Gly Gly Ala Ser Asp
    130                 135                 140

Thr Val Met Thr Gln Ser Pro Ser Ser Leu Ser Ala Ser Val Gly Asp
145                 150                 155                 160

Arg Val Thr Ile Thr Cys Arg Ala Ser Gln Ser Ile Ser Ser Tyr Leu
                165                 170                 175

Asn Trp Tyr Gln Gln Lys Pro Gly Lys Ala Pro Lys Leu Leu Ile Tyr
            180                 185                 190

Ala Ala Ser Ser Leu Gln Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Gln Gln Ser Tyr Ser Thr Pro Leu Thr
225                 230                 235                 240

Phe Gly Gly Gly Thr Lys Val Glu Ile Lys
            245                 250

<210> SEQ ID NO 32
<211> LENGTH: 762
<212> TYPE: DNA
<213> ORGANISM: Artificial Sequence
<220> FEATURE:
<223> OTHER INFORMATION: synthesized sequence

<400> SEQUENCE: 32
gaggtgcagc tggaggagtc tgggggaggc gtggtccagc ctggagggtc cctgagactc      60
tcctgtgcag cctctggatt cacctttagc agctatgcca tgagctgggt ccgccaggct     120
ccagggaagg gctggagtg gtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaagattac     300
tatgatagta gtggttatt cgctgggggt gctgcttttg atatctgggg ccaagggaca     360
acggtcaccg tctcgagcgg tggtggcggt tctggtggtg gtggtagcgg tggcggtggt     420
agtggcggtg gcggtgctag cgaaacgaca ctcacgcagt ctccagccac cctgtctgtg     480
tctccagggg acagcgccac cctctcctgc agggccagtc gctatgttgg caacaacttg     540
gcctggtacc accagaagcc tggccaggct cccaggctcc tcatctatga cgcatccacc     600
agggccactg gtgtcccagg cagattcagt ggcagtgggt ttgggacaga cttcactctc     660
accattccca gcctgaggtc tgagaatttt gcagtttatt tctgtcagca atatgataac     720
tggcccctga ccttcggcca aggacacga ctggagatta aa                        762

<210> SEQ ID NO 33
<211> LENGTH: 254
<212> TYPE: PRT
<213> ORGANISM: Artificial Sequence
<220> FEATURE:
<223> OTHER INFORMATION: synthesized sequence

<400> SEQUENCE: 33

Glu Val Gln Leu Glu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Tyr Asp Ser Ser Gly Tyr Phe Ala Gly Gly Ala Ala
            100                 105                 110

Phe Asp Ile Trp Gly Gln Gly Thr Thr Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ala Ser Glu Thr Thr Leu Thr Gln Ser Pro Ala Thr Leu Ser Val
145                 150                 155                 160

Ser Pro Gly Asp Ser Ala Thr Leu Ser Cys Arg Ala Ser Arg Tyr Val
            165                 170                 175

Gly Asn Asn Leu Ala Trp Tyr His Gln Lys Pro Gly Gln Ala Pro Arg
        180                 185                 190

Leu Leu Ile Tyr Asp Ala Ser Thr Arg Ala Thr Gly Val Pro Gly Arg
    195                 200                 205

Phe Ser Gly Ser Gly Phe Gly Thr Asp Phe Thr Leu Thr Ile Ser Ser
210                 215                 220

Leu Arg Ser Glu Asn Phe Ala Val Tyr Phe Cys Gln Gln Tyr Asp Asn
225                 230                 235                 240

Trp Pro Leu Thr Phe Gly Gln Gly Thr Arg Leu Glu Ile Lys
                245                 250

<210> SEQ ID NO 34
<211> LENGTH: 759
<212> TYPE: DNA
<213> ORGANISM: Artificial Sequence
<220> FEATURE:
<223> OTHER INFORMATION: synthesized sequence

<400> SEQUENCE: 34
gaggttcagc tggtgcagtc tggggctgag gtgaagaagc tggggcctc  agtgaaggtc      60 tcctgcaagg tttccggata caccctcact gaattatcca tgcactgggt gcgacaggct     120
cctggaaaag gcttgagtg  gatgggaggt tttgatcctg aagatggtga acaatctac     180 gcacagaagt tccagggcag agtcaccatg accgaggaca tcctacaga cacagcctac     240 atggagctga gcagcctgag atctgaggac acggccgtgt attactgtgc aacagagtat     300
agtggtggta gctactacta ctactactac ggtatggacg tctggggcca agggaccacg     360
gtcaccgtct cgagcggtgg tggcggttct ggtggtggtg gtagcggtgg cggtggtagt     420
ggcggtggcg gtgctagcga aattgtgttg acccagactc catcctccct gtctgcatct     480
gtaggagaca gagtcaccat cacttgccgg gcaagtcaga gcattagcag ctatttaaat     540
tggtatcagc agaaaccagg gaaagcccct aagctcctga tctatgctgc atccagtttg     600
caaagtgggg tcccatcaag gttcagtggc agtggatctg ggacagattt cactctcacc     660
atcagcagtc tgcaacctga agattttgca acttactact gtcaacagag ttacagtacc     720
ccgtacactt ttggccaggg gaccaagctg gagatcaaa                           759

<210> SEQ ID NO 35
<211> LENGTH: 253
<212> TYPE: PRT
<213> ORGANISM: Artificial Sequence
<220> FEATURE:
<223> OTHER INFORMATION: synthesized sequence

<400> SEQUENCE: 35

Glu Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Tyr Ser Gly Gly Ser Tyr Tyr Tyr Tyr Tyr Gly Met
            100                 105                 110

Asp Val Trp Gly Gln Gly Thr Thr Val Thr Val Ser Ser Gly Gly Gly
            115                 120                 125

Gly Ser Gly Gly Gly Gly Ser Gly Gly Gly Ser Gly Gly Gly Gly
    130                 135                 140

Ala Ser Glu Ile Val Leu Thr Gln Thr Pro Ser Ser Leu Ser Ala Ser
145                 150                 155                 160

Val Gly Asp Arg Val Thr Ile Thr Cys Arg Ala Ser Gln Ser Ile Ser
                165                 170                 175

Ser Tyr Leu Asn Trp Tyr Gln Gln Lys Pro Gly Lys Ala Pro Lys Leu
            180                 185                 190

Leu Ile Tyr Ala Ala Ser Ser Leu Gln Ser Gly Val Pro Ser Arg Phe
        195                 200                 205

Ser Gly Ser Gly Ser Gly Thr Asp Phe Thr Leu Thr Ile Ser Ser Leu
    210                 215                 220

Gln Pro Glu Asp Phe Ala Thr Tyr Tyr Cys Gln Gln Ser Tyr Ser Thr
225                 230                 235                 240

Pro Tyr Thr Phe Gly Gln Gly Thr Lys Leu Glu Ile Lys
                245                 250

<210> SEQ ID NO 36
<211> LENGTH: 759
<212> TYPE: DNA
<213> ORGANISM: Artificial Sequence
<220> FEATURE:
<223> OTHER INFORMATION: synthesized sequence

<400> SEQUENCE: 36
cagctgcagc tgcaggagtc gggccctggc ctggtgaagt cctcacagac cctgtccctc      60
acctgcagtg tctctggtga ctccatcagt agtggtaaat actactggac ctggatccgg     120
cagcccgccg ggaagggact ggagtggctt gggcgcatcc attccagtgg gtttgcccag     180
tacaacccct ccctcaaggg tcgactcacc atatcagtgg acacgcgcaa gaatgagttc     240
tccctaaaaa tgacctctgt gactgccgca gacacggccg tctattactg tgcgagaggc     300
ggctggaacg accccttga ctcctggggc cagggaaccc tggtcactgt ctcgagcggt      360
ggtggcggtt ctggtggtgg tggtagcggt ggcggtggta gtggcggtgg cggtgctagc     420
gatatccaga tgacccagtc tccagactcc ctggctgtgt ctctgggcga gagggccacc     480
atcaactgca agtccagcca gagtgtttta tacagctcca acaataagaa ctacttagct     540
tggtaccagc agaaaccagg acagcctcct aagctgctca tttactgggc atctacccgg     600
gaatccgggg tccctgaccg attcagtgtc agcgggtctg ggacagattt cactctcacc     660
atcagcagcc tgcatgctga agatgtggca gtttattact gtcagcaata ttatagtact     720
cctatcactt tcggccctgg gaccaagctg gagatcaaa                           759

<210> SEQ ID NO 37
<211> LENGTH: 253
<212> TYPE: PRT
<213> ORGANISM: Artificial Sequence
<220> FEATURE:

<223> OTHER INFORMATION: synthesized sequence

<400> SEQUENCE: 37

```
Gln Leu Gln Leu Gln Glu Ser Gly Pro Gly Leu Val Lys Ser Ser Gln
1               5                   10                  15
Thr Leu Ser Leu Thr Cys Ser Val Ser Gly Asp Ser Ile Ser Ser Gly
            20                  25                  30
Lys Tyr Tyr Trp Thr Trp Ile Arg Gln Pro Ala Gly Lys Gly Leu Glu
        35                  40                  45
Trp Leu Gly Arg Ile His Ser Ser Gly Phe Ala Gln Tyr Asn Pro Ser
    50                  55                  60
Leu Lys Gly Arg Leu Thr Ile Ser Val Asp Thr Arg Lys Asn Glu Phe
65                  70                  75                  80
Ser Leu Lys Met Thr Ser Val Thr Ala Ala Asp Thr Ala Val Tyr Tyr
                85                  90                  95
Cys Ala Arg Gly Gly Trp Asn Asp Pro Phe Asp Ser Trp Gly Gln Gly
            100                 105                 110
Thr Leu Val Thr Val Ser Ser Gly Gly Gly Ser Gly Gly Gly Gly
        115                 120                 125
Ser Gly Gly Gly Ser Gly Gly Gly Ala Ser Asp Ile Gln Met
    130                 135                 140
Thr Gln Ser Pro Asp Ser Leu Ala Val Ser Leu Gly Glu Arg Ala Thr
145                 150                 155                 160
Ile Asn Cys Lys Ser Ser Gln Ser Val Leu Tyr Ser Ser Asn Asn Lys
                165                 170                 175
Asn Tyr Leu Ala Trp Tyr Gln Gln Lys Pro Gly Gln Pro Pro Lys Leu
            180                 185                 190
Leu Ile Tyr Trp Ala Ser Thr Arg Glu Ser Gly Val Pro Asp Arg Phe
        195                 200                 205
Ser Val Ser Gly Ser Gly Thr Asp Phe Thr Leu Thr Ile Ser Ser Leu
    210                 215                 220
His Ala Glu Asp Val Ala Val Tyr Tyr Cys Gln Gln Tyr Tyr Ser Thr
225                 230                 235                 240
Pro Ile Thr Phe Gly Pro Gly Thr Lys Leu Glu Ile Lys
                245                 250
```

<210> SEQ ID NO 38
<211> LENGTH: 744
<212> TYPE: DNA
<213> ORGANISM: Artificial Sequence
<220> FEATURE:
<223> OTHER INFORMATION: synthesized sequence

<400> SEQUENCE: 38

```
caggtgcagc tacaggagtc gggcccagga ctggtgaagc cttcggagac cctgtccctc    60
acctgcactg tctctggtta ctccatcagc agtggttact actggggctg atccggcag   120
cccccaggga aggggctgga gtggattggg agtatctatc atagtgggag cacctactac   180
aacccgtccc tcaagagtcg agtcaccata tcagtagaca cgtccaagaa ccagttctcc   240
ctgaagctga gctctgtgac cgccgcagac acggccgtgt attactgtgc gagagaccta   300
caggattggt tcgaccctg gggccaggga accctggtca ccgtctcgag cggtggtggc   360
ggttctggtg gtggtggtag cggtggcggt ggtagtggcg gtggcggtgc tagcctggct   420
gtgctgactc acgcaccctc agcgtctggg acccccgggc agagagtcac catctcttgt   480
tctggaagca gtccaacat cggaagtaat tctgttaact ggtatcagca cctccccgga   540
```

```
acggccccca aactcctcat acatactaat gatcagcggc cctcagggt ccctgaccga      600 ttcgctggct ccaagtctgg cacctcagca tccttgacca tcagtggcct caggcctgaa      660
gatgaggcgg attattactg tgcaacatgg gatgacagca tgagtggtcc ggtgttcggc      720
ggtgggaccg agctgaccgt ccta                                            744
```

<210> SEQ ID NO 39
<211> LENGTH: 248
<212> TYPE: PRT
<213> ORGANISM: Artificial Sequence
<220> FEATURE:
<223> OTHER INFORMATION: synthesized sequence

<400> SEQUENCE: 39

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Leu Gln Asp Trp Phe Asp Pro Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Gly Ala Ser Leu Ala Val Leu Thr His
130                 135                 140

Ala Pro Ser Ala Ser Gly Thr Pro Gly Gln Arg Val Thr Ile Ser Cys
145                 150                 155                 160

Ser Gly Ser Lys Ser Asn Ile Gly Ser Asn Ser Val Asn Trp Tyr Gln
                165                 170                 175

His Leu Pro Gly Thr Ala Pro Lys Leu Leu Ile His Thr Asn Asp Gln
            180                 185                 190

Arg Pro Ser Gly Val Pro Asp Arg Phe Ala Gly Ser Lys Ser Gly Thr
        195                 200                 205

Ser Ala Ser Leu Thr Ile Ser Gly Leu Arg Pro Glu Asp Glu Ala Asp
    210                 215                 220

Tyr Tyr Cys Ala Thr Trp Asp Asp Ser Met Ser Gly Pro Val Phe Gly
225                 230                 235                 240

Gly Gly Thr Glu Leu Thr Val Leu
                245
```

<210> SEQ ID NO 40
<211> LENGTH: 372
<212> TYPE: DNA
<213> ORGANISM: Artificial Sequence
<220> FEATURE:
<223> OTHER INFORMATION: synthesized sequence

<400> SEQUENCE: 40

```
gaggttcagc tgttggagtc tggagctgag gtgaagaagc ctggggcctc agtgaaggtc      60
```

```
tcctgcaagg cttctggtta cacctttacc agctatggta tcagctgggt gcgacaggcc    120
cctggacaag ggcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gagagatggc    300
tggtgggagc tactacgtcc cgatgatgct tttgatatct ggggccaagg gacaacggtc    360
accgtctcga gc                                                        372
```

<210> SEQ ID NO 41
<211> LENGTH: 124
<212> TYPE: PRT
<213> ORGANISM: Artificial Sequence
<220> FEATURE:
<223> OTHER INFORMATION: synthesized sequence

<400> SEQUENCE: 41

```
Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Trp Trp Glu Leu Leu Arg Pro Asp Asp Ala Phe Asp
            100                 105                 110

Ile Trp Gly Gln Gly Thr Thr Val Thr Val Ser Ser
        115                 120
```

<210> SEQ ID NO 42
<211> LENGTH: 327
<212> TYPE: DNA
<213> ORGANISM: Artificial Sequence
<220> FEATURE:
<223> OTHER INFORMATION: synthesized sequence

<400> SEQUENCE: 42

```
cagcttgtgc tgactcagtc gccctcagtg tccgtgtccc caggacagac agccagcatc     60
acctgctctg gagataagtt gggagataaa tatgcttact ggtatcagca gaagccaggc    120
caggcccctg tgctggtcat ctattatgat agcgaccggc cctcagggat ccctgagcga    180
ttctctggct ccaactctgg gaacacggcc accctgacca tcagcagggt cgaagccggg    240
gatgaggccg actattactg tcaggtgtgg gatagtagta gtgatcaagt ggtattcggc    300
ggaggcaccc agctgaccgt cctcggt                                        327
```

<210> SEQ ID NO 43
<211> LENGTH: 109
<212> TYPE: PRT
<213> ORGANISM: Artificial Sequence
<220> FEATURE:
<223> OTHER INFORMATION: synthesized sequence

<400> SEQUENCE: 43

```
Gln Leu Val Leu Thr Gln Ser Pro Ser Val Ser Val Ser Pro Gly Gln
```

```
1               5                  10                 15
Thr Ala Ser Ile Thr Cys Ser Gly Asp Lys Leu Gly Asp Lys Tyr Ala
                20                  25                  30
Tyr Trp Tyr Gln Gln Lys Pro Gly Gln Ala Pro Val Leu Val Ile Tyr
                35                  40                  45
Tyr Asp Ser Asp Arg Pro Ser Gly Ile Pro Glu Arg Phe Ser Gly Ser
                50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Ser Ser Asp Gln
                85                  90                  95
Val Val Phe Gly Gly Gly Thr Gln Leu Thr Val Leu Gly
                100                 105
```

<210> SEQ ID NO 44
<211> LENGTH: 363
<212> TYPE: DNA
<213> ORGANISM: Artificial Sequence
<220> FEATURE:
<223> OTHER INFORMATION: synthesized sequence

<400> SEQUENCE: 44

```
gaggtgcagc tggtggagtc tgggggaggc gtggtccagc ctggagggtc cctgagactc    60
tcctgtgcag cctctggatt caccttcagt aattatgcta tgcactgggt ccgccaggct   120
ccaggcaagg ggctggagtg ggtggcagtt atatcatatg atggaagcga taaatactac   180
gcagactccg tgaagggccg attcaccatc tccagagaca attccaagaa cacgctgtat   240
ctgcaaatga aaagcctgag agctgaggac acggctgtgt attactgtgc gagatcaatc   300
gggtttcttg agagcgatgc ttttgatatc tggggccaag ggaccacggt caccgtctcg   360
agc                                                                 363
```

<210> SEQ ID NO 45
<211> LENGTH: 121
<212> TYPE: PRT
<213> ORGANISM: Artificial Sequence
<220> FEATURE:
<223> OTHER INFORMATION: synthesized sequence

<400> SEQUENCE: 45

```
Glu Val Gln Leu Val Glu Ser Gly Gly Gly Val Val Gln Pro Gly Arg
1               5                  10                  15
Ser Leu Arg Leu Ser Cys Ala Ala Ser Gly Phe Thr Phe Ser Asn Tyr
                20                  25                  30
Ala Met His Trp Val Arg Gln Ala Pro Gly Lys Gly Leu Glu Trp Val
                35                  40                  45
Ala Val Ile Ser Tyr Asp Gly Ser Asp Lys Tyr Tyr Ala Asp Ser Val
                50                  55                  60
Lys Gly Arg Phe Thr Ile Ser Arg Asp Asn Ser Lys Asn Thr Leu Tyr
65                  70                  75                  80
Leu Gln Met Lys Ser Leu Arg Ala Glu Asp Thr Ala Val Tyr Tyr Cys
                85                  90                  95
Ala Arg Ser Ile Gly Phe Leu Glu Ser Asp Ala Phe Asp Ile Trp Gly
                100                 105                 110
Gln Gly Thr Thr Val Thr Val Ser Ser
                115                 120
```

<210> SEQ ID NO 46
<211> LENGTH: 321
<212> TYPE: DNA
<213> ORGANISM: Artificial Sequence
<220> FEATURE:
<223> OTHER INFORMATION: synthesized sequence

<400> SEQUENCE: 46

```
gacatcgtgc tgacacagtc tccatcctcc ctgtctgcat ctgtaggaga cagagtcacc      60
atcacttgcc aggcgagtca cggcatttcc aacttttta attggtatca gcagaaacca     120
ggaaaagccc ctaagctcct catctacgat gcatccactt tggaaacagg ggtcccatca     180
aggttcagtg gaagtggatc tgggacagat tttagattca ccatcagcag cctgcagcct     240
gaagatattg caacatatta ctgtcaacaa tttgataatc tcccgatcac cttcggccaa     300
gggacacgac tggagattaa a                                               321
```

<210> SEQ ID NO 47
<211> LENGTH: 107
<212> TYPE: PRT
<213> ORGANISM: Artificial Sequence
<220> FEATURE:
<223> OTHER INFORMATION: synthesized sequence

<400> SEQUENCE: 47

Asp Ile Val Leu Thr Gln Ser Pro Ser Leu Ser Ala Ser Val Gly
1               5                   10                  15

Asp Arg Val Thr Ile Thr Cys Gln Ala Ser His Gly Ile Ser Asn Phe
            20                  25                  30

Leu Asn Trp Tyr Gln Gln Lys Pro Gly Lys Ala Pro Lys Leu Leu Ile
        35                  40                  45

Tyr Asp Ala Ser Thr Leu Glu Thr Gly Val Pro Ser Arg Phe Ser Gly
    50                  55                  60

Ser Gly Ser Gly Thr Asp Phe Arg Phe Thr Ile Ser Ser Leu Gln Pro
65                  70                  75                  80

Glu Asp Ile Ala Thr Tyr Tyr Cys Gln Gln Phe Asp Asn Leu Pro Ile
                85                  90                  95

Thr Phe Gly Gln Gly Thr Arg Leu Glu Ile Lys
            100                 105

<210> SEQ ID NO 48
<211> LENGTH: 354
<212> TYPE: DNA
<213> ORGANISM: Artificial Sequence
<220> FEATURE:
<223> OTHER INFORMATION: synthesized sequence

<400> SEQUENCE: 48

```
gaggtgcagc tgttgcagtc tgggggaggc ttggtacagc ctggagggtc cctgagactc      60
tcctgtgcag cctctggatt caccttcagt agttatgaaa tgaactgggt ccgccaggct     120
ccagggaagg ggctggagtg ggtttcatac attagtagta gtggtagtac catatactac     180
gcagactctg tgaagggccg attcaccatc tccagagaca acgccaagaa ctcactgtat     240
ctgcaaatga acagcctgag agccgaggac acggctgtgt attactgtgc gagagttgga     300
ctccttgatg cttttgatat ctggggccaa gggaccatgg tcaccgtctc gagc           354
```

<210> SEQ ID NO 49
<211> LENGTH: 118
<212> TYPE: PRT
<213> ORGANISM: Artificial Sequence
<220> FEATURE:
<223> OTHER INFORMATION: synthesized sequence

<400> SEQUENCE: 49

```
Glu Val Gln Leu Leu Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Leu Asp Ala Phe Asp Ile Trp Gly Gln Gly Thr
            100                 105                 110

Met Val Thr Val Ser Ser
        115
```

<210> SEQ ID NO 50
<211> LENGTH: 333
<212> TYPE: DNA
<213> ORGANISM: Artificial Sequence
<220> FEATURE:
<223> OTHER INFORMATION: synthesized sequence

<400> SEQUENCE: 50

```
cagtctgtct tgacgcagcc gccctcagtg tctgcggccc caggacagaa ggtcaccatc    60
tcctgctctg gaagcagctc caacattggg aataattatg tatcctggta ccagctgatc   120
ccagaaaaag cccccagact cctcatttat gacgatgata gcgaccctc cgggattcct    180
gaccgattct ctggctccca gtctggcacg tcagccaccc tgggcatcac cggactccag   240
actggggacg aggccgatta tttctgcgga acatgggata cagcctgag tggtgcggta    300
ttcggcggag gaacccagct gatcatttta ggt                                333
```

<210> SEQ ID NO 51
<211> LENGTH: 111
<212> TYPE: PRT
<213> ORGANISM: Artificial Sequence
<220> FEATURE:
<223> OTHER INFORMATION: synthesized sequence

<400> SEQUENCE: 51

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Leu Ile Pro Glu Lys Ala Pro Arg Leu Leu
        35                  40                  45

Ile Tyr Asp Asp Asp Lys Arg Pro Ser Gly Ile Pro Asp Arg Phe Ser
    50                  55                  60

Gly Ser Gln Ser Gly Thr Ser Ala Thr Leu Gly Ile Thr Gly Leu Gln
65                  70                  75                  80

Thr Gly Asp Glu Ala Asp Tyr Phe Cys Gly Thr Trp Asp Asn Ser Leu
                85                  90                  95
```

```
Ser Gly Ala Val Phe Gly Gly Gly Thr Gln Leu Ile Ile Leu Gly
            100                 105                 110
```

<210> SEQ ID NO 52
<211> LENGTH: 363
<212> TYPE: DNA
<213> ORGANISM: Artificial Sequence
<220> FEATURE:
<223> OTHER INFORMATION: synthesized sequence

<400> SEQUENCE: 52

```
gaggtgcatc tggtagagtc tgggggaggc gtggtccagc ctggaggtc cctgagactc      60
tcctgtgcag cctctggatt caccttcagt aactatgcta tgcactgggt ccgccaggct    120
ccaggcaagg ggctggagtg gtggcagtt atatcatatg atggaaacaa tcaatactac    180
gcagactccg tgaagggccg attcaccatc tccagagaca attccaagaa cacgctgtat    240
ctgcaaatga acagcctgag agctgaggac acggctgtgt tttactgtgc gagatcaatc    300
ggattccttg agagcgatgc ttttgatatc tggggccaag gacaacggt caccgtctcg    360
agc                                                                  363
```

<210> SEQ ID NO 53
<211> LENGTH: 121
<212> TYPE: PRT
<213> ORGANISM: Artificial Sequence
<220> FEATURE:
<223> OTHER INFORMATION: synthesized sequence

<400> SEQUENCE: 53

```
Glu Val His Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Phe Tyr Cys
                85                  90                  95

Ala Arg Ser Ile Gly Phe Leu Glu Ser Asp Ala Phe Asp Ile Trp Gly
            100                 105                 110

Gln Gly Thr Thr Val Thr Val Ser Ser
        115                 120
```

<210> SEQ ID NO 54
<211> LENGTH: 324
<212> TYPE: DNA
<213> ORGANISM: Artificial Sequence
<220> FEATURE:
<223> OTHER INFORMATION: synthesized sequence

<400> SEQUENCE: 54

```
gaaatagtgt tgatgcagtc tccaggcacc ctgtctttgt ctccagggga aagagccacc     60
ctctcctgca gggccagtca agttttagt gacgggtcct tagcctggta ccagcagaaa    120
cctggccagc ctcccagact cgtcatctat gatgcatcga gcgggccac tggcatccct    180
gacaggttca gtggcagtag gtctgggaca gagttcactc tcaccatcag cagcctgcag    240
```
tctgaagatt tgcagttta ttcctgtcag cagtattata actggcctcc caccttcggc    300
caagggacac gactggagat taaa    324

<210> SEQ ID NO 55
<211> LENGTH: 108
<212> TYPE: PRT
<213> ORGANISM: Artificial Sequence
<220> FEATURE:
<223> OTHER INFORMATION: synthesized sequence

<400> SEQUENCE: 55

Glu Ile Val Leu Met Gln Ser Pro Gly Thr Leu Ser Leu Ser Pro Gly
1               5                   10                  15

Glu Arg Ala Thr Leu Ser Cys Arg Ala Ser Gln Ser Phe Ser Asp Gly
            20                  25                  30

Ser Leu Ala Trp Tyr Gln Gln Lys Pro Gly Gln Pro Pro Arg Leu Val
        35                  40                  45

Ile Tyr Asp Ala Ser Lys Arg Ala Thr Gly Ile Pro Asp Arg Phe Ser
    50                  55                  60

Gly Ser Arg Ser Gly Thr Glu Phe Thr Leu Thr Ile Ser Ser Leu Gln
65                  70                  75                  80

Ser Glu Asp Phe Ala Val Tyr Ser Cys Gln Gln Tyr Tyr Asn Trp Pro
                85                  90                  95

Pro Thr Phe Gly Gln Gly Thr Arg Leu Glu Ile Lys
            100                 105

<210> SEQ ID NO 56
<211> LENGTH: 357
<212> TYPE: DNA
<213> ORGANISM: Artificial Sequence
<220> FEATURE:
<223> OTHER INFORMATION: synthesized sequence

<400> SEQUENCE: 56
cgggtgcggc tgcaggagtc gggcccagga ctggtgaagc cttcacagac cctgtccctc     60
acctgcactg tctctggtgg ctccatcagc agtagtaact ggtggagttg ggtccgccag    120
cccccaggga aggggctgga gtggattggg gaaatctatc atagtgggag caccaactac    180
aacccgtccc tcaagagtcg agtcaccata tcagtagaca gtccaagaa ccagttctcc    240 ctgaagctga gctctgtgac cgccgcggac acggccgtgt attactgtgc gagagatcgg    300
gcgatacgcg atgctttga tatctggggc caagggacaa cggtcaccgt ctcgagc       357

<210> SEQ ID NO 57
<211> LENGTH: 119
<212> TYPE: PRT
<213> ORGANISM: Artificial Sequence
<220> FEATURE:
<223> OTHER INFORMATION: synthesized sequence

<400> SEQUENCE: 57

Arg Val Arg Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

```
Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Asp Arg Ala Ile Arg Asp Ala Phe Asp Ile Trp Gly Gln Gly
                100                 105                 110

Thr Thr Val Thr Val Ser Ser
            115

<210> SEQ ID NO 58
<211> LENGTH: 318
<212> TYPE: DNA
<213> ORGANISM: Artificial Sequence
<220> FEATURE:
<223> OTHER INFORMATION: synthesized sequence

<400> SEQUENCE: 58
gacatccaga tgacccagtc tccatcgtcc ctgtctgcat ctgtgggaga cagagtcacc      60
atcacttgcc gggcaagtca gagcgttagc agctatttaa attggtatca gcagaaacca    120
gggaaagccc ctaacctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccccttt cggcggaggg      300 accaaactgg agatcaaa                                                  318

<210> SEQ ID NO 59
<211> LENGTH: 106
<212> TYPE: PRT
<213> ORGANISM: Artificial Sequence
<220> FEATURE:
<223> OTHER INFORMATION: synthesized sequence

<400> SEQUENCE: 59

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Val Ser Ser Tyr
                 20                  25                  30

Leu Asn Trp Tyr Gln Gln Lys Pro Gly Lys Ala Pro Asn Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Phe Gly Gly Gly Thr Lys Leu Glu Ile Lys
                100                 105

<210> SEQ ID NO 60
<211> LENGTH: 363
<212> TYPE: DNA
<213> ORGANISM: Artificial Sequence
<220> FEATURE:
<223> OTHER INFORMATION: synthesized sequence

<400> SEQUENCE: 60
caggtgcagc tggtggagtc tgggggaggc ttggtacagc ctggccggtc cctgagactc      60
tcctgtgtag cctctggatt cacctttgat gatcatgcca tgcactgggt caggcaaact    120
```

```
ccagagaagg gcctggagtg ggtctcaggt attagttgga atggaggtga catacgctat    180
gcggactctg tgaagggccg attcatcatc tccagagaca acgccaagaa ctccctgcat    240
ctgcaaatga acagtctgag aggtgaagac acggctgtgt attactgtgc gagagatggt    300
ggatatagtg ttcttagggc ttttgatatc tggggccaag ggaccacggt caccgtctcg    360
agc                                                                  363
```

<210> SEQ ID NO 61
<211> LENGTH: 121
<212> TYPE: PRT
<213> ORGANISM: Artificial Sequence
<220> FEATURE:
<223> OTHER INFORMATION: synthesized sequence

<400> SEQUENCE: 61

```
Gln Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asp Asp His
            20                  25                  30

Ala Met His Trp Val Arg Gln Thr Pro Glu Lys Gly Leu Glu Trp Val
        35                  40                  45

Ser Gly Ile Ser Trp Asn Gly Gly Asp Ile Arg Tyr Ala Asp Ser Val
    50                  55                  60

Lys Gly Arg Phe Ile Ile Ser Arg Asp Asn Ala Lys Asn Ser Leu His
65                  70                  75                  80

Leu Gln Met Asn Ser Leu Arg Gly Glu Asp Thr Ala Val Tyr Tyr Cys
                85                  90                  95

Ala Arg Asp Gly Gly Tyr Ser Val Leu Arg Ala Phe Asp Ile Trp Gly
            100                 105                 110

Gln Gly Thr Thr Val Thr Val Ser Ser
        115                 120
```

<210> SEQ ID NO 62
<211> LENGTH: 336
<212> TYPE: DNA
<213> ORGANISM: Artificial Sequence
<220> FEATURE:
<223> OTHER INFORMATION: synthesized sequence

<400> SEQUENCE: 62

```
cagtctgtgt tgacgcagcc gccctcagtg tctggggccc cggggcagag ggtcaccatc    60
tcctgcactg ggagcagctc aacatcgggg gcaggttatg atgtacactg gtaccagcag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
caggctgagg atgaggctga ttattactgc cagtcctatg acagcagcct gagtggttgg   300
gtgttcggcg gaggaaccca gctgatcatt ttaggt                             336
```

<210> SEQ ID NO 63
<211> LENGTH: 112
<212> TYPE: PRT
<213> ORGANISM: Artificial Sequence
<220> FEATURE:
<223> OTHER INFORMATION: synthesized sequence

<400> SEQUENCE: 63

```
Gln Ser Val Leu Thr Gln Pro Pro Ser Val Ser Gly Ala Pro Gly Gln
1               5                   10                  15
```

```
Arg Val Thr Ile Ser Cys Thr Gly Ser Ser Asn Ile Gly Ala Gly
             20                  25                  30

Tyr Asp Val His Trp Tyr Gln Gln Leu Pro Gly Thr Ala Pro Lys Leu
         35                  40                  45

Leu Ile Tyr Gly Asn Ser Asn Arg Pro Ser Gly Val Pro Asp Arg Phe
     50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Trp Val Phe Gly Gly Gly Thr Gln Leu Ile Ile Leu Gly
            100                 105                 110
```

<210> SEQ ID NO 64
<211> LENGTH: 1341
<212> TYPE: DNA
<213> ORGANISM: Artificial Sequence
<220> FEATURE:
<223> OTHER INFORMATION: synthesized sequence

<400> SEQUENCE: 64

```
caggtgcagc tacagcagtg gggcgcagga ctgttgaagc cttcggagac cctgtccctc      60
acctgcgctg tctatggtgg gtccttcagt gattactact ggaactggat ccgccagccc     120
ccagggaagg ggctggagtg gattggggaa atcaatcata atggaaacac caactccaac     180
ccgtccctca gagtcgagt cacccctatca ctagacacgt ccaagaacca gttctccctg     240
aagctgaggt ctgtgaccgc cgcggacacg gctgtgtatt actgtgcgtt tggatatagt     300
gactacgagt acaactggtt cgaccctgg ggccagggaa cctggtcac cgtctcctca     360
gctagcacca agggcccatc cgtcttcccc ctggcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacctgca acgtagatca caagcccagc aacaccaagg tggacaagag agttgagtcc     660
aaatatggtc ccccatgccc accatgccca gcacctgagt tcctgggggg accatcagtc     720
ttcctgttcc cccaaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtct ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggcta accgtggaca agagcaggtg gcaggagggg    1260
aatgtcttct catgctccgt gatgcatgag gctctgcaca accactacac acagaagagc    1320
ctctccctgt ctctgggtaa a                                              1341
```

<210> SEQ ID NO 65
<211> LENGTH: 447
<212> TYPE: PRT
<213> ORGANISM: Artificial Sequence
<220> FEATURE:
<223> OTHER INFORMATION: synthesized sequence

<400> SEQUENCE: 65

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Asn Gly Asn Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

-continued

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Leu Gly Lys
        435                 440                 445

<210> SEQ ID NO 66
<211> LENGTH: 642
<212> TYPE: DNA
<213> ORGANISM: Artificial Sequence
<220> FEATURE:
<223> OTHER INFORMATION: synthesized sequence

<400> SEQUENCE: 66
gaaattgtgt tgacacagtc tccagccacc ctgtctttgt ctccagggga aagagccacc      60
ctctcctgca gggccagtca gagtattagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctctcac ttttggccag     300
gggaccaacc tggagatcaa acgtacggtg gcggcgccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642

<210> SEQ ID NO 67
<211> LENGTH: 214
<212> TYPE: PRT
<213> ORGANISM: Artificial Sequence
<220> FEATURE:
<223> OTHER INFORMATION: synthesized sequence

<400> SEQUENCE: 67

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 68
<211> LENGTH: 2004
<212> TYPE: DNA
<213> ORGANISM: Artificial Sequence
<220> FEATURE:
<223> OTHER INFORMATION: synthesized sequence

<400> SEQUENCE: 68

| | | | | |
|---|---|---|---|---|
| ctccagccag | gggctgaggt | cccggtggtg | tgggcccagg | agggggctcc | tgcccagctc | 60 |
| ccctgcagcc | ccacaatccc | cctccaggat | ctcagccttc | tgcgaagagc | aggggtcact | 120 |
| tggcagcatc | agccagacag | tggcccgccc | gctgccgccc | ccggccatcc | cctggccccc | 180 |
| ggccctcacc | cggcggcgcc | ctcctcctgg | gggcccaggc | cccgccgcta | cacggtgctg | 240 |
| agcgtgggtc | ccggaggcct | gcgcagcggg | aggctgcccc | tgcagcccg | cgtccagctg | 300 |
| gatgagcgcg | gccggcagcg | cggggacttc | tcgctatggc | tgcgcccagc | ccggcgcgcg | 360 |
| gacgccggcg | agtaccgcgc | cgcggtgcac | ctcagggacc | gcgccctctc | ctgccgcctc | 420 |
| cgtctgcgcc | tgggccaggc | ctcgatgact | gccagccccc | caggatctct | cagagcctcc | 480 |
| gactgggtca | ttttgaactg | ctccttcagc | cgccctgacc | gcccagcctc | tgtgcattgg | 540 |
| ttccggaacc | ggggccaggg | ccgagtccct | gtccggagt | cccccatca | ccacttagcg | 600 |
| gaaagcttcc | tcttcctgcc | ccaagtcagc | cccatggact | ctgggccctg | gggctgcatc | 660 |
| ctcacctaca | gagatggctt | caacgtctcc | atcatgtata | acctcactgt | tctgggtctg | 720 |
| gagcccccaa | ctcccttgac | agtgtacgct | ggagcaggtt | ccagggtggg | gctgccctgc | 780 |
| cgcctgcctg | ctggtgtggg | gacccggtct | ttcctcactg | ccaagtggac | tcctcctggg | 840 |
| ggaggccctg | acctcctggt | gactggagac | aatggcgact | ttacccttcg | actagaggat | 900 |
| gtgagccagg | cccaggctgg | gacctacacc | tgccatatcc | atctgcagga | acagcagctc | 960 |
| aatgccactg | tcacattggc | aatcatcaca | gtgactccca | atcctttggg | gtcacctgga | 1020 |
| tccctgggga | agctgctttg | tgaggtgact | ccagtatctg | gacaagaacg | ctttgtgtgg | 1080 |
| agctctctgg | acacccatc | ccagaggagt | ttctcaggac | cttggctgga | ggcacaggag | 1140 |
| gcccagctcc | tttccagcc | ttggcaatgc | cagctgtacc | aggggagag | gcttcttgga | 1200 |
| gcagcagtgt | acttcacaga | gctgtctagc | ccaggtgccc | aacgctctgg | gagagcccca | 1260 |
| ggtgccctcc | cagcaggcca | cctcgatatc | gagggtcgta | tggatgagcc | cagagggccc | 1320 |
| acaatcaagc | cctgtcctcc | atgcaaatgc | ccagcaccta | acctcttggg | tggaccatcc | 1380 |
| gtcttcatct | tccctccaaa | gatcaaggat | gtactcatga | tctccctgag | ccccatagtc | 1440 |
| acatgtgtgg | tggtggatgt | gagcgaggat | gacccagatg | tccagatcag | ctggtttgtg | 1500 |
| aacaacgtgg | aagtacacac | agctcagaca | caaacccata | gagaggatta | caacagtact | 1560 |
| ctccggggtg | tcagtgccct | ccccatccag | caccaggact | ggatgagtgg | caaggagttc | 1620 |

-continued

```
aaatgcaagg tcaacaacaa agacctccca gcgcccatcg agagaaccat ctcaaaaccc    1680
aaagggtcag taagagctcc acaggtatat gtcttgcctc caccagaaga agagatgact    1740
aagaaacagg tcactctgac ctgcatggtc acagacttca tgcctgaaga catttacgtg    1800
gagtggacca acaacgggaa aacagagcta aactacaaga acactgaacc agtcctggac    1860
tctgatggtt cttacttcat gtacagcaag ctgagagtgg aaaagaagaa ctgggtggaa    1920
agaaatagct actcctgttc agtggtccac gagggtctgc acaatcacca cacgactaag    1980
agcttctccc ggactccagg taaa                                           2004
```

<210> SEQ ID NO 69
<211> LENGTH: 668
<212> TYPE: PRT
<213> ORGANISM: Artificial Sequence
<220> FEATURE:
<223> OTHER INFORMATION: synthesized sequence

<400> SEQUENCE: 69

```
Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
    50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Ala
        115                 120                 125

Val His Leu Arg Asp Arg Ala Leu Ser Cys Arg Leu Arg Leu Arg Leu
    130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270

Thr Ala Lys Trp Thr Pro Pro Gly Gly Gly Pro Asp Leu Leu Val Thr
        275                 280                 285

Gly Asp Asn Gly Asp Phe Thr Leu Arg Leu Glu Asp Val Ser Gln Ala
```

```
            290                 295                 300
Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
            340                 345                 350

Ser Gly Gln Glu Arg Phe Val Trp Ser Ser Leu Asp Thr Pro Ser Gln
        355                 360                 365

Arg Ser Phe Ser Gly Pro Trp Leu Glu Ala Gln Glu Ala Gln Leu Leu
    370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Pro Ala Gly His Leu Asp Ile Glu Gly
            420                 425                 430

Arg Met Asp Glu Pro Arg Gly Pro Thr Ile Lys Pro Cys Pro Pro Cys
        435                 440                 445

Lys Cys Pro Ala Pro Asn Leu Leu Gly Gly Pro Ser Val Phe Ile Phe
    450                 455                 460

Pro Pro Lys Ile Lys Asp Val Leu Met Ile Ser Leu Ser Pro Ile Val
465                 470                 475                 480

Thr Cys Val Val Val Asp Val Ser Glu Asp Asp Pro Asp Val Gln Ile
                485                 490                 495

Ser Trp Phe Val Asn Asn Val Glu Val His Thr Ala Gln Thr Gln Thr
            500                 505                 510

His Arg Glu Asp Tyr Asn Ser Thr Leu Arg Val Val Ser Ala Leu Pro
        515                 520                 525

Ile Gln His Gln Asp Trp Met Ser Gly Lys Glu Phe Lys Cys Lys Val
    530                 535                 540

Asn Asn Lys Asp Leu Pro Ala Pro Ile Glu Arg Thr Ile Ser Lys Pro
545                 550                 555                 560

Lys Gly Ser Val Arg Ala Pro Gln Val Tyr Val Leu Pro Pro Pro Glu
                565                 570                 575

Glu Glu Met Thr Lys Lys Gln Val Thr Leu Thr Cys Met Val Thr Asp
            580                 585                 590

Phe Met Pro Glu Asp Ile Tyr Val Glu Trp Thr Asn Asn Gly Lys Thr
        595                 600                 605

Glu Leu Asn Tyr Lys Asn Thr Glu Pro Val Leu Asp Ser Asp Gly Ser
    610                 615                 620

Tyr Phe Met Tyr Ser Lys Leu Arg Val Glu Lys Asn Trp Val Glu
625                 630                 635                 640

Arg Asn Ser Tyr Ser Cys Ser Val Val His Glu Gly Leu His Asn His
                645                 650                 655

His Thr Thr Lys Ser Phe Ser Arg Thr Pro Gly Lys
            660                 665
```

<210> SEQ ID NO 70
<211> LENGTH: 1278
<212> TYPE: DNA
<213> ORGANISM: Artificial Sequence
<220> FEATURE:
<223> OTHER INFORMATION: synthesized sequence

<400> SEQUENCE: 70

```
tcagggcctg ggaaagagct ccccgtggtg tgggcccagg agggagctcc cgtccatctt      60
ccctgcagcc tcaaatcccc caacctggat cctaactttc tacgaagagg aggggttatc     120
tggcaacatc aaccagacag tggccaaccc actcccatcc cggcccttga ccttcaccag     180
gggatgccct cgcctagaca acccgcaccc ggtcgctaca cggtgctgag cgtggctcca     240
ggaggcctgc gcagcgggag gcagcccctg catccccacg tgcagctgga ggagcgcggc     300
ctccagcgcg gggacttctc tctgtggttg cgcccagctc tgcgcaccga tgcgggcgag     360
taccacgcca ccgtgcgcct cccgaaccgc gccctctcct gcagtctccg cctgcgcgtc     420
ggccaggcct cgatgattgc tagtccctca ggagtcctca agctgtctga ttgggtcctt     480
ttgaactgct ccttcagccg tcctgaccgc ccagtctctg tgcactggtt ccagggccag     540
aaccgagtgc ctgtctacaa ctcaccgcgt catttttag ctgaaacttt cctgttactg      600
ccccaagtca gccccctgga ctctgggacc tggggctgtg tcctcaccta cagagatggc     660
ttcaatgtct ccatcacgta caacctcaag gttctgggtc tggagcccgt agcccctctg     720
acagtgtacg ctgctgaagg ttctaggggtg gagctgccct gtcatttgcc cccaggagtg    780
gggacccctt ctttgctcat tgccaagtgg actcctcctg gaggaggtcc tgagctcccc    840
gtggctggaa agagtggcaa ttttaccctt caccttgagg ctgtgggtct ggcacaggct    900
gggacctaca cctgtagcat ccatctgcag ggacagcagc tcaatgccac tgtcacgttg    960
gcggtcatca cagtgactcc caaatccttc gggttacctg gctcccgggg gaagctgttg   1020
tgtgaggtaa ccccggcatc tggaaaggaa agatttgtgt ggcgtcccct gaacaatctg   1080
tccaggagtt gcccgggccc tgtgctggag attcaggagg ccaggctcct gctgagcga    1140
tggcagtgtc agctgtacga gggccagagg cttcttggag cgacagtgta cgccgcagag   1200
tctagctcag gcgcccacag tgctaggaga atctcaggtg accttaaagg aggccatctc   1260
catcatcacc atcatcat                                                   1278
```

<210> SEQ ID NO 71
<211> LENGTH: 426
<212> TYPE: PRT
<213> ORGANISM: Artificial Sequence
<220> FEATURE:
<223> OTHER INFORMATION: synthesized sequence

<400> SEQUENCE: 71

```
Ser Gly Pro Gly Lys Glu Leu Pro Val Val Trp Ala Gln Glu Gly Ala
1               5                   10                  15

Pro Val His Leu Pro Cys Ser Leu Lys Ser Pro Asn Leu Asp Pro Asn
            20                  25                  30

Phe Leu Arg Arg Gly Gly Val Ile Trp Gln His Gln Pro Asp Ser Gly
        35                  40                  45

Gln Pro Thr Pro Ile Pro Ala Leu Asp Leu His Gln Gly Met Pro Ser
    50                  55                  60

Pro Arg Gln Pro Ala Pro Gly Arg Tyr Thr Val Leu Ser Val Ala Pro
65                  70                  75                  80

Gly Gly Leu Arg Ser Gly Arg Gln Pro Leu His Pro His Val Gln Leu
                85                  90                  95

Glu Glu Arg Gly Leu Gln Arg Gly Asp Phe Ser Leu Trp Leu Arg Pro
            100                 105                 110

Ala Leu Arg Thr Asp Ala Gly Glu Tyr His Ala Thr Val Arg Leu Pro
        115                 120                 125
```

Asn Arg Ala Leu Ser Cys Ser Leu Arg Leu Arg Val Gly Gln Ala Ser
            130                 135                 140

Met Ile Ala Ser Pro Ser Gly Val Leu Lys Leu Ser Asp Trp Val Leu
145                 150                 155                 160

Leu Asn Cys Ser Phe Ser Arg Pro Asp Arg Pro Val Ser Val His Trp
                165                 170                 175

Phe Gln Gly Gln Asn Arg Val Pro Val Tyr Asn Ser Pro Arg His Phe
            180                 185                 190

Leu Ala Glu Thr Phe Leu Leu Leu Pro Gln Val Ser Pro Leu Asp Ser
        195                 200                 205

Gly Thr Trp Gly Cys Val Leu Thr Tyr Arg Asp Gly Phe Asn Val Ser
    210                 215                 220

Ile Thr Tyr Asn Leu Lys Val Leu Gly Leu Glu Pro Val Ala Pro Leu
225                 230                 235                 240

Thr Val Tyr Ala Ala Glu Gly Ser Arg Val Glu Leu Pro Cys His Leu
                245                 250                 255

Pro Pro Gly Val Gly Thr Pro Ser Leu Leu Ile Ala Lys Trp Thr Pro
            260                 265                 270

Pro Gly Gly Gly Pro Glu Leu Pro Val Ala Gly Lys Ser Gly Asn Phe
        275                 280                 285

Thr Leu His Leu Glu Ala Val Gly Leu Ala Gln Ala Gly Thr Tyr Thr
    290                 295                 300

Cys Ser Ile His Leu Gln Gly Gln Gln Leu Asn Ala Thr Val Thr Leu
305                 310                 315                 320

Ala Val Ile Thr Val Thr Pro Lys Ser Phe Gly Leu Pro Gly Ser Arg
                325                 330                 335

Gly Lys Leu Leu Cys Glu Val Thr Pro Ala Ser Gly Lys Glu Arg Phe
            340                 345                 350

Val Trp Arg Pro Leu Asn Asn Leu Ser Arg Ser Cys Pro Gly Pro Val
        355                 360                 365

Leu Glu Ile Gln Glu Ala Arg Leu Leu Ala Glu Arg Trp Gln Cys Gln
370                 375                 380

Leu Tyr Glu Gly Gln Arg Leu Leu Gly Ala Thr Val Tyr Ala Ala Glu
385                 390                 395                 400

Ser Ser Ser Gly Ala His Ser Ala Arg Arg Ile Ser Gly Asp Leu Lys
                405                 410                 415

Gly Gly His Leu His His His His
            420                 425

<210> SEQ ID NO 72
<211> LENGTH: 372
<212> TYPE: DNA
<213> ORGANISM: Artificial Sequence
<220> FEATURE:
<223> OTHER INFORMATION: synthesized sequence

<400> SEQUENCE: 72
gaggttcagc tgttggagtc tggagctgag gtgaagaagc tggggcctc agtgaaggtc      60 tcctgcaagg cttctggtta cacctttacc agctatggta tcagctgggt gcgacaggcc    120
cctggacaag ggcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gagagatggc    300
tggtgggagc tactacgtcc cgatgaagct tttgatatct ggggccaagg gacaacggtc    360
accgtctcga gc         372

<210> SEQ ID NO 73
<211> LENGTH: 124
<212> TYPE: PRT
<213> ORGANISM: Artificial Sequence
<220> FEATURE:
<223> OTHER INFORMATION: synthesized sequence

<400> SEQUENCE: 73

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Trp Trp Glu Leu Leu Arg Pro Asp Glu Ala Phe Asp
            100                 105                 110

Ile Trp Gly Gln Gly Thr Thr Val Thr Val Ser Ser
        115                 120

<210> SEQ ID NO 74
<211> LENGTH: 372
<212> TYPE: DNA
<213> ORGANISM: Artificial Sequence
<220> FEATURE:
<223> OTHER INFORMATION: synthesized sequence

<400> SEQUENCE: 74
gaggttcagc tgttggagtc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg atcagcgctt acaatggtaa cacaaactat    180
gcacagaagc tccagggcag agtcaccatg accacagaca catccacgag cacagcctac   240
atggagctga ggagcctgag atctgacgag acggccgtgt attactgtgc gagagatggc   300
tggtgggagc tactacgtcc cgatgatgct tttgatatct ggggccaagg gacaacggtc   360
accgtctcga gc         372

<210> SEQ ID NO 75
<211> LENGTH: 124
<212> TYPE: PRT
<213> ORGANISM: Artificial Sequence
<220> FEATURE:
<223> OTHER INFORMATION: synthesized sequence

<400> SEQUENCE: 75

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

-continued

Gly Trp Ile Ser Ala Tyr Asn Gly Asn Thr Asn Tyr Ala Gln Lys Leu
          50                  55                  60

Gln Gly Arg Val Thr Met Thr Thr Asp Thr Ser Thr Ser Thr Ala Tyr
65                      70                  75                  80

Met Glu Leu Arg Ser Leu Arg Ser Glu Asp Thr Ala Val Tyr Tyr Cys
                    85                  90                  95

Ala Arg Asp Gly Trp Trp Glu Leu Leu Arg Pro Asp Asp Ala Phe Asp
                100                 105                 110

Ile Trp Gly Gln Gly Thr Thr Val Thr Val Ser Ser
                115                 120

<210> SEQ ID NO 76
<211> LENGTH: 372
<212> TYPE: DNA
<213> ORGANISM: Artificial Sequence
<220> FEATURE:
<223> OTHER INFORMATION: synthesized sequence

<400> SEQUENCE: 76
gaggttcagc tgttggagtc tggagctgag gtgaagaagc ctggggcctc agtgaaggtc      60
tcctgcaagg cttctggtta cacctttacc agctatggta tcagctgggt gcgacaggcc     120
cctggacaag ggcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgaggac acggccgtgt attactgtgc gagagatggc     300
tggtgggagc tactacgtcc cgatgatgct tttgatatct ggggccaagg gacaacggtc     360
accgtctcga gc                                                         372

<210> SEQ ID NO 77
<211> LENGTH: 124
<212> TYPE: PRT
<213> ORGANISM: Artificial Sequence
<220> FEATURE:
<223> OTHER INFORMATION: synthesized sequence

<400> SEQUENCE: 77

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
          50                  55                  60

Gln Gly Arg Val Thr Met Thr Thr Asp Thr Ser Thr Ser Thr Ala Tyr
65                      70                  75                  80

Met Glu Leu Arg Ser Leu Arg Ser Glu Asp Thr Ala Val Tyr Tyr Cys
                    85                  90                  95

Ala Arg Asp Gly Trp Trp Glu Leu Leu Arg Pro Asp Asp Ala Phe Asp
                100                 105                 110

Ile Trp Gly Gln Gly Thr Thr Val Thr Val Ser Ser
                115                 120

<210> SEQ ID NO 78
<211> LENGTH: 372
<212> TYPE: DNA
<213> ORGANISM: Artificial Sequence
<220> FEATURE:
<223> OTHER INFORMATION: synthesized sequence

<400> SEQUENCE: 78

```
gaggttcagc tgttggagtc tggagctgag gtgaagaagc ctggggcctc agtgaaggtc      60
tcctgcaagg cttctggtta cacctttacc agctatggta tcagctgggt gcgacaggcc     120
cctggacaag ggcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggccgtgt attactgtgc gagagatggc     300
tggtgggagc tactacgtcc cgaagatgct tttgatatct ggggccaagg gacaacggtc     360
accgtctcga gc                                                         372
```

<210> SEQ ID NO 79
<211> LENGTH: 124
<212> TYPE: PRT
<213> ORGANISM: Artificial Sequence
<220> FEATURE:
<223> OTHER INFORMATION: synthesized sequence

<400> SEQUENCE: 79

```
Glu Val Gln Leu Leu Glu Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Gly Trp Trp Glu Leu Leu Arg Pro Glu Asp Ala Phe Asp
            100                 105                 110
Ile Trp Gly Gln Gly Thr Thr Val Thr Val Ser Ser
        115                 120
```

<210> SEQ ID NO 80
<211> LENGTH: 372
<212> TYPE: DNA
<213> ORGANISM: Artificial Sequence
<220> FEATURE:
<223> OTHER INFORMATION: synthesized sequence

<400> SEQUENCE: 80

```
gaggttcagc tgttggagtc tggagctgag gtgaagaagc ctggggcctc agtgaaggtc      60
tcctgcaagg cttctggtta cacctttacc agctatggta tcagctgggt gcgacaggcc     120
cctggacaag ggcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgag acggccgtgt attactgtgc gagagatggc     300
tggtgggagc tactacgtcc cgaagatgct tttgatatct ggggccaagg gacaacggtc     360
accgtctcga gc                                                         372
```

<210> SEQ ID NO 81

```
<211> LENGTH: 124
<212> TYPE: PRT
<213> ORGANISM: Artificial Sequence
<220> FEATURE:
<223> OTHER INFORMATION: synthesized sequence

<400> SEQUENCE: 81
```

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Glu Thr Ala Val Tyr Tyr Cys
                85                  90                  95

Ala Arg Asp Gly Trp Trp Glu Leu Leu Arg Pro Glu Asp Ala Phe Asp
            100                 105                 110

Ile Trp Gly Gln Gly Thr Thr Val Thr Val Ser Ser
        115                 120

```
<210> SEQ ID NO 82
<211> LENGTH: 372
<212> TYPE: DNA
<213> ORGANISM: Artificial Sequence
<220> FEATURE:
<223> OTHER INFORMATION: synthesized sequence

<400> SEQUENCE: 82
```

| | |
|---|---|
| gaggttcagc tgttggagtc tggagctgag gtgaagaagc ctggggcctc agtgaaggtc | 60 |
| tcctgcaagg cttctggtta cacctttacc agctatggta tcagctgggt gcgacaggcc | 120 |
| cctggacaag ggcttgagtg gatgggatgg atcagcgctt acaatggtaa cacaaactat | 180 |
| gcacagaagc tccagggcag agtcaccatg accacagaca catccacgag cacagcctac | 240 |
| atggagctga ggagcctgag atctgaggac acggccgtgt attactgtgc gagagatggc | 300 |
| tggtgggagc tactacgtcc cgatgaagct tttgatatct ggggccaagg gacaacggtc | 360 |
| accgtctcga gc | 372 |

```
<210> SEQ ID NO 83
<211> LENGTH: 124
<212> TYPE: PRT
<213> ORGANISM: Artificial Sequence
<220> FEATURE:
<223> OTHER INFORMATION: synthesized sequence

<400> SEQUENCE: 83
```

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr

```
                65                  70                  75                  80
Met Glu Leu Arg Ser Leu Arg Ser Glu Asp Thr Ala Val Tyr Tyr Cys
                    85                  90                  95

Ala Arg Asp Gly Trp Trp Glu Leu Leu Arg Pro Asp Glu Ala Phe Asp
                100                 105                 110

Ile Trp Gly Gln Gly Thr Thr Val Thr Val Ser Ser
            115                 120
```

<210> SEQ ID NO 84
<211> LENGTH: 372
<212> TYPE: DNA
<213> ORGANISM: Artificial Sequence
<220> FEATURE:
<223> OTHER INFORMATION: synthesized sequence

<400> SEQUENCE: 84

```
gaggttcagc tgttggagtc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgag acggccgtgt attactgtgc gagagatggc   300
tggtgggagc tactacgtcc cgatgaagct tttgatatct ggggccaagg acaacggtc   360 accgtctcga gc                                                         372
```

<210> SEQ ID NO 85
<211> LENGTH: 124
<212> TYPE: PRT
<213> ORGANISM: Artificial Sequence
<220> FEATURE:
<223> OTHER INFORMATION: synthesized sequence

<400> SEQUENCE: 85

```
Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Asp Gly Trp Trp Glu Leu Leu Arg Pro Asp Glu Ala Phe Asp
                100                 105                 110

Ile Trp Gly Gln Gly Thr Thr Val Thr Val Ser Ser
            115                 120
```

<210> SEQ ID NO 86
<211> LENGTH: 372
<212> TYPE: DNA
<213> ORGANISM: Artificial Sequence
<220> FEATURE:
<223> OTHER INFORMATION: synthesized sequence

<400> SEQUENCE: 86

```
gaggttcagc tgttggagtc tggagctgag gtgaagaagc ctggggcctc agtgaaggtc      60
tcctgcaagg cttctggtta cacctttacc agctatggta tcagctgggt gcgacaggcc     120
cctggacaag ggcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgaggac acggccgtgt attactgtgc gagagatggc     300
tggtgggagc tactacgtcc cgaagatgct tttgatatct ggggccaagg gacaacggtc     360
accgtctcga gc                                                         372
```

<210> SEQ ID NO 87
<211> LENGTH: 124
<212> TYPE: PRT
<213> ORGANISM: Artificial Sequence
<220> FEATURE:
<223> OTHER INFORMATION: synthesized sequence

<400> SEQUENCE: 87

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Asp Gly Trp Trp Glu Leu Leu Arg Pro Glu Asp Ala Phe Asp
            100                 105                 110

Ile Trp Gly Gln Gly Thr Thr Val Thr Val Ser Ser
        115                 120

<210> SEQ ID NO 88
<211> LENGTH: 5
<212> TYPE: PRT
<213> ORGANISM: Artificial Sequence
<220> FEATURE:
<223> OTHER INFORMATION: synthesized sequence

<400> SEQUENCE: 88

Ser Tyr Gly Ile Ser
1               5

<210> SEQ ID NO 89
<211> LENGTH: 17
<212> TYPE: PRT
<213> ORGANISM: Artificial Sequence
<220> FEATURE:
<223> OTHER INFORMATION: synthesized sequence

<400> SEQUENCE: 89

Trp Ile Ser Ala Tyr Asn Gly Asn Thr Asn Tyr Ala Gln Lys Leu Gln
1               5                   10                  15

Gly

<210> SEQ ID NO 90
<211> LENGTH: 15

```
<212> TYPE: PRT
<213> ORGANISM: Artificial Sequence
<220> FEATURE:
<223> OTHER INFORMATION: synthesized sequence

<400> SEQUENCE: 90

Asp Gly Trp Trp Glu Leu Leu Arg Pro Asp Asp Ala Phe Asp Ile
1               5                   10                  15

<210> SEQ ID NO 91
<211> LENGTH: 11
<212> TYPE: PRT
<213> ORGANISM: Artificial Sequence
<220> FEATURE:
<223> OTHER INFORMATION: synthesized sequence

<400> SEQUENCE: 91

Ser Gly Asp Lys Leu Gly Asp Lys Tyr Ala Tyr
1               5                   10

<210> SEQ ID NO 92
<211> LENGTH: 7
<212> TYPE: PRT
<213> ORGANISM: Artificial Sequence
<220> FEATURE:
<223> OTHER INFORMATION: synthesized sequence

<400> SEQUENCE: 92

Tyr Asp Ser Asp Arg Pro Ser
1               5

<210> SEQ ID NO 93
<211> LENGTH: 11
<212> TYPE: PRT
<213> ORGANISM: Artificial Sequence
<220> FEATURE:
<223> OTHER INFORMATION: synthesized sequence

<400> SEQUENCE: 93

Gln Val Trp Asp Ser Ser Ser Asp Gln Val Val
1               5                   10
```